(12) United States Patent
Walder et al.

(10) Patent No.: US 10,858,699 B2
(45) Date of Patent: Dec. 8, 2020

(54) CLEAVABLE HAIRPIN PRIMERS

(71) Applicant: Integrated DNA Technologies, Inc., Coralville, IA (US)

(72) Inventors: Joseph A. Walder, Chicago, IL (US); Joseph Dobosy, Coralville, IA (US); Mark Aaron Behlke, Coralville, IA (US)

(73) Assignee: Integrated DNA Technologies, Inc., Coralville, IA (US)

( * ) Notice: Subject to any disclaimer, the term of this patent is extended or adjusted under 35 U.S.C. 154(b) by 43 days.

(21) Appl. No.: 15/689,084

(22) Filed: Aug. 29, 2017

(65) Prior Publication Data

US 2018/0057868 A1  Mar. 1, 2018

Related U.S. Application Data

(60) Provisional application No. 62/381,177, filed on Aug. 30, 2016.

(51) Int. Cl.
| | | |
|---|---|---|
| *C12P 19/34* | (2006.01) | |
| *C12Q 1/6853* | (2018.01) | |
| *C12Q 1/6858* | (2018.01) | |
| *C12Q 1/6806* | (2018.01) | |
| *C12Q 1/6809* | (2018.01) | |
| *C12Q 1/6869* | (2018.01) | |

(52) U.S. Cl.
CPC ......... *C12Q 1/6853* (2013.01); *C12Q 1/6806* (2013.01); *C12Q 1/6809* (2013.01); *C12Q 1/6858* (2013.01); *C12Q 1/6869* (2013.01); *C12N 2310/122* (2013.01)

(58) Field of Classification Search
CPC ............ C12Q 1/6858; C12Q 2521/327; C12Q 2525/121; C12Q 2525/161; C12Q 2525/186; C12Q 2525/301; C12Q 2531/113; C12Q 1/6806; C12Q 1/6809; C12Q 1/6853; C12Q 1/6869; C12N 2310/122
See application file for complete search history.

(56) References Cited

U.S. PATENT DOCUMENTS

| | | | | |
|---|---|---|---|---|
| 2010/0167353 A1* | 7/2010 | Walder | ................ | C12Q 1/6844 435/91.2 |
| 2015/0080241 A1* | 3/2015 | Kim | ..................... | C12Q 1/6848 506/9 |
| 2016/0046995 A1* | 2/2016 | Kochanczyk | ........ | C12Q 1/6827 506/9 |

* cited by examiner

*Primary Examiner* — Cynthia B Wilder
(74) *Attorney, Agent, or Firm* — John A. Petravich; David J. Youngkin

(57) ABSTRACT

The invention describes composition and methods of use for novel hairpin blocked-cleavable primers. In one embodiment unblocking occurs through action of RNase H2. The method improves the specificity of PCR and reduces primer dimer events, enabling higher level multiplex reactions. Additionally, the invention protects RNA-containing primers from attack by single-strand RNases.

9 Claims, 31 Drawing Sheets
Specification includes a Sequence Listing.

CLEAVABLE HAIRPIN PRIMERS

CROSS-REFERENCE TO RELATED APPLICATIONS

This patent application claims the benefit of U.S. Provisional Patent Application No. 62/381,177, filed Aug. 30, 2016.

FIELD OF THE INVENTION

The invention enables enhanced multiplexing and primer-dimer prevention using cleavable hairpin-protected primers. Additionally, the invention protects the primers against attack by single-stranded RNases.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 11,077 Byte ASCII (Text) file named "PA2017-21 Cleavable Hairpin Primers_ST25.txt" created on Aug. 25, 2017.

BACKGROUND OF THE INVENTION

The amplification of nucleic acids is a widely used tool in the life sciences. One of the most widely used methods is the polymerase chain reaction (PCR). The specificity of primer-based amplification reactions, such as PCR, largely depends on the specificity of primer hybridization with a DNA template and the ability of a DNA polymerase enzyme to commence DNA synthesis at the 3'-end of that primer. Under the elevated temperatures used in a typical amplification reaction, the primers ideally hybridize only to the intended target sequence and form primer extension products to produce the complement of the target sequence. However, amplification reaction mixtures are typically assembled at room temperature, well below the temperature needed to ensure primer hybridization specificity. Under lower temperature conditions, the primers often bind to off-target partially complementary nucleic acid sequences or to other primers and can initiate the synthesis of undesired extension products, which in turn can be amplified along with the target sequence. Amplification of non-desired primer extension products can compete with amplification of the desired target sequences and can significantly decrease the efficiency of the amplification of the desired sequence. These undesired side amplification reactions can also give rise to false positive results.

Primer dimers is a term that relates to formation of an undesired reaction product that often arises from interaction of one or both primers with themselves independent of template, forming unwanted small reaction products. Such products can form at high efficiency even when the degree of primer-primer overlap is small because the primers are present at high concentration. Primer dimers are a significant problem in PCR and other amplification techniques. This non-specific amplification leads to competition for PCR reagents, potentially inhibiting the amplification of the correct target sequences, may interfere with accurate quantification, and can lead to false positive or false negative signals.

Primer dimers are especially prevalent in multiplex PCR where two or more primer pairs are used simultaneously. The presence of multiple primer pairs in the same reaction increases the likelihood of unwanted interactions occurring between primers independent of template. Multiplex PCR amplifies several different DNA target sequences simultaneously in a single reaction tube and uses multiple primer sets within a single PCR reaction mixture. Each primer set targets a specific sequence. However, each primer set must be optimized to work correctly within a single reaction. Even with careful primer design multiplex PCR is highly susceptible to the formation of primer dimers, off target or non-specific amplification, and preferential amplification of overly abundant species.

Non-specific amplification refers to the amplification of undesired products that have imperfect complementarity to the primers. Non-specific amplification can by reduced by preventing initiation of primer extension by DNA polymerase from primers bound to non-complementary target sequences. In one method, known as "hot-start", one or more of the reaction mix reagents is withheld from the reaction mixture until the temperature is raised sufficiently to provide the necessary hybridization specificity. This functions to reduce off-target non-specific priming by reducing the number of primers bound to off-target sites using improved temperature control over the primer hybridization event. Hot start methods are commonly employed today, and generally require use of either chemically modified DNA polymerases that are inactive and reactivate after heating, or unmodified DNA polymerases that have been reversibly inactivated by binding of an anti-polymerase aptamer or antibody molecule, which denatures and allows for polymerase activation upon heating. These methods increase the cost of performing PCR. U.S. Pat. Nos. 5,773,258 and 5,677,152, both incorporated herein by reference, describe DNA polymerases reversibly inactivated by the covalent attachment of a modifier group. Incubation of the inactivated. DNA polymerase at high temperature results in cleavage of the modifier-enzyme bond, thereby releasing an active form of the enzyme. Non-covalent reversible inhibition of a DNA polymerase by DNA polymerase-specific antibodies is described in U.S. Pat. No. 5,338,671, incorporated herein by reference.

RNase H2-dependent PCR (rhPCR) (see U.S. Pat. No. 8,911,948 B2, incorporated herein by reference) can be utilized for exponential DNA amplification. The use of blocked-cleavable primers in rhPCR enhances the specificity of PCR. The method employs blocked-cleavable primers that are inactive in their native form, unable to prime DNA synthesis. Upon binding of primer to target DNA, a substrate for RNase H2 is formed at the site of a single RNA residue in the primer. If perfect complementarity is present, RNase H2 rapidly cleaves the primer at the RNA site, removing the blocking group and activating the primer, allowing DNA synthesis to proceed. If imperfect complementarity is present, the unblocking reaction proceeds slowly or not at all, thereby improving the specificity of the priming event. The improved specificity of rhPCR affects both interactions with target DNA as well as primers. While the use of blocked-cleavable primers in rhPCR to improve reaction specificity is well documented, the system is not perfect and undesired amplification events can still occur. For example, in highly multiplexed PCR reactions, many different primer sequences are present in a single reaction mixture. In this setting, even with careful primer design some transient hybridization events sometimes occur between primers having limited homology that are sufficient to allow primer unblocking, resulting in unwanted primer dimer formation. Also, the presence of an RNA residue in the primer allows for potential contaminating single-stranded RNases (ssRNases) to cleave the primer, resulting in a 3' phosphate, and an inactive or "dead" primer which will compete with other primers and interfere with PCR amplification of the target, reducing reaction efficiency.

The present invention describes novel hairpin blocked-cleavable primers that further reduce primer-dimer formation and offer increased specificity when used in rhPCR. The hairpin blocked-cleavable primers improve the performance of multiplex rhPCR reactions, and also protect primers against attack by single-stranded RNases. These and other advantages of the invention, as well as additional inventive features, will be apparent from the description of the invention provided herein.

BRIEF SUMMARY OF THE INVENTION

The invention provides improved methods of performing PCR and multiplex PCR that utilize hairpin blocked RNase H-cleavable primers that improves reaction efficiency and specificity. Further embodiments suppress the formation of primer dimers and other artifacts of false priming events. Additionally the invention protects RNA-containing primers from attack by ssRNases.

In one embodiment a hairpin blocked cleavable primer is provided, the blocked cleavable primer comprising from 5' to 3': (i) a target binding domain that is complementary to the target nucleic acid sequence; (ii) optionally a discrimination domain; (iii) a cleavable domain that, when hybridized to a complementary target nucleic acid sequence, is cleaved by a cleaving enzyme; (iv) a loop domain; (v) a stem domain that has complementarity to the cleavable domain and 1-10 neighboring bases; and (vi) a blocking domain that prevents extension of the primer. A hairpin blocked-cleavable primer of this design is henceforth referred to as a hairpin rhPrimer.

The target binding domain binds to the target nucleic acid and functions much like a traditional PCR primer except that additional domains reside on the 3'-end of the hairpin rhPrimer.

A discrimination domain may exist between the target binding domain and the cleavable domain. In one embodiment, this domain is a single nucleic acid residue which defines the final specificity of the primer and provides the ability to distinguish the presence of this base in the target nucleic acid sequence (e.g., a single nucleic polymorphism (SNP) or allele discrimination).

In a further embodiment the cleavable domain comprises a region that can be cleaved by the action of a nuclease enzyme. The cleaving enzyme can be any nuclease that cuts the probe in a sequence specific fashion at single defined site and, for example, can include an RNase H enzyme (which cleaves at one or more RNA residues) or a nickase restriction endonuclease (which cleaves in a defined sequence context). One embodiment employs a single RNA residue and the cleaving enzyme is RNase H2. Additional residues may be required in this domain to provide for optimal cleaving activity. These requirements can vary depending on the identity of the cleaving enzyme (e.g., the optimal substrate for RNase H2 is different from RNase H1 or a nickase restriction endonuclease).

In one embodiment the loop domain is one of, or a mixture of, DNA, modified DNA/RNA or DNA/RNA analogs, or non-nucleic acid modifiers.

In one embodiment the stem domain comprises one of, or a mixture of, DNA, modified DNA/RNA or DNA/RNA analogs, or non-nucleic acid linker modifiers. The stem domain may contain one or more additional modifications, either as a substitution or insertion. In another embodiment, the stem's length extends from the 3' end of the loop and ends at the point of complementary to the cleaving domain or extends an additional 1 to 3 bases. The modified stem domain thus forms a duplex with the cleavable domain (and neighboring residues, depending on the length of the stem domain); however this duplex does not form a substrate for RNase H2. In this embodiment the stem can base pair with the cleavable RNA residue and extend into the target-binding domain without forming a substrate for RNase H2. Hybridization of the hairpin blocked-cleavable primer to a target nucleic acid leads to unfolding of the synthetic stem and forms a substrate for RNase H2 at the cleaving domain (typically containing at least one RNA residue), allowing the unblocking reaction to proceed.

In a further embodiment, the stem domain comprises DNA residues. The stem domain comprises 3-20 unmodified DNA residues or 2'-modified residues that are complementary to and will hybridize to the cleavable domain and neighboring bases, including the RNA residue(s). The stem domain forms a duplex with the cleavable domain (and neighboring residues, depending on the length of the stem domain); however this duplex does not form a substrate for RNase H2. The stem domain may have base complementarity to and hybridize to the cleavable RNA residue, but complementarity does not extend more than 1 to 4 bases into the target-binding domain. Short complementarity in this region ensures that the primer hairpin is not a substrate for RNase H. Hybridization of the hairpin blocked-cleavable primer to a target DNA leads to unfolding of the stem, and the primer forms a substrate for RNase H2 at the RNA residue(s), allowing the unblocking reaction to proceed.

In an alternative embodiment, the stem domain comprises DNA residues, and one or more modified spacer or other non-nucleotide modification that binds within 3 bases 5' or 3' of the cleavable RNA domain. The stem domain also comprises 3-20 modified or unmodified DNA residues that are complementary to and will hybridize to the cleavable domain and neighboring bases, including the RNA residue(s). The modified stem domain forms a duplex with the cleavable domain (and neighboring residues, depending on the length of the stem domain). Hybridization of the hairpin blocked-cleavable primer to a target DNA leads to unfolding of the stem, and the primer forms a substrate for RNase H2 at the RNA residue(s), allowing the unblocking reaction to proceed.

In a further embodiment, the stem domain comprises deoxy-inosine or 2' modified inosine residues. The stem domain may comprise any of the other described designs, with substitutions of the bases with deoxy-inosine or 2' modified inosine residues that are complementary to and will hybridize to the cleavable domain and neighboring bases, including the RNA residue(s). The modified stem domain forms a duplex with the cleavable domain (and neighboring residues, depending on the length of the stem domain); however this duplex does not form a substrate for RNase H2. This design allows for modulation of the annealing temperature of the hairpin domain. As described above, hybridization of the hairpin blocked-cleavable primer to a target DNA leads to unfolding of the stem, and the primer forms a substrate for RNase H2 at the RNA residue(s), allowing the unblocking reaction to proceed.

The blocking domain comprises nucleic acid sequence and/or modifier groups at or near the 3'-end of the oligonucleotide which prevents the molecule from serving as a primer for DNA synthesis by DNA polymerase. In one embodiment, this domain is a C3 spacer (propanediol) group positioned at the 3'-end of the oligonucleotide. In another embodiment, this domain is two C3 spacer modifiers position near the 3'-end of the molecule with a final DNA residue comprising the 3'-end of the molecule. In a third embodiment, this domain is one or more bulky groups such as a fluorophore, fluorescent quencher or biotin, and acts as a disruptor of RNase H2 cleavage activity. In a further embodiment, the blocking group contains 2'-O-methyl modified bases at the 3'-end, and in a further embodiment the blocking group contains three 2'-O-methly bases. These bases may be uncomplimentary and serve as a group to block exonuclease digestion.

In a further embodiment, the hairpin primer comprises on or more modifier groups within the stem or blocking domain wherein the modifier groups block extension and/or further limit the cleavage enzyme from cleaving the cleavage domain, and/or limiting degradation of the primer by ssRNases. In a further embodiment, the modifier groups include one or more of biotin, chelators, fluorophores, quenchers or napthyl-azo compounds (see U.S. Pat. No. 8,916,345 incorporated herein in its entirety) such as ZEN™ (Integrated DNA Technologies, Inc.).

In one embodiment, an assay preparation is provided, the preparation comprising a thermostable polymerase, at least one distinct rhPrimer, an RNase H enzyme and a buffer containing the necessary components to support PCR. In a further embodiment, the RNase H enzyme is RNase H2. In yet a further embodiment the enzyme is *Pyrococcus abyssi* RNase H2. In a further embodiment, the enzyme is a chemically inactivated RNase H2, or the enzyme is inactivated using an antibody or aptamer.

In one embodiment the assay preparation for multiplex PCR is provided, the preparation comprising a thermostable polymerase, rhPrimers targeting at least 2 target sites, an RNase H enzyme and a buffer containing the necessary components to support PCR. In a further embodiment, the RNase H enzyme is RNase H2.

In another embodiment, an assay preparation is provided, the preparation comprising a thermostable polymerase, at least two distinct oligonucleotide primers, an RNase H-cleavable probe ("rhProbe"), RNase H enzyme and a buffer. In a further embodiment, the at least one distinct oligonucleotide primer is an rhPrimer. In a further embodiment, the RNase H enzyme is RNase H2.

DETAILED DESCRIPTION OF THE INVENTION

Figure 1:
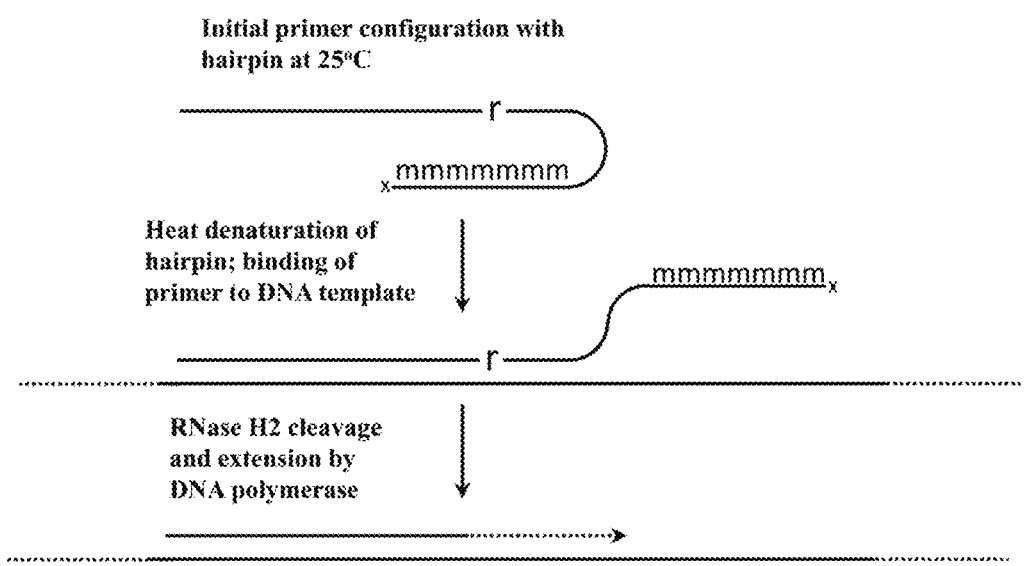
FIG. 1 illustrates the general concept of one embodiment of invention. m=2'-O-methyl residues or DNA, r=RNA, x=blocking group (such as a C3 (propanediol) spacer), and lines represent additional DNA sequence. The loop section of the hairpin may be made of either unpaired nucleotides or non-nucleotide residues such as C3 spacers. 2'-O-methyl residues or DNA may be included to in a length sufficient to provide stable low-temperature hairpin formation and form a duplex structure that is not a substrate for RNase H2 cleavage. The dashed line represents new DNA formed by DNA polymerase following cleavage of the primer in the cleavage domain, removing the terminal blocking group.

The compositions of the present invention represent an improved hairpin version of the blocked-cleavable primer design previously employed in rhPCR. Compared with the original primers, the improved hairpin primers further reduce the formation of primer dimers, increase the specificity and sensitivity of rhPCR, enable more efficient and less error prone method to perform multiplex rhPCR, reduce the risk of RNA-containing primers to be degraded by single-stranded RNases, and improve performance for rare allele detection rhPCR assays.

The blocked-cleavable primer compositions of the present invention have removable hairpin structures that protect the cleavable domain from premature cleavage when the primer is imperfectly hybridized to an off-target nucleic acid sequence, thereby improving specificity. These hairpins are formed by a nucleic acid stem domain located 3'- to the cleavage domain that is separated from the cleavage domain by a loop domain that does not form double-stranded structure in the non-hybridized primer. The cleavage reaction removes all elements 3'- to the cleavage site, resulting in a primer with a 3'-OH group that is unblocked and capable of priming DNA synthesis.

The hairpin blocked cleavable primer comprises 6 contiguous domains which, from 5' to 3', include: (i) a target binding domain; (ii) a discrimination domain; (iii) a cleavable domain; (iv) a loop domain; (v) a stem domain; and (vi) a blocking domain.

The target binding domain is generally complementary to the target nucleic acid and is of sufficient length to provide stable hybridization of the primer to the target nucleic acid under temperature and buffer conditions routinely employed in PCR. Typically the target binding domain is between 15 and 30 nucleic acids in length. In most embodiments, the target binding domain provides for perfect base complementarity to the target nucleic acid; however, in some circumstances polymorphisms may be present in target nucleic acids. Such polymorphisms are common in outbred populations, such as humans. The target binding domain is intended to allow the primer to bind the various polymorphisms that may exist within this sequence in the natural population and thus should have sufficient length and binding affinity to permit binding even in the presence of mismatches that may occur if certain SNPs are present. In other embodiments, this domain may confer added specificity and only hybridize with high efficiency when all bases are perfectly paired with the target nucleic acid. In some embodiments, the hairpin blocked-cleavable primer is intended to provide SNP or allele discrimination. In this case, final specificity is provided by the discrimination domain.

In one embodiment, the discrimination domain is not a separate domain but is merged with the cleavage domain. For example, in embodiments of the invention where the cleavage domain includes a single RNA residue and the cleaving enzyme is RNase H2, the discrimination domain can be the RNA residue. In this embodiment, discrimination is provided by the difference of the rate of cleavage at the RNA residue by RNase H2 when the RNA residue is a match (i.e., is paired with the target) versus when the RNA residue is a mismatch (i.e., not paired with the target). Following cleavage, the remaining primer does not discriminate between the SNP and wild-type target nucleic acid.

In another embodiment, a discrimination domain exists between the target binding domain and the cleavable domain. This domain is typically a single DNA residue which defines the specificity of the primer extension reaction that ensues following removal of all elements 3'- to this residue by the cleavage reaction (i.e., after the cleavage domain has been cleaved and removed). This residue becomes the 3'-end of the primer following cleavage. In the context of a genotyping assay (e.g., a single nucleotide polymorphism (SNP) discrimination assay), this residue corresponds to the SNP under interrogation in the target and base pairs to the SNP present in the target nucleic acid. For example, the base in the discrimination domain may pair with the base present in a mutant form of the target DNA but will not pair (i.e., will be mismatched) to the base present in the wild type form of the target DNA. The presence of a match or mismatch of the residue present in the discrimination domain (at the 3'-end of the active primer following cleavage) with the target nucleic acid will direct specificity of DNA primer extension in PCR. In this embodiment, SNP discrimination is provided at two levels. The first level of discrimination is provided by the cleavage reaction, wherein the cleavage reaction proceeds more slowly when a mismatch is present with the adjacent discrimination domain and a second level of discrimination is provided by the primer extension reaction after cleavage.

In one embodiment DNA synthesis (primer extension) is performed using a wild-type DNA polymerase, such as the DNA polymerase from *Thermus aquaticus* (Taq). In another embodiment, improved SNP discrimination is achieved through use of a mutant DNA polymerase having increased specificity. See Behlke et al., U.S. Patent Application 2015/0191707A1, incorporated herein by reference.

The cleavage domain comprises a site that can be cut by a nuclease enzyme and, optionally, additional sequence which improves the ability of the cleaving enzyme to efficiently utilize the hairpin blocked-cleavable primer as a substrate. One embodiment of the invention employs a single RNA residue as the cleavage site within the cleavage domain and RNase H2 as the cleaving enzyme. In this case, cleavage occurs immediately 5'- to the RNA residue, leaving the target domain+discrimination domain with a terminal 3'-OH, capable of priming DNA synthesis. In a preferred embodiment, the cleaving enzyme is *Pyrococcus abyssi* RNase H2. This enzyme shows maximal cleavage activity if 4 paired DNA residues are 3'-of the RNA residue (see Dobosy et al., BMC Biotechnology 11:e80 2011). In this case, the cleavage domain would be an "rDDDD" sequence, wherein the "r" is at least one RNA base and each "D" represents a DNA base that is complementary to the target nucleic acid. In another embodiment, the cleavage domain is "rDDDDM", wherein the "r" is at least one RNA base, each "D" represents a DNA base complementary to the target, the "M" represents a DNA base mismatched to the target. The cleavage domain can comprise additional matched DNA residues ("rDDDDD", "rDDDDDD", "rDDDDDM", etc.), however the addition of these extra residues does not noticeably improve the activity of the hairpin blocked-cleavable primer to be a substrate for P.a. RNase H2.

The loop domain follows the cleavage domain and serves to connect the cleavage domain to the stem domain. In one embodiment the loop domain contains between 2 and 10 DNA bases, which do not form duplex structure with other elements of the primer (i.e., the loop remains in flexible, single-stranded form). In a further embodiment the loop domain contains between 2 and 6 DNA bases. In a further embodiment the loop domain contains thymidine bases. In yet another embodiment the loop domain comprises synthetic spacer modifiers and no nucleic acid residues. Spacer modifiers are well known to those with skill in the art and include the Spacer C3 (propanediol), Spacer S9 (triethyleneglycol), Spacer S18 (hexaethyleneglycol), dSpacer (abasic ribose), etc. In yet a further embodiment, the loop domain comprises a mixture of DNA residues and spacer modifiers. RNA bases could be used in the loop but they could potentially be degraded with a ssRNase.

The stem domain follows the loop domain and is complementary to all or part of the cleavage domain, discrimination domain, and 3'-portion of the target binding domain. Thus the stem domain hybridizes to those complementary sequences that are located towards the middle of the primer. In one embodiment the stem domain comprises DNA or modified RNA bases. Modifications include 2'-O-alkyl RNA, 2'O-methyl RNA, 2'-F RNA, locked nucleic acids (LNA), or other modifiers which are incompatible with RNase H2 activity.

In one embodiment the stem bases are complementary to one or more bases adjacent to the cleavable RNA base, extending in the 5'-direction, the 3'-direction, or both. In a further embodiment the stem domain comprises 3-20 stem bases that are complementary to and will hybridize to the cleavable domain and neighboring bases, including the RNA residue(s). The stem domain thus forms a duplex with the cleavable domain (and neighboring residues, depending on the length of the stem domain); however this duplex does not form a substrate for RNase H2.

In another embodiment, the stem domain comprises DNA residues. In one embodiment the unmodified DNA bases are complementary to one or more bases adjacent to the cleavable RNA base, extending in the 5'-direction, the 3'-direction, or both. In a further embodiment the stem domain comprises 3-20 unmodified DNA residues that are complementary to and will hybridize to the cleavable domain and neighboring bases, including the RNA residue(s). When the stem comprises DNA residues, the stem may be complementary to the cleavable RNA residues and one or two residues of the specificity domain and/or the target binding domain 5'- to the RNA residues. Longer complementarity on this side of the RNA residues can lead to formation of a substrate for RNase H2. Therefore even in this alternative embodiment the stem domain forms a duplex with the cleavable domain (and neighboring residues, depending on the length of the stem domain); that does not form a substrate for RNase H2. It is unexpected that DNA can serve as the stem's complementary sequence given the presence of RNA in the cleavage domain since a double stranded composition where DNA and RNA are hybridized typically forms a substrate for RNase H cleavage. However the actual results of experiments performed demonstrate that a DNA stem complement to the RNA-containing cleavage domain will not serve as a substrate for RNase H, particularly stems that are only long enough to hybridize over the RNA or 1 to 3 bases further. See FIGS. 10A-E.

Duplex formation with the stem protects the cleavage domain from premature cleavage, with premature cleavage defined as any cleavage event that may occur prior to hybridization of the primer to a target nucleic acid. In the embodiment where the cleavable domain comprises an RNA residue, the stem contains 2'-modified RNA residues, and the cleaving enzyme is RNase H2, the RNA base is protected from cleavage by RNaseH2 when in stem/loop form. Interaction of the cleavage domain with the stem domain protects the cleavage domain from RNase H2 attack from transient weak duplex events that occur in primer-dimer formation and other settings where imperfect duplex formation occurs. Hence the stem prevents premature, unwanted cleavage of the cleavable domain. Hybridization of the hairpin blocked-cleavable primer to a perfect match or near perfect match target DNA molecule leads to disruption of the stem structure, allowing formation of a primer/target duplex that is a substrate for RNase H2 cleavage.

In the embodiment where the cleavable domain comprises an RNA residue, the stem contains DNA residues, and the cleaving enzyme is RNase H2, the RNA base is protected from cleavage by RNaseH2 when in stem/loop form by the length of the hairpin. Without being bound to any particular theory of mechanism, it seems that a lack of efficient contact points between the enzyme and the substrate protects the cleavage domain from RNase H2 attack. This design also protects the cleavage domain from RNase H2 attack from transient weak duplex events that occur in primer-dimer formation and other settings where imperfect duplex formation occurs. Hence the stem prevents premature, unwanted cleavage of the cleavable domain. Hybridization of the hairpin blocked-cleavable primer to a perfect match or near perfect match target DNA molecule leads to disruption of the stem structure, allowing formation of a primer/target duplex that is a substrate for RNase H2 cleavage.

In hairpin configuration, the stem structures described above act as a protecting group for the RNA residue, preventing it from dimerizing and prematurely deblocking in any primer-dimer situation. This hairpin loop also protects the RNA residue from ssRNases, such as RNase I, by generating a double-stranded template which is resistant to ssRNase cleavage.

In one embodiment, the length of the stem domain is designed so that a hairpin forms when the temperature is maintained at approximately 10° C. or more below the annealing temperature of the blocked-cleavage primer to a perfect match DNA target. The hairpin's melting temperature is designed to be low enough to allow it to unfold below the anneal temperature used in the PCR reaction. The actual optimal length of the stem may vary with sequence and chemical composition of the various domains. When the temperature of the reaction mixture is below the annealing temp, the blocked rhPCR primer forms a hairpin structure. As the temperature of the reaction mix is raised sufficiently the hairpin structure relaxes and the primer will anneal to a complementary target. So long as the binding affinity of the primer to target is higher than that of the stem/hairpin, binding of the primer to target will occur even if the stem Tm is above primer annealing temperature employed in the PCR reaction. Once annealed to the target the cleavage domain is recognized by a cleaving agent, more specifically an RNase, and more specifically, for example, an RNase H2. The RNase then cleaves the rhPrimer releasing the fragment containing the hairpin and stem forming region that is 3' of the cleavage domain. The released hairpin and stem region is designed such that it will have a lower annealing temperature than the primer and will not anneal and compete in PCR. The cleaved, unblocked, primer has a free 3' end allowing for extension. Uncleaved hairpin blocked rhPrimers (i.e., those that did not anneal to a target) will fold into a hairpin state making them unsuitable for PCR extension, and protecting from potentially contaminating ssRNases.

The blocking domain comprises nucleic acid sequence and/or modifier groups at or near the 3'-end of the oligonucleotide which prevents the molecule from serving as a primer for DNA synthesis by DNA polymerase. Any group that prevents primer extension can be used. In one embodiment, this domain is a C3 spacer (propanediol) group positioned at the 3'-end of the oligonucleotide. In another embodiment, this domain is two C3 spacer modifiers positioned near the 3'-end of the molecule with a final DNA residue comprising the 3'-end of the molecule. Other blocking groups include a dideoxy base, an inverted dT residue, a fluorescent dye, a fluorescence quencher, biotin or any of the many other modifiers which are well known to those with skill in the art.

The general method is outlined in FIG. 1 which demonstrates the concept of the invention. The loop section of the hairpin may be made of either unpaired nucleotides, nucleotide analogs or abasic residues such as C3 spacers. 2-O-alkyl modifications, such as but not limited to, 2'-O-methyl modified RNA residues may be used to form the complementary stem region of the blocked hairpin rhPCR primer. A person of skill in the art will recognize the factors affecting nucleic acid hybridization and understand that the 2'-O-alkyl modified nucleotides of the stem region may be included to whatever length is required for stable low-temperature hairpin formation preventing RNase H2 cleavage until the primer is suitably hybridized to the target. In contrast, the number of DNA residues in the hairpin domain of the primer must be insufficient to form a substrate for RNase H2. Only when the hairpin blocked rhPCR primer is hybridized to the complementary target nucleic acid will the hairpin unfold, exposing the RNA cleavage site, form a substrate for RNase H2 and the cleavage reaction proceeds. RNase H2 cleavage activates the rhPCR primer by cleaving off the blocking group only when it is bound to the complementary target nucleic acid sequence.

Various embodiments of the present invention provide rhPCR primer constructs that will form folded or hairpin structures under different conditions. FIG. 1. illustrates one embodiment of a hairpin blocked-cleavable primer. Although the hairpin blocked-cleavable primer only shows four modified RNA bases (m), a person having ordinary skill in the art would understand that any number of modified RNA bases could be used and that the optimal configuration may be influenced by sequence context and the annealing temperature employed in the PCR reaction.

In a further embodiment the use of hairpin blocked-cleavable primers would enable higher levels of multiplexing in multiplex PCR. Multiplex PCR uses multiple, unique, primer sets within a single PCR reaction to simultaneously produce PCR amplicons of many different target DNA sequences. However the use of multiple primer sets is problematic due to the formation of primer dimers and off-target amplification from mispriming events. These problems are magnified at higher levels of multiplexing. Because the hairpin forms at temperatures lower than the primer annealing temperature the primers are unavailable for primer dimer or mispriming events. The hairpin formation reduces non-specific interactions enabling higher levels of multiplexing to be performed in a single reaction with fewer unwanted side reactions.

In another embodiment, the invention may utilize a "tail" domain added to the 5' end of the primer, containing a universal probe binding site, and a universal forward primer binding site. This extension would not be complementary to the template of interest, and would allow for inexpensive fluorescent signal detection, which could be multiplexed to allow for multiple color signal detection in qPCR. As conceived, 1-10 cycles of initial cycling and discrimination occurs from both the RNase H2 and the DNA polymerase. After this initial pre-cycling, the highly concentrated and non-discriminatory universal forward primer comes to dominate the amplification, degrading the probe and generating the fluorescent signal when the DNA amplifies. This cycle is repeated 25-50×, allowing for robust detection. This assay design is prone to issues with primer-dimers, and the presence of the blocked-cleavable domain in the primers will suppress or eliminate these issue (for details, see U.S. provisional application 62/339,317).

Other embodiments wherein a blocked primer would be beneficial for selective detection and/or amplification would are also contemplated within the methods of the current invention. For example, a "cycling probe" reaction or "cycling probe technology (CPT)" is an isothermal signal amplification method for the detection of specific target DNA sequences. A chimeric probe DNA-RNA-DNA, and a thermostable RNase H enzyme, are the two main components of this assay. In the presence of a target sequence, a DNA/RNA hybrid is formed and RNase H specifically catalyzes the cleavage of the RNA portion of the hybrid. Since cleaved fragments are small, they dissociate spontaneously from the target sequence at the reaction temperature. The target is then recycled and available for hybridization with another probe; the reaction is inherently cyclic without external manipulations (see, e.g., U.S. Pat. No. 5,403,711, Warnon et al., BioTechniques, 28: 1152-1160 (2000); and Duck et al., BioTechniques, 9: 142-147 (1990)). Unlike PCR, products accumulate in a linear fashion.

"Loop-mediated isothermal amplification" or "LAMP" is an isothermal nucleic acid amplification method that is carried out at a constant temperature and does not require a thermal cycler, in contrast to PCR. In LAMP, a large amount of DNA is synthesized, yielding a large pyrophosphate ion by-product. Pyrophosphate ion combines with divalent metallic ion to form an insoluble salt. Adding manganous ion and calcein, a fluorescent metal indicator, to the reaction solution allows a visualization of substantial alteration of the fluorescence during the one-step amplification reaction, which takes approximately 30-60 minutes (see, e.g., Tomita et al., Nature Protocols, 3: 877-882 (2008)).

The methods described herein can be performed using any suitable RNase H enzyme that is derived or obtained from any organism. Typically, RNase H-dependent PCR reactions are performed using an RNase H enzyme obtained or derived from the hyperthermophilic archaeon *Pyrococcus abyssi* (P.a.), such as RNase H2. Thus, in one embodiment, the RNase H enzyme employed in the methods described herein desirably is obtained or derived from *Pyrococcus abyssi*, preferably an RNase H2 obtained or derived from *Pyrococcus abyssi*. In other embodiments, the RNase H enzyme employed in the methods described herein can be obtained or derived from other species, for example, *Pyrococcus furiosis, Pyrococcus abyssi, Pyrococcus horikoshii, Thermococcus kodakarensis*, or *Thermococcus litoralis*. The invention contemplates naturally occurring enzymes and mutations or fusions thereof.

The hairpin primers prevent undesired cleavage at temperatures where the primer is in hairpin conformation. Therefore non-thermophilic RNase H enzymes could be used. To ensure that the assay is optimal, a thermophilic or hyperthermophilic, enzyme can be used. Alternatively the cleaving enzyme can be reversibly inactivated by chemical modification or by a blocking antibody or aptamer.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention.

"Complement" or "complementary" as used herein means a nucleic acid, and can mean Watson-Crick (e.g., A-T/U and C-G) or Hoogsteen base pairing between nucleotides or nucleotide analogs of nucleic acid molecules.

"Fluorophore" or "fluorescent label" refers to compounds with a fluorescent emission maximum between about 350 and 900 nm. Suitable fluorophores include, for example, 5-FAM (also called 5-carboxyfluorescein, also known as Spiro(isobenzofuran-1(3H), 9'-(9H)xanthene)-5-carboxylic acid, 3',6'-dihydroxy-3-oxo-6-carboxyfluorescein), 5-Hexachloro-Fluorescein, ([4,7,2',4',5',7'-hexachloro-(3',6'-dipivaloyl-fluoresceinyl)-6-carboxylic acid]), 6-Hexachloro-Fluorescein, ([4,7,2',4',5',7'-hexachloro-(3',6'-dipivaloylfluoresceinyl)-5-carb oxylic acid]), 5-Tetrachloro-Fluorescein, ([4,7,2',7'-tetra-chloro-(3',6'-dipivaloylfluoresceinyl)-5-carboxylic acid]), 6-Tetrachloro-Fluorescein, ([4,7,2',7'-tetrachloro-(3',6'-dipivaloylfluoresceinyl)-6-carb oxylic acid]), 5-TAMRA (5-carboxytetramethylrhodamine); Xanthylium, 9-(2,4-dicarboxyphenyl)-3,6-bis(dimethyl-amino), 6-TAMRA (6-carboxytetramethylrhodamine), 9-(2,5-dicarboxyphenyl)-3,6-bis(dimethyl amino), EDANS (5-((2-aminoethyl)amino)naphthalene-1-sulfonic acid), 1,5-IAEDANS (5-((((2-iodoacetyl)amino)ethyl)amino)naphthalene-1-sulfonic acid), Cy5 (Indodicarbocyanine-5); Cy3 (Indo-dicarbocyanine-3), and BODIPY FL (2,6-dibromo-4,4-difluoro-5,7-dimethyl-4-bora-3a,4a-diaza-s-indacene-3-proprionic acid), Quasar®-670 dye (Biosearch Technologies), Cal Fluor® Orange dye (Biosearch Technologies), Rox dyes, ATTO dyes (Atto-Tec), Max dyes (Integrated DNA Technologies), and derivatives thereof.

"Hybridization," as used herein, refers to the formation of a duplex structure by two single-stranded nucleic acids due to complementary base pairing. Hybridization can occur between fully complementary nucleic acid strands or between "substantially complementary" nucleic acid strands that contain minor regions of mismatch.

The terms "nucleic acid" or "oligonucleotide" as used herein, refer to at least two nucleotides covalently linked together. The depiction of a single strand also defines the sequence of the complementary strand. Thus, a nucleic acid also encompasses the complementary strand of a depicted single strand. Many variants of a nucleic acid can be used for the same purpose as a given nucleic acid. Thus, a nucleic acid also encompasses substantially identical nucleic acids and complements thereof.

"Non-nucleic acid linker modifiers", "modifiers" and "modifications" are used with the application, and refer to non-natural compositions that can be added to an oligonucleotide. There are hundreds of modifications known in the art, with each having one or more beneficial purposes. Spacers, stability-enhancing and other $T_m$-modulating modifications, labeling, quenching and tagging modifications are all contemplated within this genus.

"Polymerase Chain Reaction (PCR)" refers to the enzymatic reaction in which DNA fragments are synthesized and amplified from a substrate DNA in vitro. Although many variations are known in the art, the conventional reaction involves the use of two synthetic oligonucleotide primers which are complementary to nucleotide sequences in the substrate DNA which are separated by a short distance of a few hundred to a few thousand base pairs, and the use of a thermostable DNA polymerase. The chain reaction consists of a series of 10 to 40 cycles. In each cycle, the substrate DNA is first denatured at high temperature. After cooling down, synthetic primers which are present in vast excess, hybridize to the substrate DNA to form double-stranded structures along complementary nucleotide sequences. The primer-substrate DNA complexes will then serve as initiation sites for a DNA synthesis reaction catalyzed by a DNA polymerase, resulting in the synthesis of a new DNA strand complementary to the substrate DNA strand. The synthesis process is repeated with each additional cycle, creating an amplified product of the substrate DNA.

"Quencher" refers to a molecule or part of a compound, which is capable of reducing the emission from a fluorescent donor when attached to or in proximity to the donor. Quenching may occur by any of several mechanisms including fluorescence resonance energy transfer, photo-induced electron transfer, paramagnetic enhancement of intersystem crossing, Dexter exchange coupling, and exciton coupling such as the formation of dark complexes. Any suitable quencher can be used in the invention, such as, for example, DABCYL, BLACK HOLE™ Quenchers (such as, BHQ-1®, BHQ-2®, and BHQ-3®), IOWA BLACK® FQ, and IOWA BLACK® RQ, ZEN™ (Integrated DNA Technologies, Inc.) all of which are commercially available from a variety of sources. During amplification of the target nucleic acid by DNA polymerase, the fluorophore and/or quencher can be cleaved and separated, allowing the detection of the fluorophore signal. The fluorescence intensity is proportional to the amount of amplified product and allows for quantification of a target nucleic acid.

The following examples further illustrate the invention but should not be construed as in any way limiting the invention's scope.

Example 1

This example demonstrates an enhanced rhPCR assay that utilizes hairpin blocked-cleavable primers.

To demonstrate the utility of the new hairpin blocked-cleavable primers, hairpin blocked-cleavable primers, standard blocked-cleavable primers and unblocked primers were designed against SNP rs113488022, the V600E mutation in the human BRAF gene. The hairpin blocked-cleavable primers contained either a loop of four thymidine residues or two thymidine residues. The hairpin blocked-cleavable primers also contained either four 2'-O-Methyl complementary RNAs, five 2'-O-Methyl Complementary RNAs, or 6 2'-O-Methyl complementary RNAs. These primers were tested in PCR and rhPCR with the H784Q mutant Taq polymerase.

TABLE 1

Sequence of oligonucleotides employed in SNP discrimination assay described in Example 1.

| Sequence Name | Sequence | SEQ ID No. |
|---|---|---|
| Forward non-discriminatory primer | GCTGTGATTTTGGTCTAGCTACAG | SEQ ID NO: 1 |
| Reverse unblocked primer | GCCCTCAATTCTTACCATCCACAAA | SEQ ID NO: 2 |
| Probe | FAM-TCCCATCAG-ZEN-TTTGACAGTTGTCTGGA-IBFQ | SEQ ID NO: 3 |
| rs113488022 Forward 4dmx | GCTGTGATTTTGGTCTAGCTACAGTrGAAATG-x | SEQ ID NO: 4 |
| rs113488022 Forward 4t4m | GCTGTGATTTTGGTCTAGCTACAGTrGAAATTTTTmUmUmCmA-x | SEQ ID NO: 5 |
| rs113488022 Forward 4t5m | GCTGTGATTTTGGTCTAGCTACAGTrGAAATTTTTmUmUmCmAmC-x | SEQ ID NO: 6 |
| rs113488022 Forward 4t6m | GCTGTGATTTTGGTCTAGCTACAGTrGAAATTTTTmUmUmCmAmCmU-x | SEQ ID NO: 7 |
| rs113488022 Forward 2t4m | GCTGTGATTTTGGTCTAGCTACAGTrGAAATTTmUmUmCmA-x | SEQ ID NO: 8 |
| rs113488022 Forward 2t5m | GCTGTGATTTTGGTCTAGCTACAGTrGAAATTTmUmUmCmAmC-x | SEQ ID NO: 9 |
| rs113488022 Forward 2t6m | GCTGTGATITTGGICTAGCTACAGTrGAAATTTmUmUmCmAmCmU-x | SEQ ID NO: 10 |
| Reverse rhPrimer | GCCCTCAATTCTTACCATCCACAAArATGGAA-x | SEQ ID NO: 11 |

TABLE 1-continued

Sequence of oligonucleotides employed in SNP discrimination assay described in Example 1.

| Sequence Name | Sequence | SEQ ID No. |
|---|---|---|
| T-amplicon | GCGTGATTTTGGTCTAGCTACAGTGAAATCTCGATGGAGTGGGTCCCATCAGTTTGAACAGTTGTCTGGATCCATTTTGTGGATGGTAAGAATTGAGGGC | SEQ ID NO: 12 |
| A-amplicon | GCGTGATTTTGGTCTAGCTACAGAGAAATCTCGATGGAGTGGGTCCCATCAGTTTGAACAGTTGTCTGGATCCATTTTGTGGATGGTAAGAATTGAGGGC | SEQ ID NO: 13 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa, x=C3 propanediol spacer block, mA=2'-O-Methyl Adenine RNA, mU=2'O-Methyl Uracil RNA, mC=2'-O-Methyl Cytosine RNA, mG=2'-O-Methyl Guanosine RNA, rG=Guanosine RNA, rA=Adenine RNA.

10 uL reaction volumes were used in these assays. To perform the reaction, 5 uL of 2×IDT (IDT, Coralville, Iowa) Prime-time gene expression master mix (1× final, containing dNTPS, Taq B, stabilizers, and $MgCl_2$), or 5 uL of 2×V1 Genie RN2 Master Mix (IDT, Coralville, Iowa) (containing dNTPS, H784Q mutant polymerase, stabilizers, and $MgCl_2$) was combined with 500 nM (5 pmol) of either of the allelic primers, 250 nM (2.5 pmol) of the probe, as well as 500 nM (5 pmol) of the reverse primer were also added. Additionally, 7.5 mU (13.6 fmol; 1.36 nM) of P.a. RNase H2 (*Pyrococcus abyssi* RNase H2) and 1000 copies of either amplicon (present as a double-stranded gBlock™ template; SEQ ID Nos. 12-13) were added to the reaction mix. The reaction was thermocycled on a CFX384™ Real-time system (Bio-Rad™ Hercules, Calif.). Cycling conditions were as follows: $95^{3:00}$–$(95^{0:10}$–$65^{0:45})$×60. Each reaction was performed in triplicate.

Cq and delta Cq results of the experiment are shown in Table 2. The SEQ ID NO: for the forward primer in each reaction is shown in the third column. The data show that the mismatch discrimination of the assays system is increased when using a highly discriminatory mutant Taq polymerase (H784Q) as compared to a wild type Taq polymerase, and that the hairpin-blocked primer design is functional in both systems.

TABLE 2

Cq and delta Cq values obtained from the experiment described in Example 1.

| | Seq. Name | SEQ ID No. | T-amplicon | A-amplicon | ΔCq | NTC |
|---|---|---|---|---|---|---|
| V1 Genie | Non-discr | SEQ ID NO: 1 | 29.0 | 29.2 | | >60 |
| RN2 | 4Dmx | SEQ ID NO: 4 | 29.7 | 39.2 | 9.5 | >60 |
| master mix | 4t4m | SEQ ID NO: 5 | 30.3 | 40.1 | 9.8 | >60 |
| (H784Q | 4t5m | SEQ ID NO: 6 | 31.4 | 42.0 | 10.6 | >60 |
| pol) | 4t6m | SEQ ID NO: 7 | 31.5 | 42.4 | 10.9 | >60 |
| | 2t4m | SEQ ID NO: 8 | 30.4 | 40.5 | 10.1 | >60 |
| | 2t5m | SEQ ID NO: 9 | 31.1 | 40.8 | 9.7 | >60 |
| | 2t6m | SEQ ID NO: 10 | 30.5 | 40.2 | 9.7 | >60 |
| Prime-time | Non-discr | SEQ ID NO: 1 | 28.3 | 27.7 | | >60 |
| Gene | 4Dmx | SEQ ID NO: 4 | 29.0 | 30.5 | 1.5 | >60 |
| expression | 4t4m | SEQ ID NO: 5 | 30.1 | 31.9 | 1.8 | >60 |
| Master mix | 4t5m | SEQ ID NO: 6 | 30.4 | 32.6 | 2.2 | >60 |
| (WT Taq pol | 4t6m | SEQ ID NO: 7 | 30.2 | 32.5 | 2.3 | >60 |
| | 2t4m | SEQ ID NO: 8 | 29.8 | 32.1 | 2.2 | >60 |
| | 2t5m | SEQ ID NO: 9 | 30.4 | 32.8 | 2.5 | >60 |
| | 2t6m | SEQ ID NO: 10 | 30.3 | 32.7 | 2.5 | >60 |

Example 2

This example demonstrates the effect on Cq of hairpin block rhPCR primers having longer extension regions.

To demonstrate the effect of blocked hairpin rhPCR primers having longer extension (stem regions), additional rhPCR primers and unblocked primers were designed against rs113488022, the V600E mutation in the human BRAF gene. The hairpin blocked-cleavable primers contained either eight 2'-O-Methyl complementary RNAs, nine 2'-O-Methyl complementary RNAs, or ten 2'-O-Methyl complementary RNAs. These primers were tested in PCR and rhPCR with TaqB or H784Q mutant Taq polymerase.

TABLE 3

Sequence of oligonucleotides employed in SNP discrimination assay described in Example 2.

| Sequence Name | Sequence | SEQ ID NO. |
|---|---|---|
| Forward non-discriminatory primer | GCTGTGATTTTGGTCTAGCTACAG | SEQ ID NO. 1 |
| Reverse unblocked primer | GCCCTCAATTCTTACCATCCACAAA | SEQ ID NO. 2 |
| Probe | FAM-TCCCATCAG-ZEN-TTTGAACAGTTGTCTGGA-IBFQ | SEQ ID NO. 3 |
| rs113488022 Forward 4dmx | GCTGTGATTTTGGTCTAGCTACAGGTrGAAATG-x | SEQ ID NO. 4 |
| rs113488022 Forward 4t8m | GCTGTGATTTTGGTCTAGCTACAGGTrGAAATTTTTmAmUmUmUmCmAmCmU-x | SEQ ID NO. 14 |
| rs113488022 Forward 4t9m | GCTGTGATTTTGGTCTAGCTACAGGTrGAAATTTTTmAmUmUmUmCmAmCmUmG-x | SEQ ID NO. 15 |
| rs113488022 Forward 4t10m | GCTGTGATTTTGGTCTAGCTACAGGTrGAAATTTTTmAmUmUmUmCmAmCmUmGmU-x | SEQ ID NO. 16 |
| Reverse rhPrimer | GCCCTCAATTCTTACCATCCACAAArATGGAA-x | SEQ ID NO. 11 |
| T-amplicon | GCGTGATTTTGGTCTAGCTACAGTGAAATCTCGATGGAGTGGGTCCCATCAGTTTGAACAGTTGTCTGGATCCATTTTGTGGATGGTAAGAATTGAGGGC | SEQ ID No. 12 |
| A-amplicon | GCGTGATTTTGGTCTAGCTACAGAGAAATCTCGATGGAGTGGGTCCCATCAGTTTGAACAGTTGTCTGGATCCATTTTGTGGATGGTAAGAATTGAGGGC | SEQ ID No. 13 |

Nucleic acid sequences are shown 5'-3'. ZEN=internal ZEN™ quencher (IDT, Coralville, Iowa). Location of potential mismatch is underlined. FAM=6-carboxyfluorescein, IBFQ=Iowa Black® FQ (fluorescence quencher, IDT, Coralville, Iowa, x=C3 propanediol spacer block, mA=2'-O-Methyl Adenine RNA, mU=2'O-Methyl Uracil RNA, mC=2'-O-Methyl Cytosine RNA, mG=2'-O-Methyl Guanosine RNA, rG=Guanosine RNA, rA=Adenine RNA.

Each assay was performed as follows: 10 uL reaction volumes were used in these assays. To perform the reaction, 5 uL of 2×V2.2 Genie RN2 Master Mix (IDT, Coralville, Iowa) (1× final, containing dNTPS, H784Q mutant polymerase, stabilizers, and MgCl$_2$) was combined with 500 nM (5 pmol) of forward primer, 250 nM (2.5 pmol) of the probe, as well as 500 nM (5 pmol) of the reverse primer was also added. Additionally, 7.5 mU (13.6 fmol; 1.36 nM) of P.a. RNase H2 (*Pyrococcus abyssi* RNase H2) and 1000 copies of each template (present as a double-stranded gBlock™ template; SEQ ID Nos. 12 or 13) were added to the reaction mix. The reaction was thermocycled on a CFX384™ Real-time system (Bio-Rad™, Hercules, Calif.). Cycling conditions were as follows: $95^{3:00}-(95^{0:10}-65^{0:45})\times55$. Each reaction was performed in triplicate.

Cq and ΔCq Results of the experiment are shown in Table 4. The SEQ ID NO: for the forward primer used in each reaction is given in column 2 of this table. This data shows that the use of hairpin blocked-cleavable primers improves the mismatch discrimination of the assay over both unblocked primers and 4Dmx non-hairpin primers.

TABLE 4

Cq values from the qPCR experiment described in Example 2.

| Seq. Name | SEQ ID NO: | T-amplicon | A-amplicon | ΔCq | NTC |
|---|---|---|---|---|---|
| Non-discrim | 1 | 28.9 | 28.9 | | >55 |
| 4Dmx | 4 | 30.1 | 42.9 | 12.8 | >55 |
| 4t8m | 14 | 33.7 | 48.0 | 14.3 | >55 |
| 4t9m | 15 | 31.2 | 47.1 | 16.0 | >55 |
| 4t10m | 16 | 31.6 | 47.4 | 15.9 | >55 |

Example 3

This example demonstrates the activity of the hairpin blocked-cleavable primers in a temperature gradient.

To determine effective annealing temperatures for hairpin blocked-cleavable primers the hairpin blocked-cleavable primers were subjected to a temperature gradient during PCR. Hairpin blocked-cleavable primers, rhPCR primers and unblocked primers were designed against rs113488022, the V600E mutation in the human BRAF gene. The hairpin blocked-cleavable primers contained either eight 2'-O-Methyl complementary RNAs, nine 2'-O-Methyl complementary RNAs, or ten 2'-O-Methyl complementary RNAs. These primers were tested in PCR and rhPCR with H784Q mutant Taq polymerase.

TABLE 5

Sequence of oligonucleotides employed in SNP discrimination assay described in Example 3.

| Sequence Name | Sequence | SEQ ID NO: |
|---|---|---|
| Forward non-discriminatory primer | GCTGTGATTTTGGTCTAGCTACAG | SEQ ID NO: 1 |
| Reverse unblocked primer | GCCCTCAATTCTTACCATCCACAAA | SEQ ID NO: 2 |
| Probe | FAM-TCCCATCAG-ZEN-TTTGACAGTTGTCTGGA-IBFQ | SEQ ID NO: 3 |
| rs113488022 Forward 4dmx | GCTGTGATTTTGGTCTAGCTACAGGTrGAAATG-x | SEQ ID NO: 4 |
| rs113488022 Forward 4t9m | GCTGTGATTTTGGTCTAGCTACAGGTrGAAATTTTTmAmUmUmUmCmAmCmUmG-x | SEQ ID NO: 15 |
| rs113488022 Forward 4f10m | GCTGTGATTTTGGTCTAGCTACAGGTrGAAATTTTTmAmUmUmUmCmAmCmUmGmU-x | SEQ ID NO: 16 |
| Reverse rhPrimer | GCCCTCAATTCTTACCATCCACAAArATGGAA-x | SEQ ID NO: 11 |
| T-amplicon | GCGTGATTTTGGTCTAGCTACAGTGAAATCTCGATGGAGTGGGTCCCATCAGTTTGAACAGTTGTCTGGATCCATTTTGTGGATGGTAAGAATTGAGGGC | SEQ ID NO: 12 |
| A-amplicon | GCGTGATTTTGGTCTAGCTACAGAGAAATCTCGATGGAGTGGGTCCCATCAGTTTGAACAGTTGTCTGGATCCATTTTGTGGATGGTAAGAATTGAGGGC | SEQ ID NO: 13 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa, x=C3 propanediol spacer block, mA=2'-O-Methyl Adenine RNA, mU=2'O-Methyl Uracil RNA, mC=2'-O-Methyl Cytosine RNA, mG=2'-O-Methyl Guanosine RNA, rG=Guanosine RNA, rA=Adenine RNA.

10 uL reaction volumes were used in these assays. To perform the reaction, 5 uL of 2×V2.2 Genie RN2 Master Mix (IDT, Coralville, Iowa) (1× final, containing dNTPS, H784Q mutant polymerase, stabilizers, and $MgCl_2$) was combined with 500 nM (5 pmol) of forward primer, 250 nM (2.5 pmol) of the probe, as well as 500 nM (5 pmol) of the reverse primer were also added. Additionally, 7.5 mU (13.6 fmol; 1.36 nM) of P.a. RNase H2 (*Pyrococcus abyssi* RNase H2) and 1000 copies of each template (present as a double-stranded gBlock™ template; SEQ ID Nos. 12 or 13) were added to the reaction mix. The reaction was thermocycled on a CFX384™ Real-time system (Bio-Rad™, Hercules, Calif.). Cycling conditions were as follows: $95^{3:00}$–($95^{0:10}$–$65^{0:45}$)×55. Each reaction was performed in triplicate.

Cq and ΔCq Results of the experiment are shown in Table 6. The annealing temperatures are shown in the first column of the table. The SEQ ID NO: of the forward primers used is shown below the primer name. The data show that the hairpin blocked-cleavable primers improve mismatch discrimination across a wide range of annealing temperatures. Additionally the results show that the mismatch discrimination of hairpin blocked-cleavable primers is improved as compared to unblocked primers at elevated temperatures.

TABLE 6

Cq values obtained from the experiment in Example 3.

| | Non-discrim SEQ ID NO: 1 | | 4Dm-x control SEQ ID NO: 4 | | | 4t9m SEQ ID NO: 15 | | | 4t10m SEQ ID NO: 16 | | |
|---|---|---|---|---|---|---|---|---|---|---|---|
| Temp | T | A | T | A | ΔCq | T | A | ΔCq | T | A | ΔCq |
| 65.0° C. | 30.2 | 31.3 | 41.1 | >60 | >18.9 | 39.2 | >60 | | 45.0 | >60 | |
| 64.8° C. | 30.2 | 31.1 | 39.3 | >60 | >20.8 | 38.0 | >60 | | 22.0 | 42.3 | >60 | 17.7 |
| 64.5° C. | 29.6 | 30.3 | 36.3 | >60 | >23.7 | 35.6 | >60 | | 24.4 | 39.2 | >60 | 20.8 |
| 64.1° C. | 29.4 | 30.1 | 34.1 | >60 | >25.9 | 34.1 | >60 | | 25.9 | 36.2 | >60 | 23.8 |
| 63.4° C. | 29.0 | 29.7 | 32.4 | >60 | >27.6 | 32.1 | >60 | | 27.9 | 34.1 | >60 | 25.9 |
| 62.7° C. | 29.0 | 29.6 | 31.2 | 55.0 | 23.8 | 31.7 | 53.3 | 21.5 | 32.4 | >60 | 27.6 |
| 61.6° C. | 28.9 | 29.2 | 30.8 | 49.3 | 18.5 | 31.0 | 50.8 | 19.9 | 31.5 | 53.1 | 21.6 |

TABLE 6-continued

Cq values obtained from the experiment in Example 3.

| Temp | Non-discrim SEQ ID NO: 1 | | 4Dm-x control SEQ ID NO: 4 | | | 4t9m SEQ ID NO: 15 | | | 4t10m SEQ ID NO: 16 | | |
|---|---|---|---|---|---|---|---|---|---|---|---|
| | T | A | T | A | ΔCq | T | A | ΔCq | T | A | ΔCq |
| 60.6° C. | 29.0 | 29.3 | 30.6 | 44.5 | 13.9 | 31.2 | 49.9 | 18.7 | 31.4 | 46.9 | 15.4 |
| 59.4° C. | 29.2 | 29.3 | 31.1 | 40.9 | 9.9 | 31.2 | 43.7 | 12.6 | 31.5 | 43.5 | 12.0 |
| 58.4° C. | 29.5 | 29.8 | 31.3 | 39.3 | 8.0 | 32.0 | 43.9 | 11.9 | 32.3 | 41.8 | 9.5 |
| 57.5° C. | 29.6 | 29.8 | 31.5 | 38.5 | 7.0 | 32.0 | 40.8 | 8.9 | 32.5 | 40.9 | 8.4 |
| 56.8° C. | 29.9 | 30.0 | 32.0 | 38.6 | 6.6 | 32.8 | 42.2 | 9.4 | 32.9 | 41.0 | 8.1 |
| 56.1° C. | 29.7 | 29.9 | 31.4 | 38.8 | 7.4 | 32.2 | 40.3 | 8.1 | 32.5 | 39.9 | 7.5 |
| 55.6° C. | 30.0 | 30.3 | 31.8 | 38.6 | 6.8 | 32.7 | 41.2 | 8.6 | 33.0 | 40.0 | 7.0 |
| 55.2° C. | 30.2 | 30.0 | 31.7 | 38.8 | 7.1 | 32.3 | 40.7 | 8.4 | 32.7 | 39.9 | 7.2 |
| 55.0° C. | 30.1 | 30.3 | 32.2 | 38.7 | 6.5 | 32.5 | 40.8 | 8.2 | 32.7 | 40.0 | 7.3 |

Example 4

This example demonstrates the enhanced stability of hairpin blocker rhPCR primers in the presence of single stranded RNases, such as RNase I.

To demonstrate the stability of hairpin blocker rhPCR primers, rhPCR primers and hairpin blocker rhPCR primers were incubated with and without RNase I. Hairpin blocker rhPCR primer designs had the following sequences on the 3' end of the blocked rhPrimer: 1) four 2'-O-Methyl RNA bases and a four thymidine base loop; 2) five 2'-O-Methyl RNA bases and a four thymidine base loop; 3) six 2'-O-Methyl RNA bases and a four thymidine base loop; 4) four 2'-O-Methyl RNA bases and a two thymidine base loop; 5) five 2'-O-Methyl RNA bases and a two thymidine base loop; or 6) six 2'-O-Methyl RNA bases and a two thymidine base loop. The rhPrimer consisted of four template matching DNA bases, a single mismatch DNA base, and a blocker, such as a C3 spacer.

10 uL reaction volumes were used in these assays. Either 50 pmol hairpin blocked rhPCR primer, 50 pmol AS or water, NEB buffer 3 and 100 U RNase I or 50 pmol hairpin blocked rhPCR primer, 50 pmol AS or water, NEB buffer 3 and no RNase I were incubated at room temperature for 30 mins. The reaction products were then run in 15% denaturing acrylamide gel and visualized.

Figure 2:
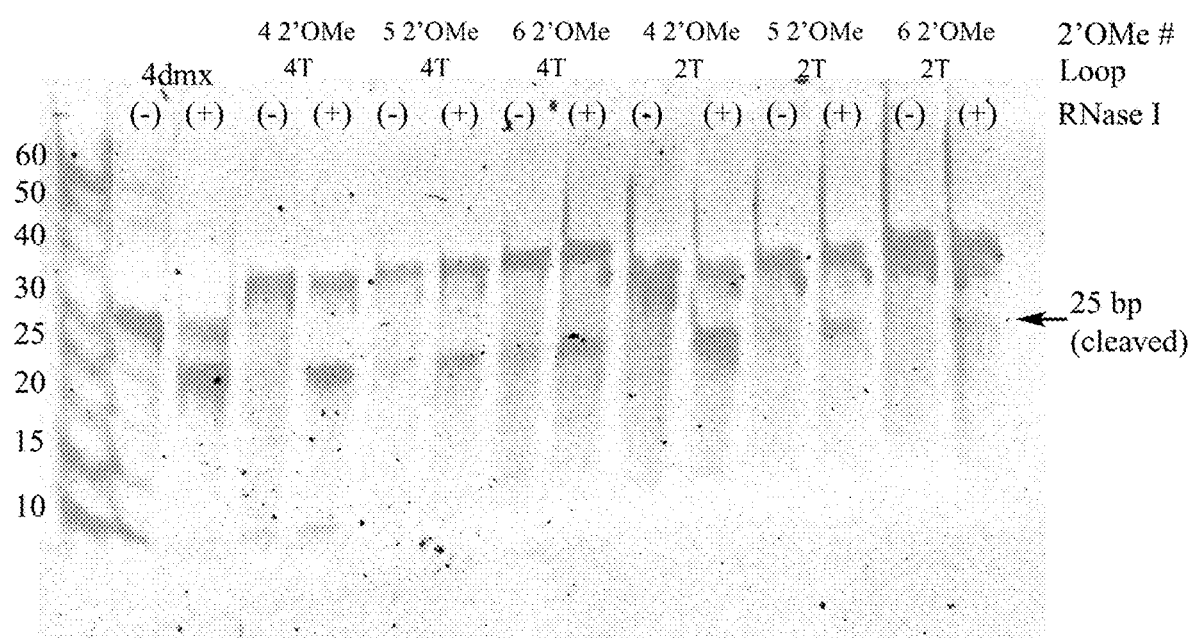
FIG. 2 is a gel image showing reduced cleavage of rhPrimers when incubated with a single stranded RNase, such as, for example, RNase I. The 4dmx primers are traditional rhPCR primers having four matching DNA bases (4d), a single mismatch base (m) and a blocking moiety (x), such as a C3 spacer at the primers 3' end. 4dmx primers do not form a hairpin loop or contain 2'O-Methyl modified ribonucleotides. The hairpin blocker rhPCR primers (rhPrimers) may contain varying lengths of 2'-O-Methyl RNA bases and varying loop lengths.
Figure 3A:
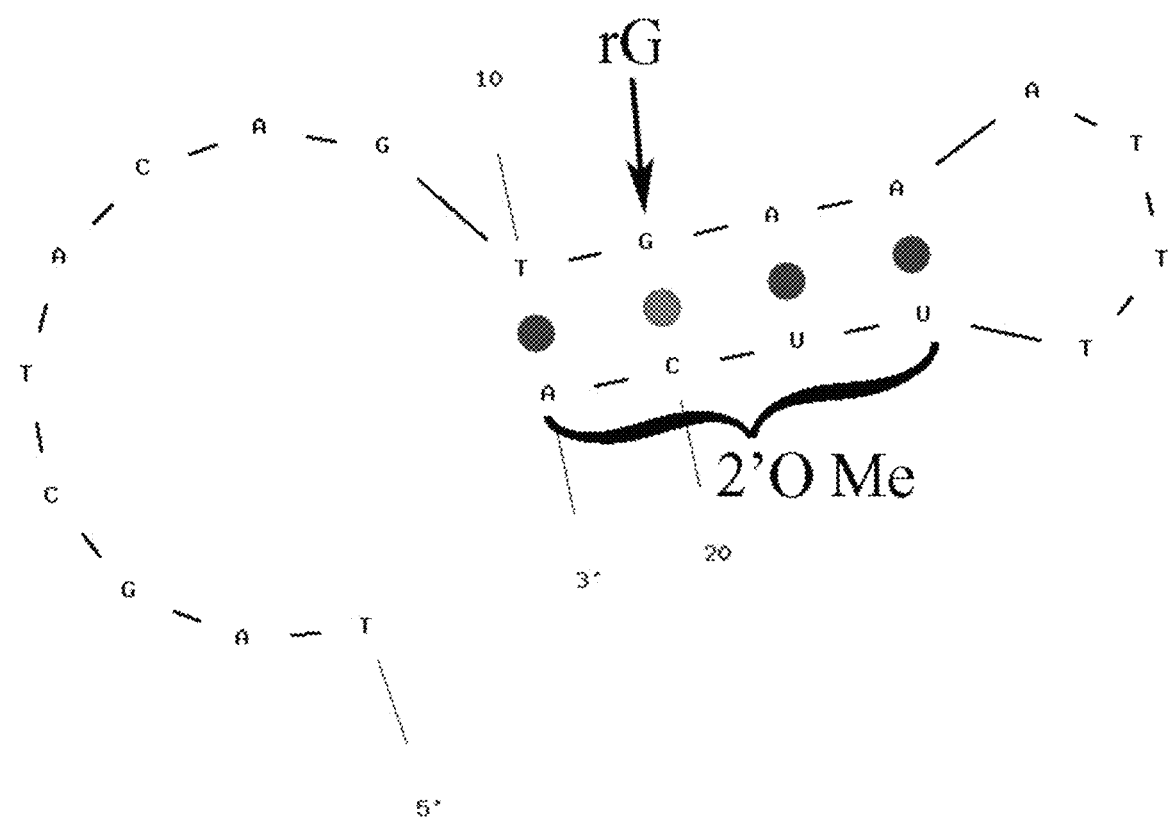
FIG. 3 (A-C) are representations of the hairpin region of hairpin blocked-cleavable primers designed to SNP rs113488022. The hairpin consists of two thymidine residues and 4 (FIG. 3A), 5 (FIG. 3B), or 6 (FIG. 3C) 2'-O-methyl RNA bases that form the stem region. rG is the ribonucleotide base which forms the cleavage domain and is the site of cleavage by RNase H2 when the rhPCR primer is bound to a complementary target. When the rhPCR primer is hybridized to a complementary target the RNase H will cleave 5' of the cleavage domain ribonucleotide base activating the primer.
Figure 3B:
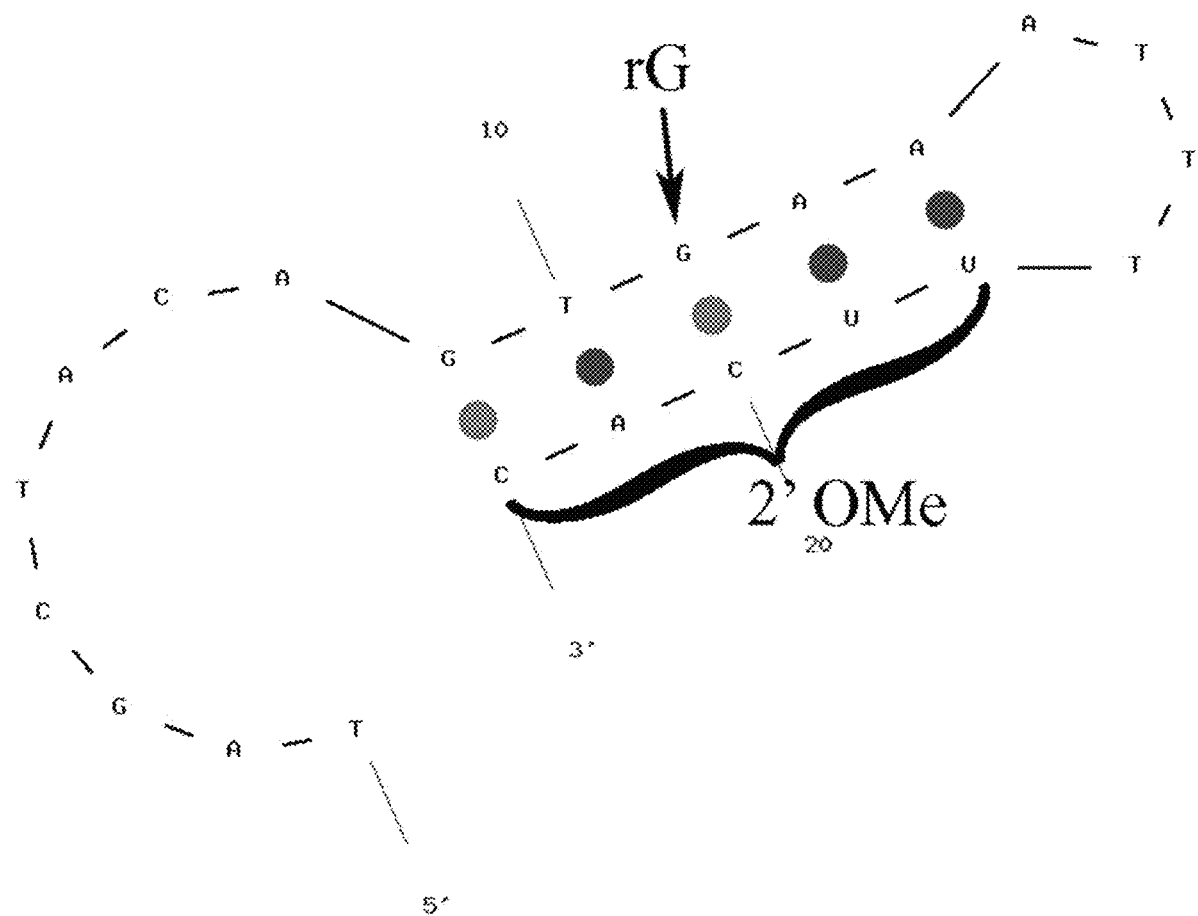
Figure 3C:
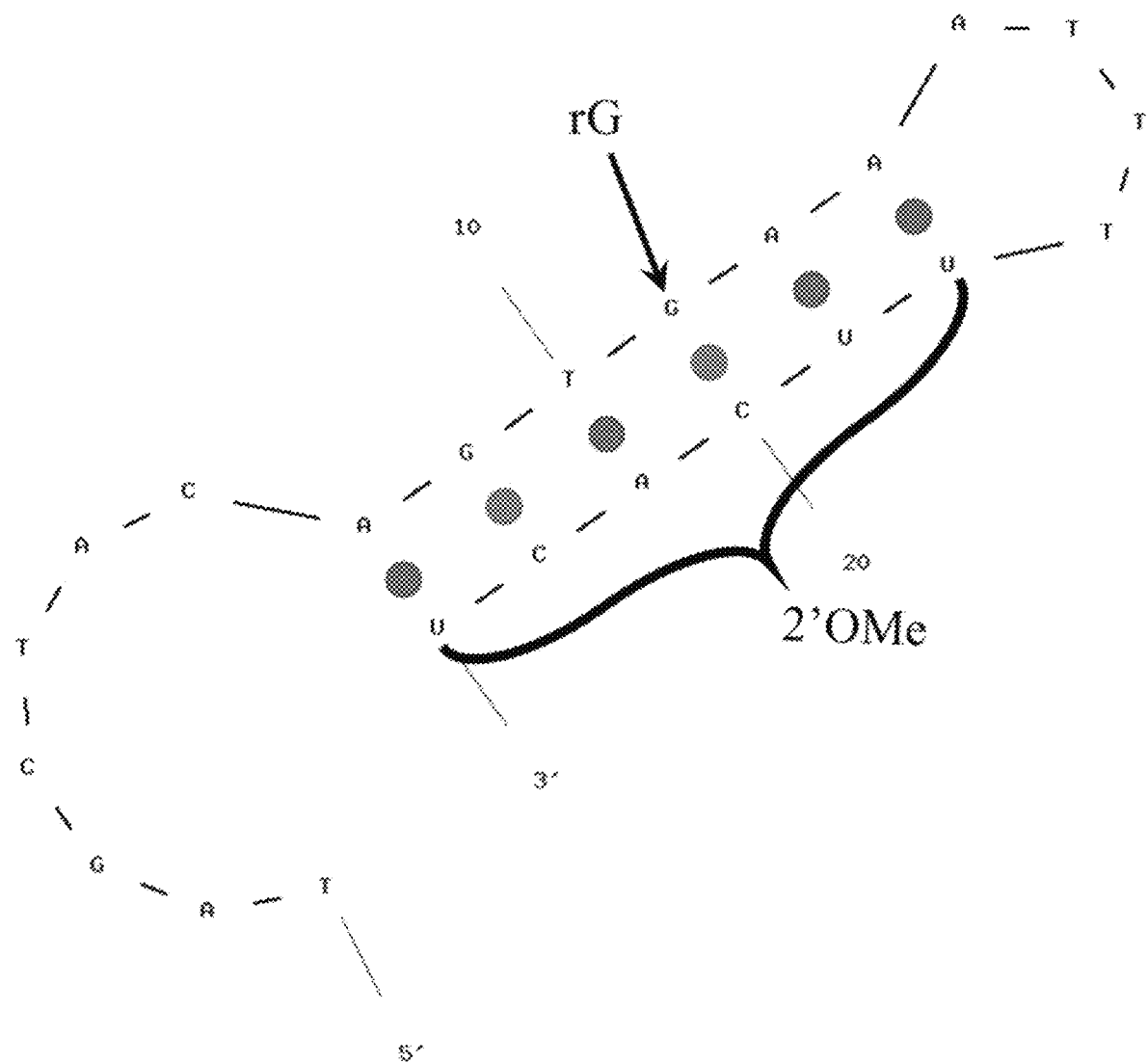
Figure 4A:
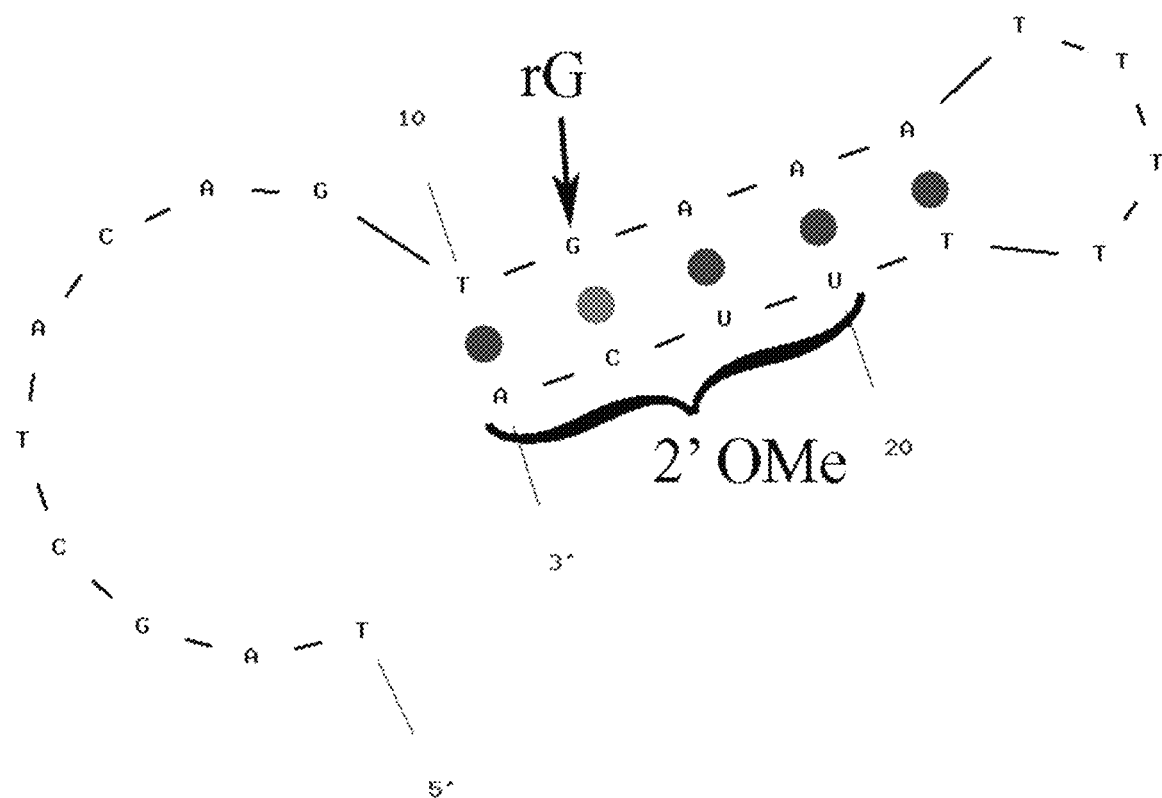
FIG. 4 (A-C) are representations of the hairpin region of hairpin blocked-cleavable primers designed to SNP rs113488022. The hairpin consists of four thymidine residues and 4 (FIG. 4A), 5 (FIG. 4B), or 6 (FIG. 4C) 2'-O-methyl RNA bases that form the stem region. rG is the ribonucleotide base which is targeted by RNase H for cleavage when the rhPCR primer is bound to a complementary target. When the rhPCR primer is hybridized to the complementary target the RNase H will cleave 5' of the ribonucleotide base, activating the primer.
Figure 4B:
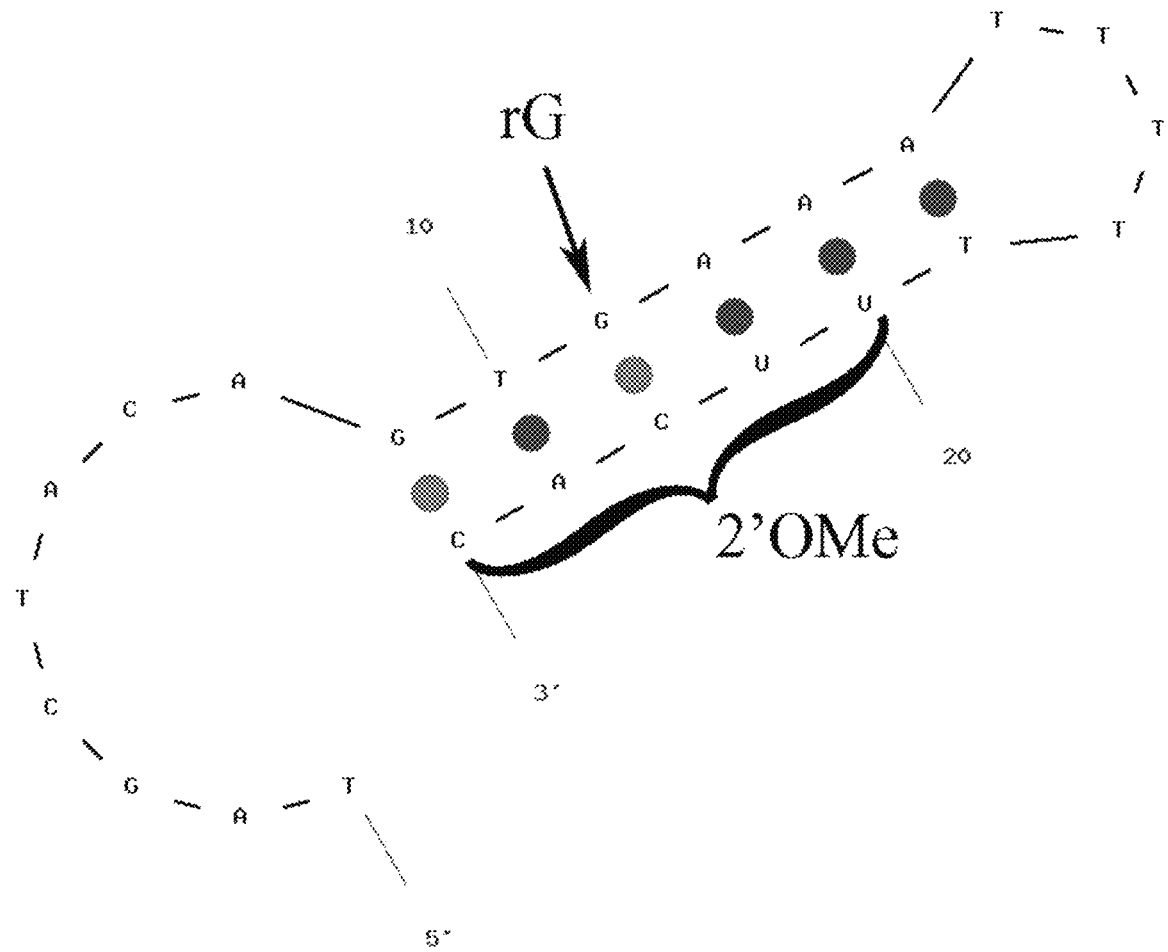
Figure 4C:
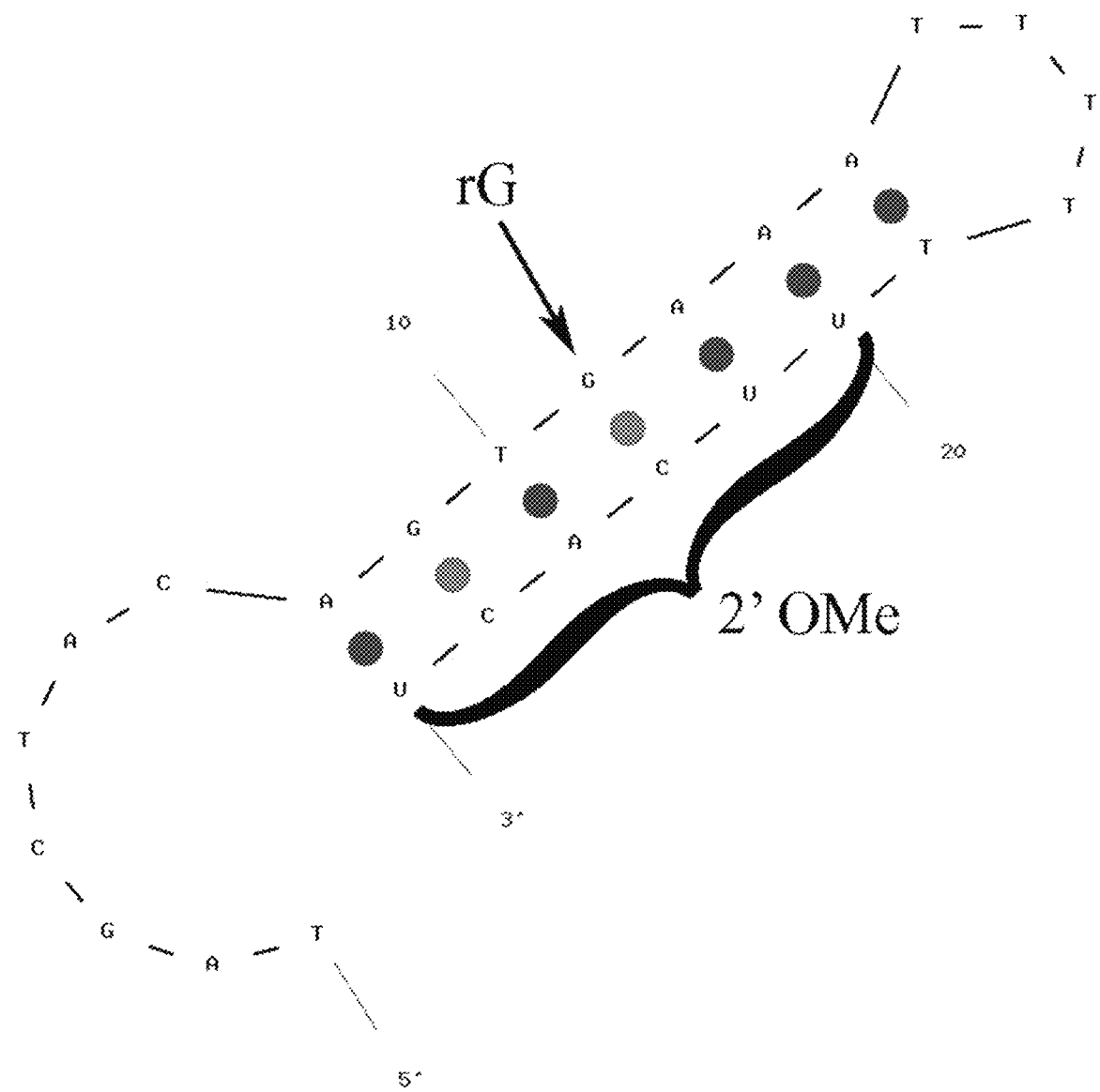
Figure 5A:
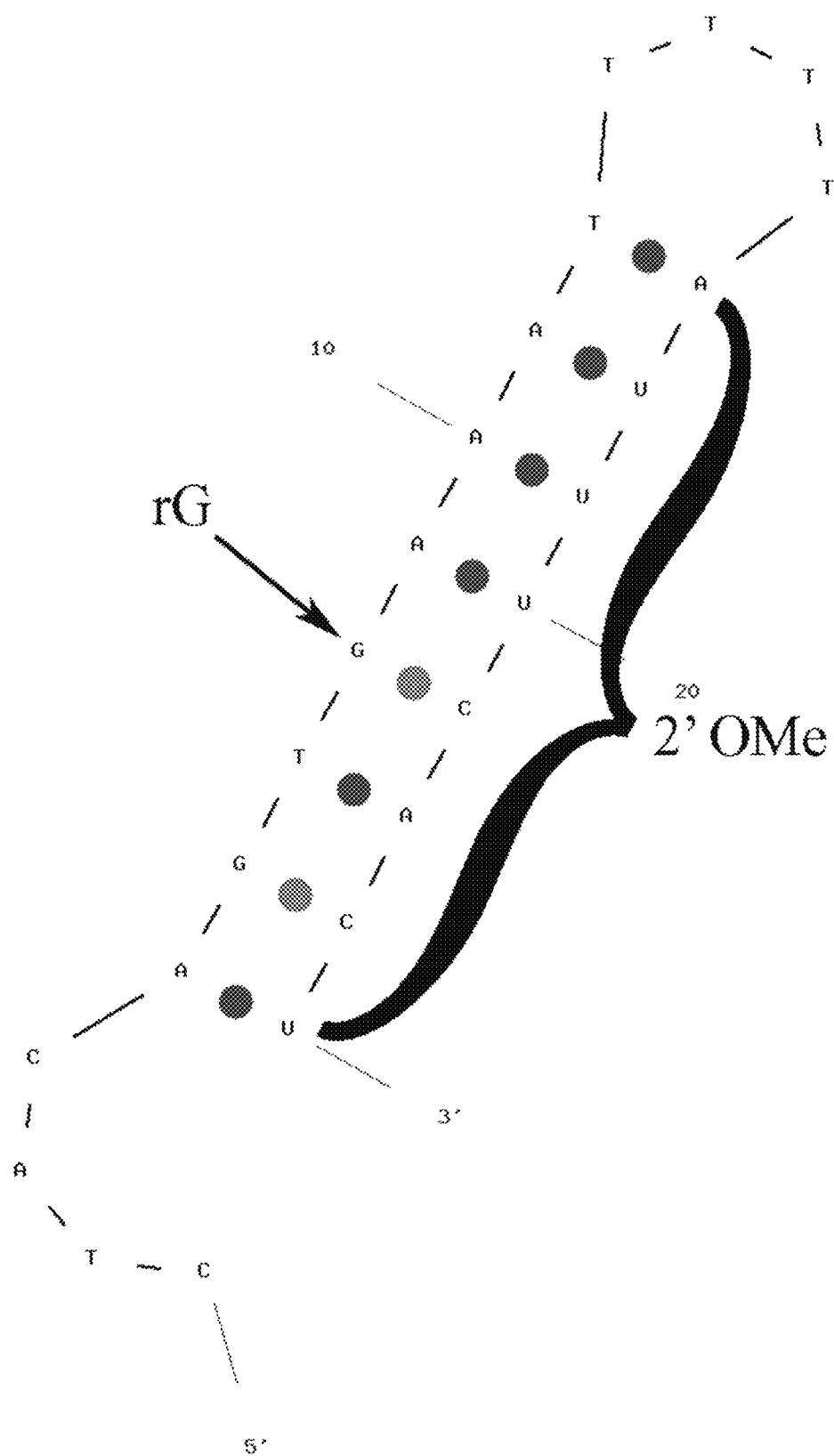
FIG. 5 (A-C) are representations of the hairpin region of hairpin blocked-cleavable primers designed to SNP rs113488022 where the stem region is extended and contains additional 2'-O-methyl ribonucleotides. The hairpin stem contains four thymidine residues and 8 (FIG. 5A), 9 (FIG. 5B), or 10 (FIG. 5C) 2'-O-methyl RNA bases to form the stem region. rG is the ribonucleotide base which is targeted by RNase H for cleavage when the rhPCR primer is bound to a complementary target. When the rhPCR primer is hybridized to the complementary target the RNase H will cleave 5' of the ribonucleotide base, activating the primer.
Figure 5B:
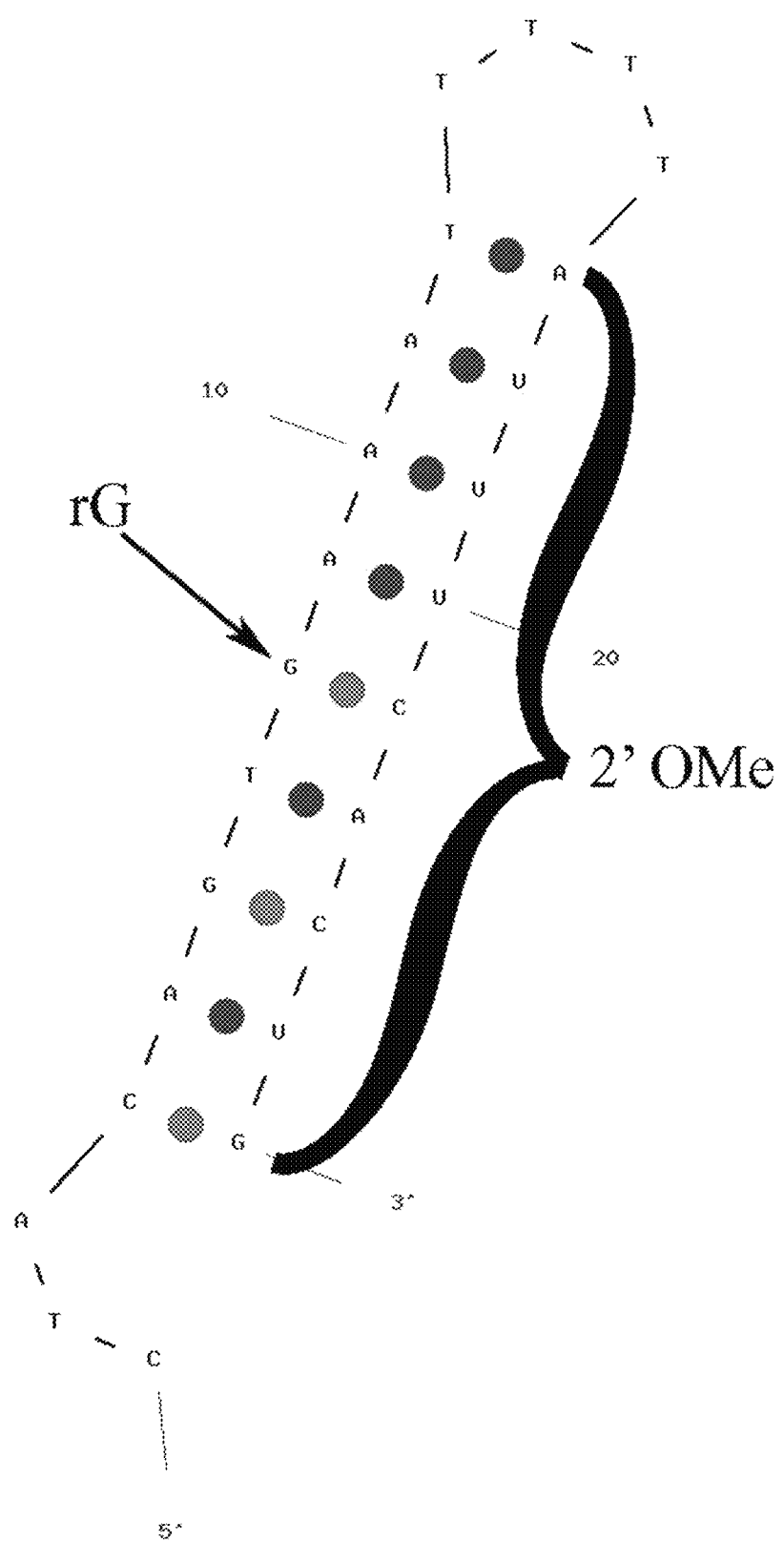
Figure 5C:
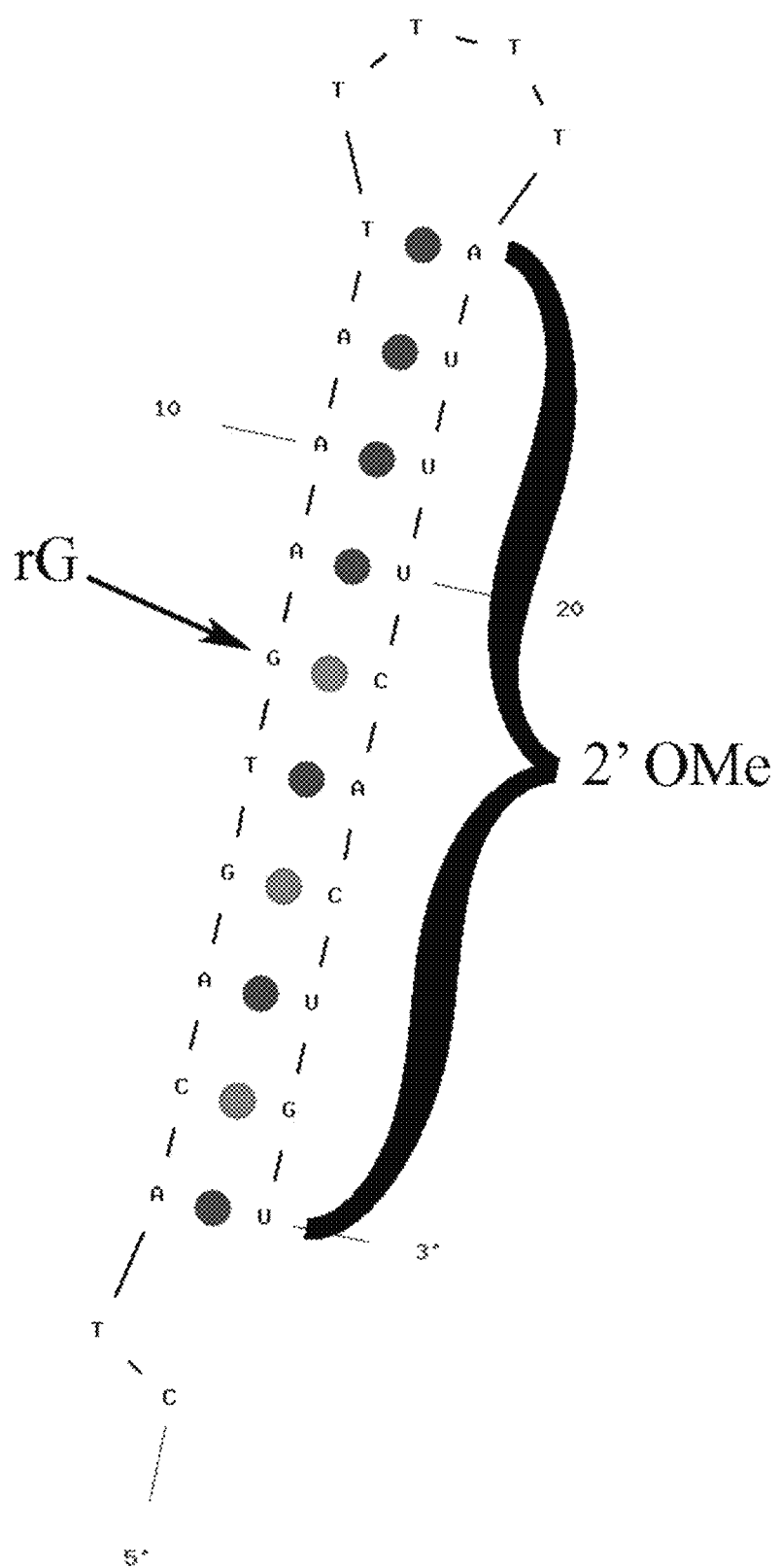
Figure 6A:
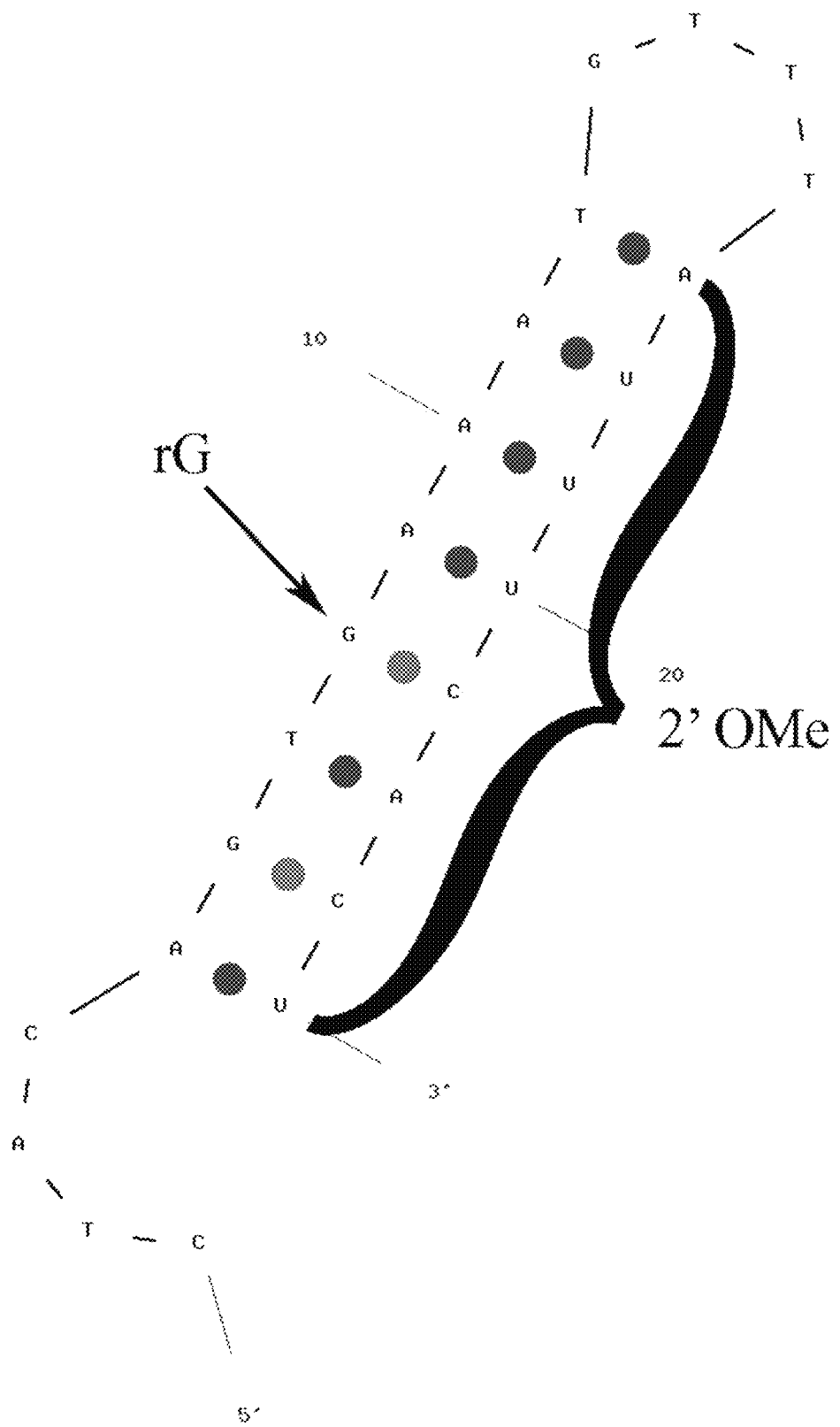
FIG. 6 (A-C) are representations of the hairpin and stem region of hairpin blocked-cleavable primers designed to SNP rs113488022, where the stem region is extended and includes a mismatched base 3' of the cleavage site. The hairpin stem consists of 3 thymidine residues and a mismatched base (G). The stem region contains 8 (FIG. 6A), 9 (FIG. 6B), or 10 (FIG. 6C) 2'-O-methyl RNA bases. rG is the ribonucleotide base which is targeted by RNase H for cleavage when the rhPCR primer is bound to a complementary target. When the rhPCR primer is hybridized to the complementary target the RNase H will cleave 5' of the ribonucleotide base, activating the primer.
Figure 6B:
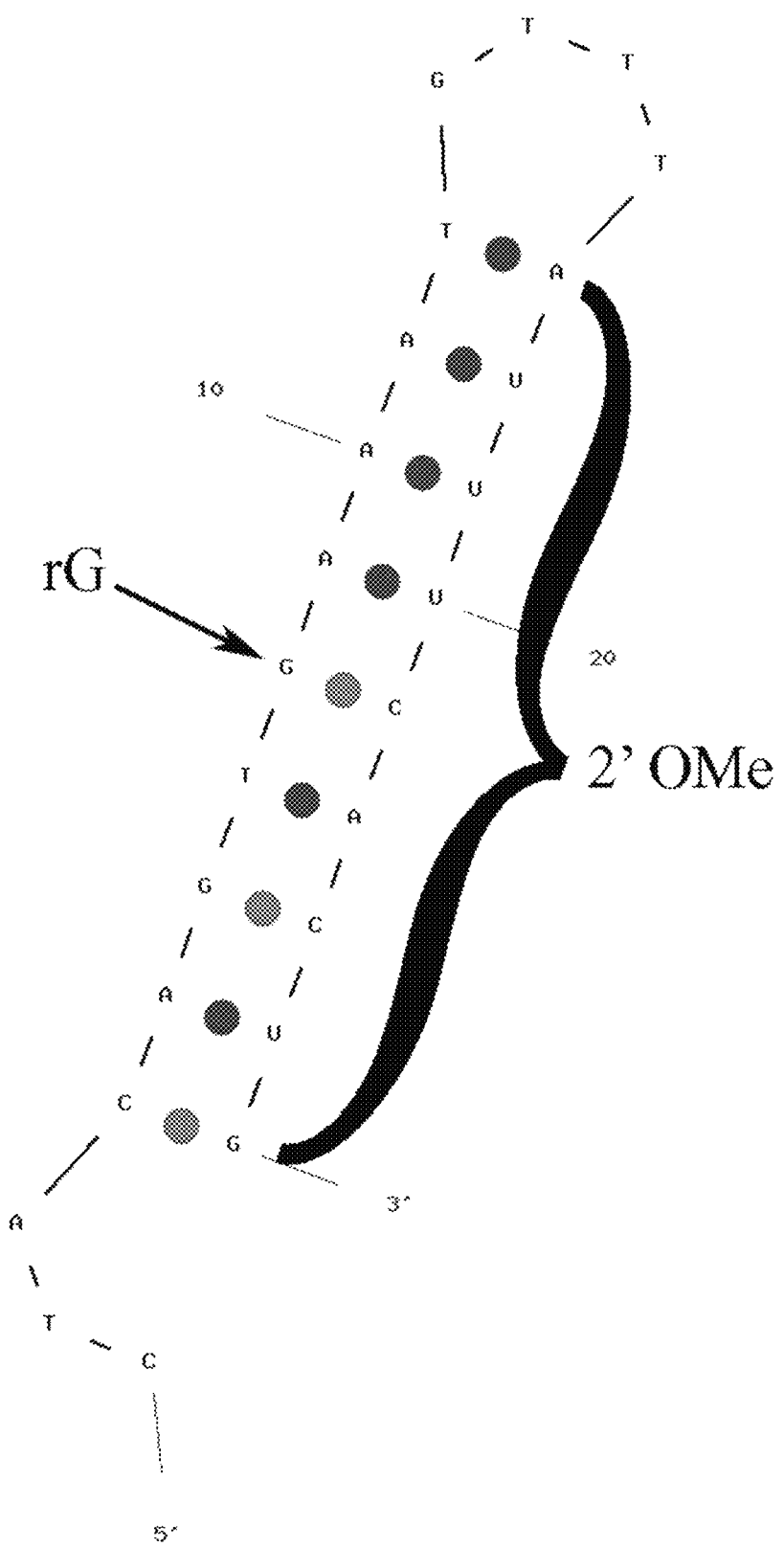
Figure 6C:
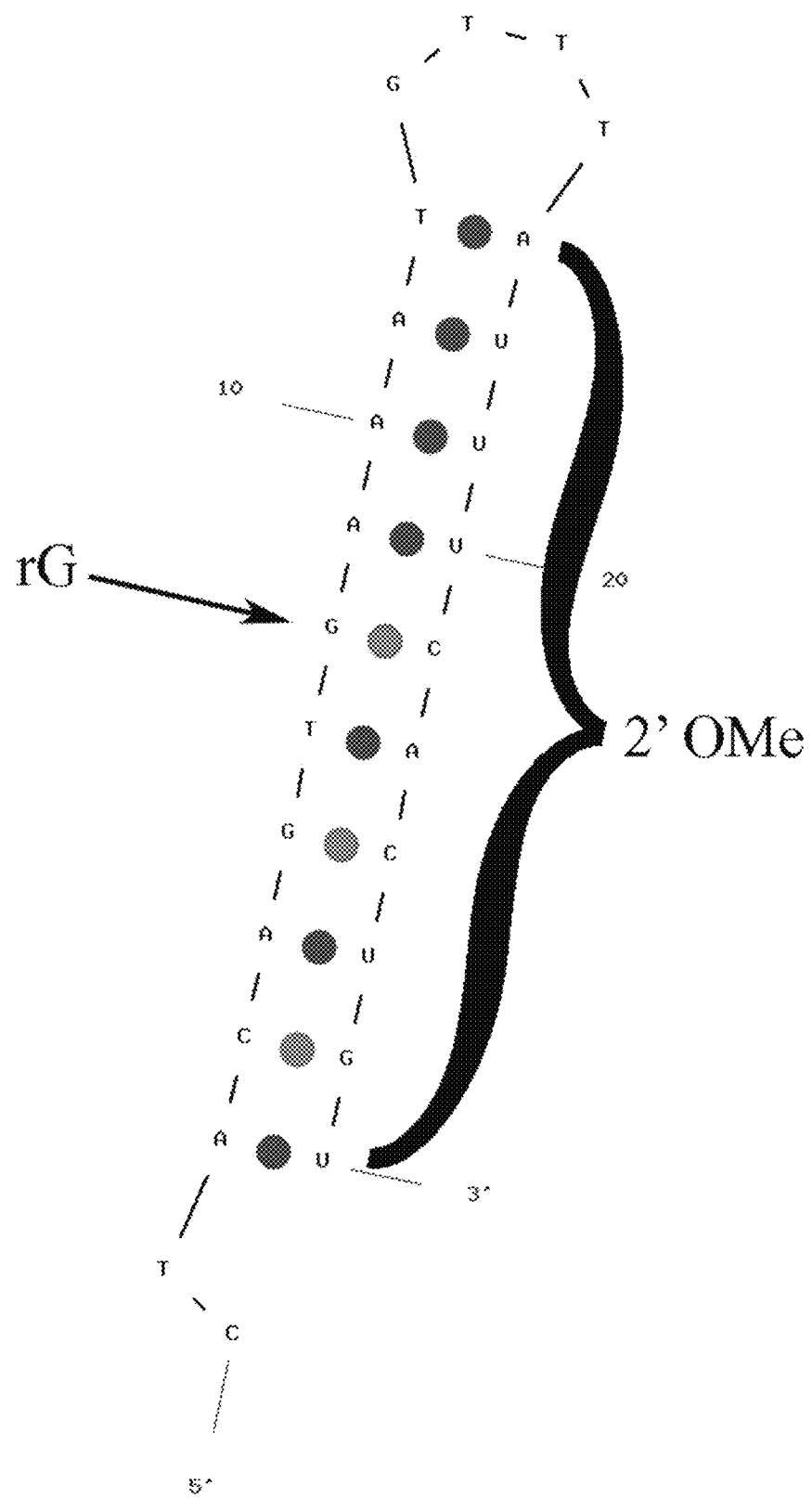
Figure 7A:
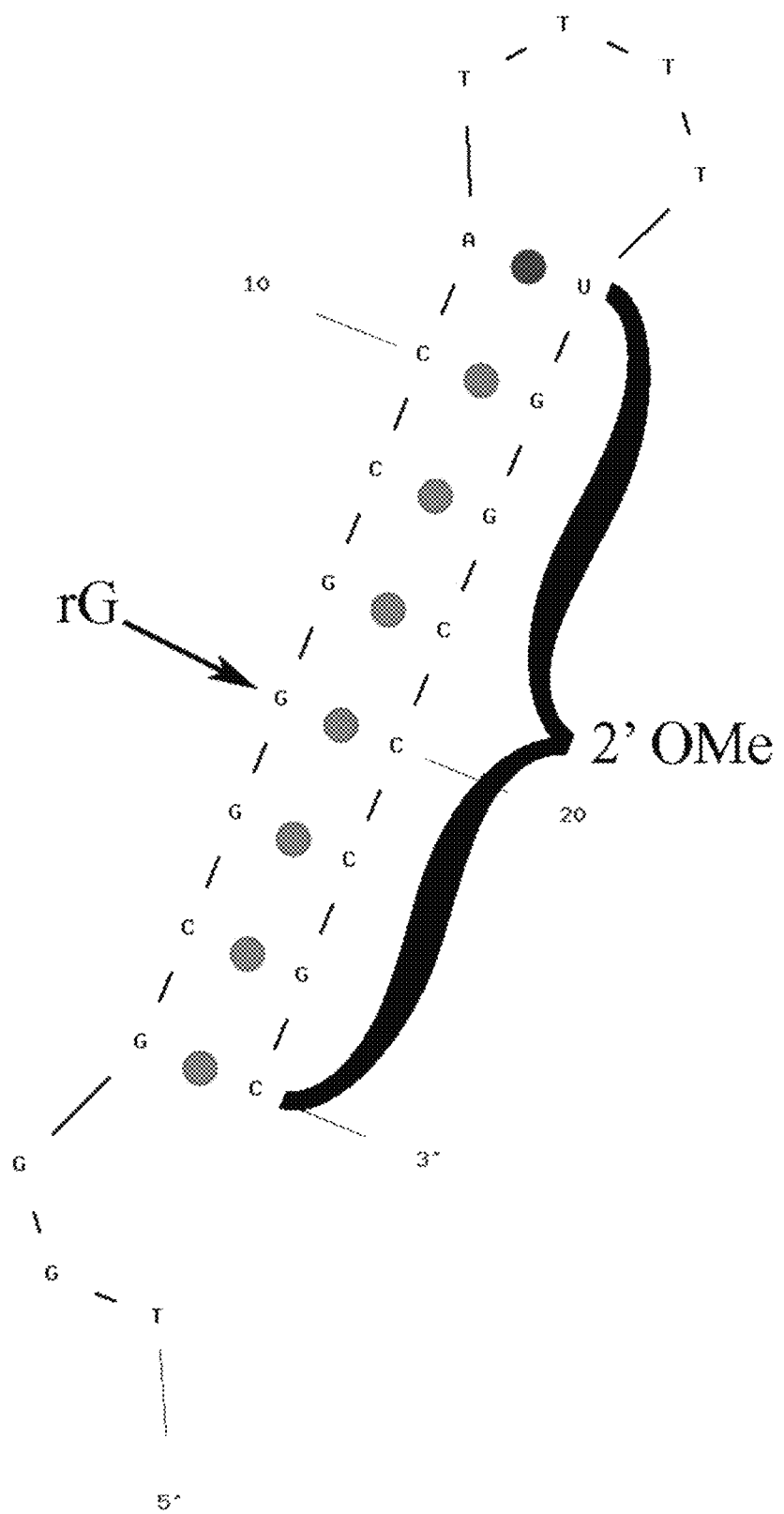
FIG. 7 (A-C) are representations of the hairpin and stem region of hairpin blocked-cleavable primers designed to SNP rs121434568, where the stem region includes a mismatched base 3' of the cleavage site. The hairpin loop consists of 3 thymidine residues and a mismatched base (T), making 4 T bases in total in the hairpin loop. The stem region contains 8 (FIG. 7A), 9 (FIG. 7B), or 10 (FIG. 7C) 2'-O-methyl RNA bases. rG is the ribonucleotide base which is targeted by RNase H for cleavage when the rhPCR primer is bound to a complementary target. When the rhPCR primer is hybridized to the complementary target the RNase H will cleave 5' of the ribonucleotide base, activating the primer.
Figure 7B:
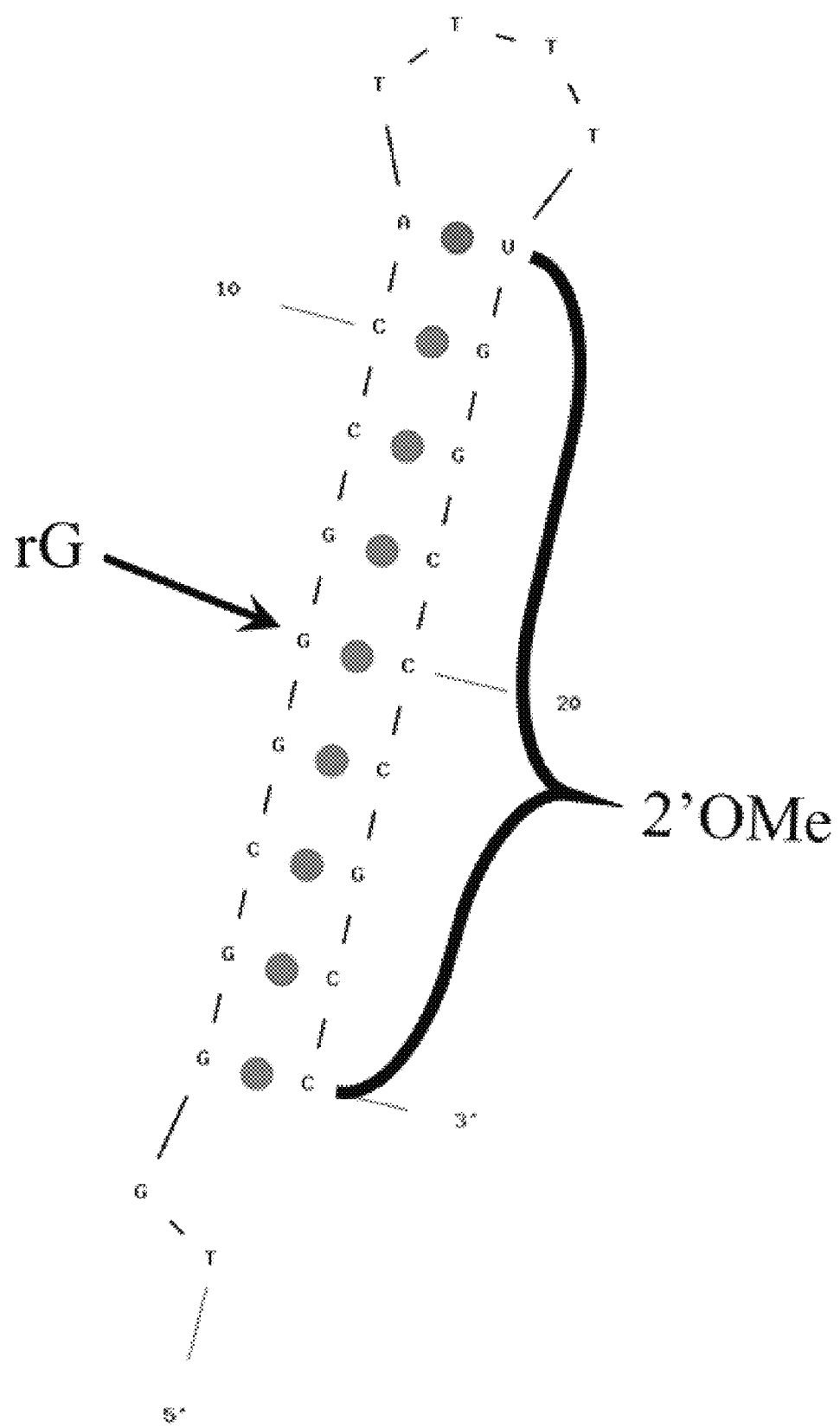
Figure 7C:
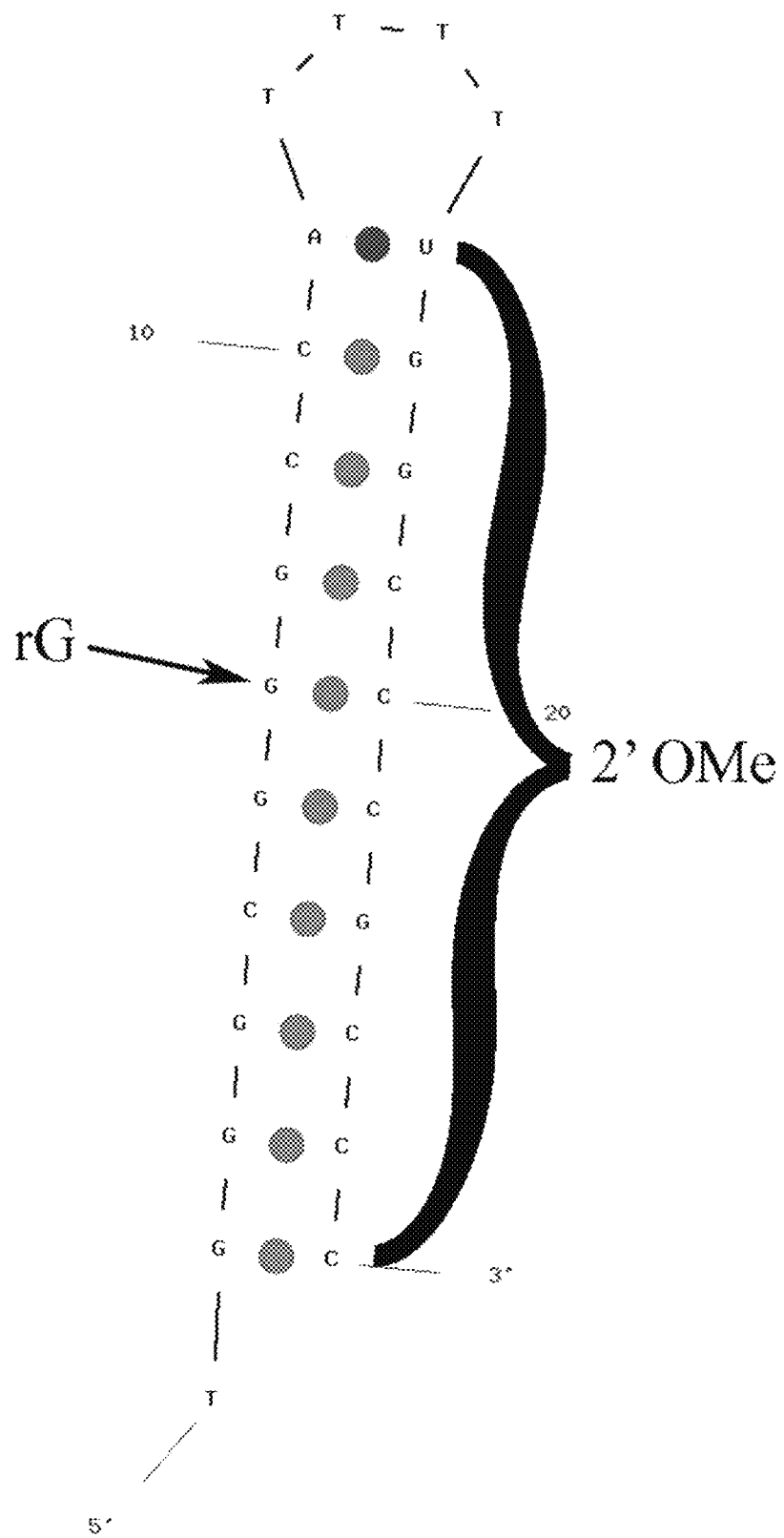
Figure 8A:
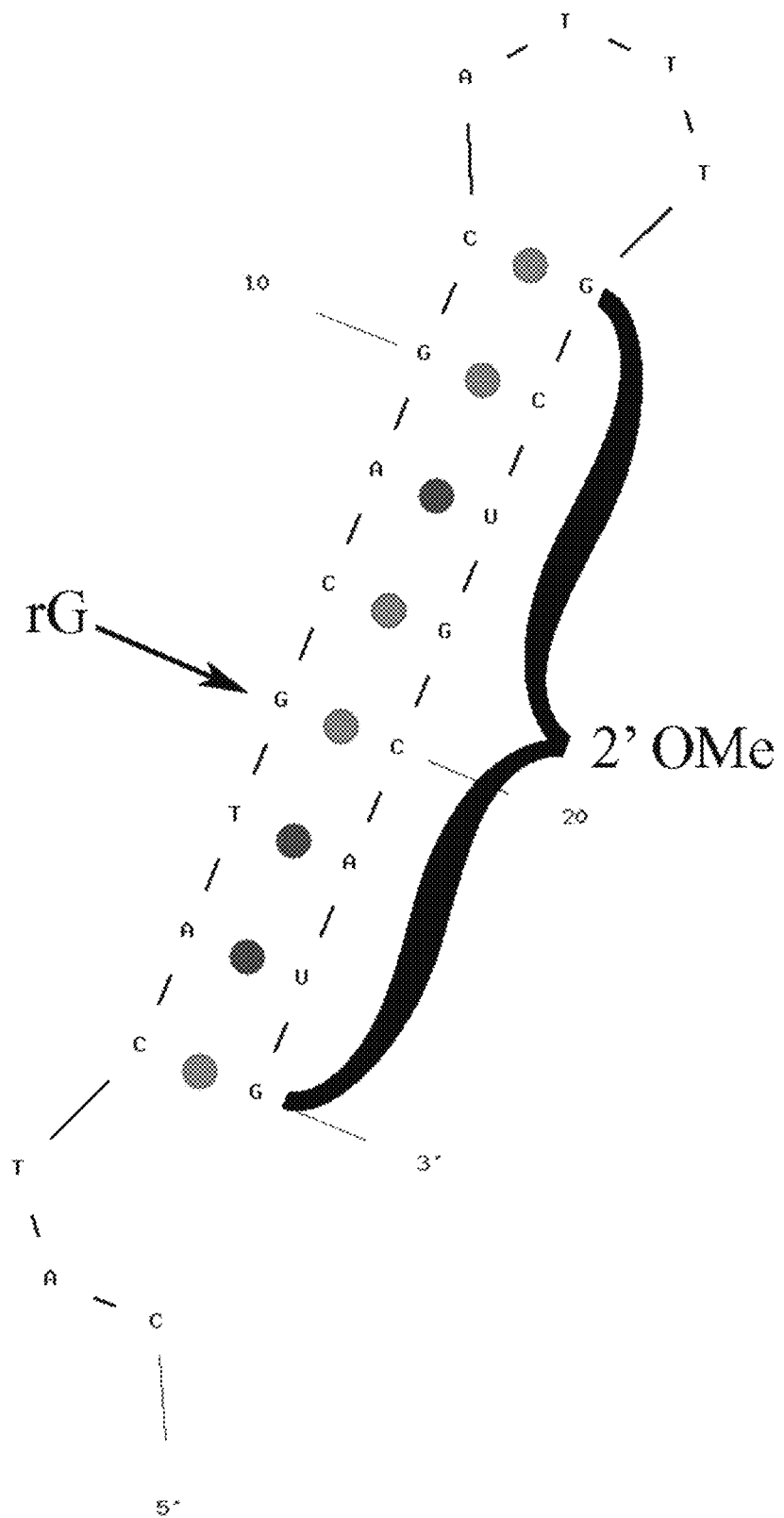
FIG. 8 (A-C) are representations of the hairpin and stem region of hairpin blocked-cleavable primers designed to SNP rs121434569, where the stem region includes a mismatched base 3' of the cleavage site. The hairpin loop consists of 3 thymidine residues and a mismatched base (A). The stem region contains 8 (FIG. 8A), 9 (FIG. 8B), or 10 (FIG. 8C) 2'-O-methyl RNA bases. rG is the ribonucleotide base which is targeted by RNase H for cleavage when the rhPCR primer is bound to a complementary target. When the rhPCR primer is hybridized to the complementary target the RNase H will cleave 5' of the ribonucleotide base, activating the primer.
Figure 8B:
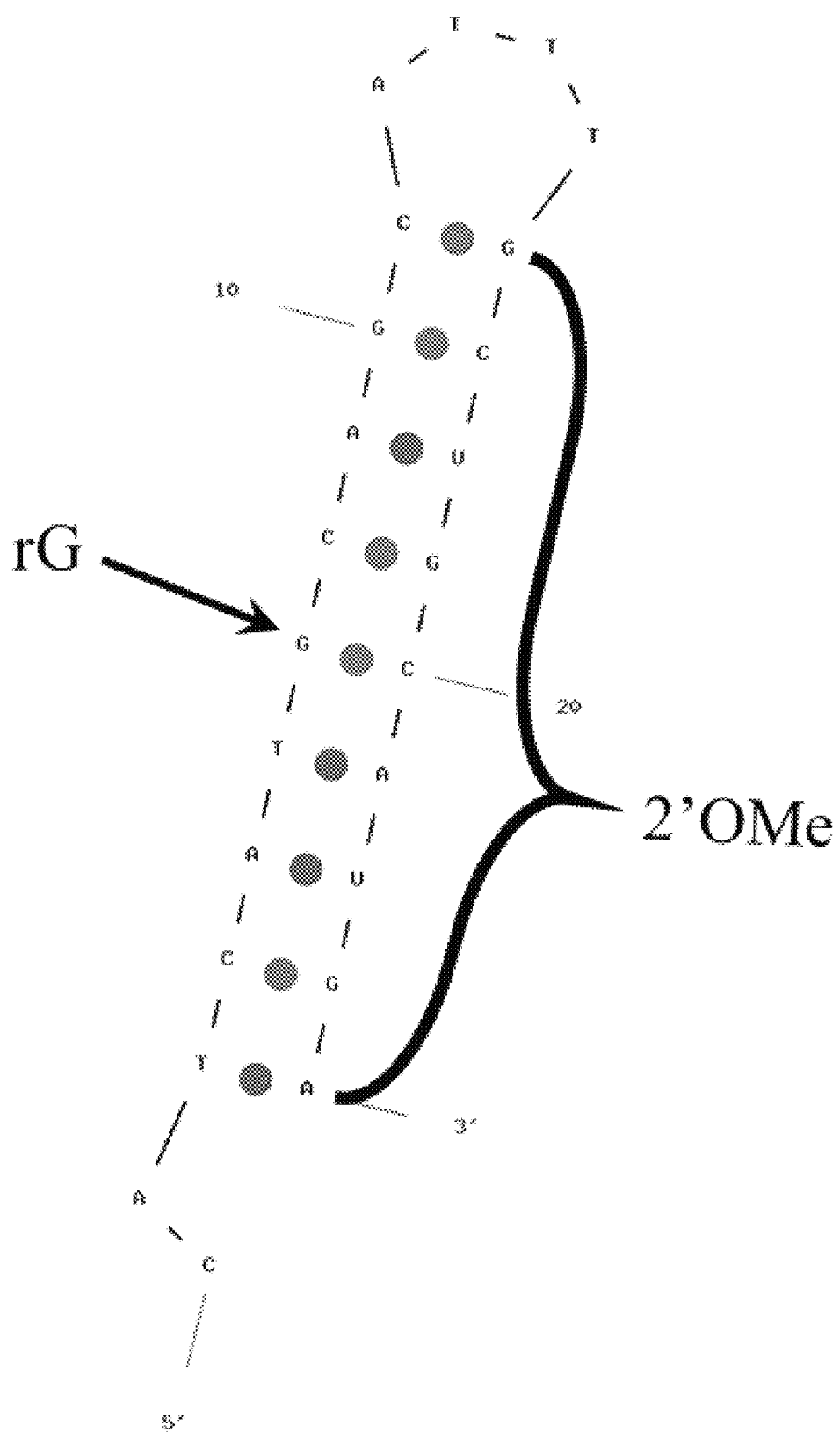
Figure 8C:
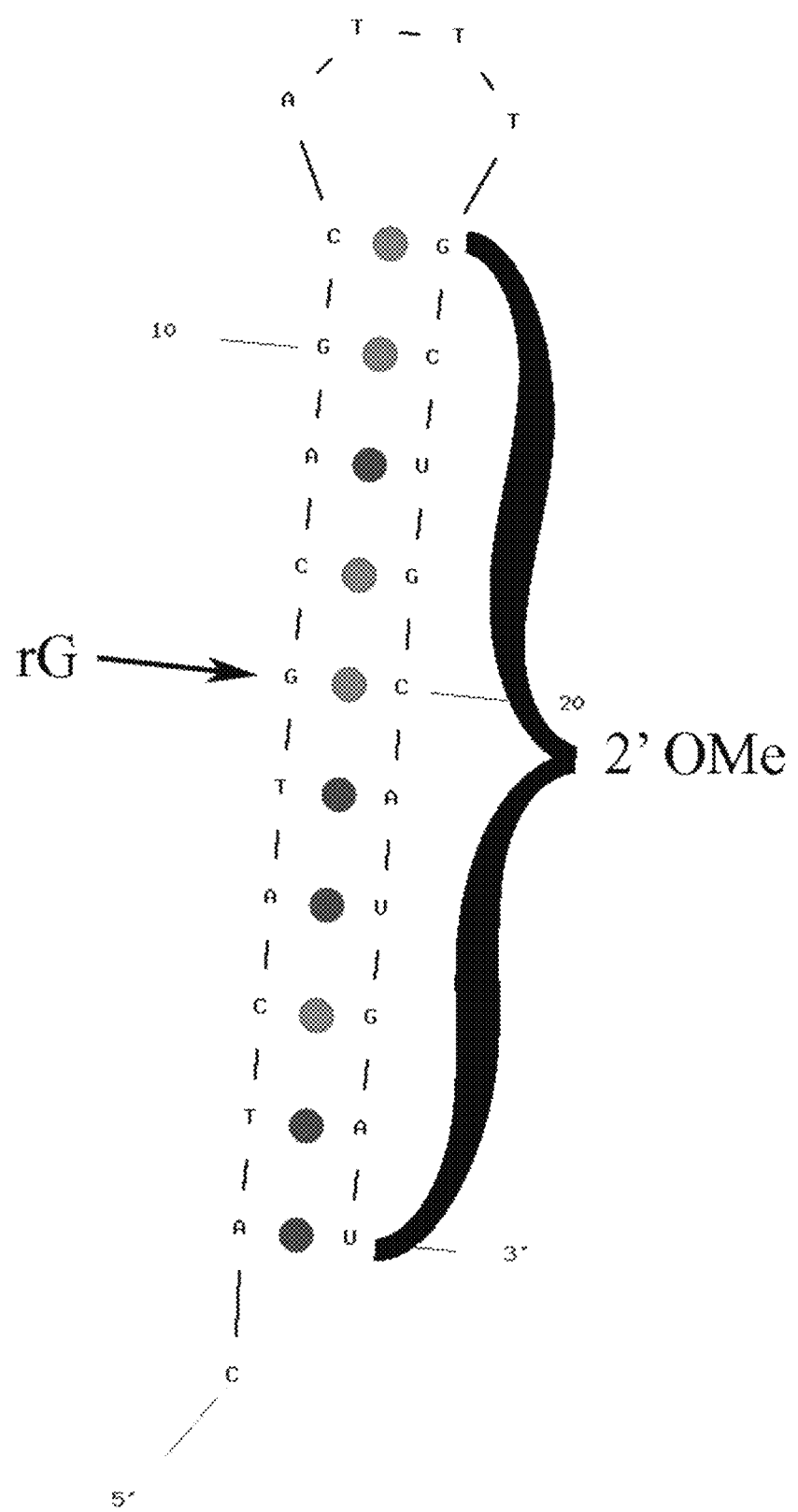

Cleavage results of the experiment are shown in FIG. 2. The data show that hairpin blocked rhPrimers protect the primers from single strand RNase cleavage as compared to the non-hairpin blocked rhPCR primer.

Example 5

This example demonstrates a modified hairpin blocked rhPCR primer. The primer contains a mismatch 5 bases 3' of the cleavage site.

TABLE 7

Sequence of oligonucleotides employed in SNP discrimination assay described in Example 5

| Sequence Name | Sequence | SEQ ID NO: |
|---|---|---|
| Forward non-discriminatory primer | GCTGTGATTTTGGTCTAGCTACAG | SEQ ID NO: 1 |
| Reverse unblocked primer | GCCCTCAATTCTTACCATCCACAAA | SEQ ID NO: 2 |
| Probe | FAM-TCCCATCAG-ZEN-TTTGAACAGTTGTCTGGA-IBFQ | SEQ ID NO: 3 |
| rs113488022 Forward 4dmx | GCTGTGATTTTGGTCTAGCTACAGTrGAAATG-x | SEQ ID NO: 4 |
| rs113488022 Forward 3tg8m | GCTGTGATTTTGGTCTAGCTACAGTrGAAATGTTTmAmUmUmUmCmAmCmU-x | SEQ ID NO: 17 |
| rs113488022 Forward 3tg9m | GCTGTGATTTTGGTCTAGCTACAGTrGAAATGTTTmAmUmUmUmCmAmCmUmG-x | SEQ ID NO: 18 |
| rs113488022 Forward 3tg10m | GCTGTGATTTTGGTCTAGCTACAGTrGAAATGTTTmAmUmUmUmCmAmCmUmGmU-x | SEQ ID NO: 19 |
| rs113488022 Forward 4t8m | GCTGTGATTTTGGTCTAGCTACAGTrGAAATTTTmAmUmUmUmCmAmCmU-x | SEQ ID NO: 14 |
| rs113488022 Forward 4t9 | GCTGTGATTTTGGTCTAGCTACAGTrGAAATTTTmAmUmUmUmCmAmCmUmG-x | SEQ ID NO: 15 |
| rs113488022 Forward 4t10m | GCTGTGATTTTGGTCTAGCTACAGTrGAAATTTTmAmUmUmUmCmAmCmUmGmU-x | SEQ ID NO: 16 |
| Reverse rhPrimer | GCCCTCAATTCTTACCATCCACAAArATGGAA-x | SEQ ID NO: 11 |
| T-amplicon | GCGTGATTTTGGTCTAGCTACAGTGAAATCTCGATGGAGTGGGTCCCATCAGTTTGAACAGTTGTCTGGATCCATTTTGTGGATGGTAAGAATTGAGGGC | SEQ ID NO: 12 |
| A-amplicon | GCGTGATTTTGGTCTAGCTACAGAGAAATCTCGATGGAGTGGGTCCCATCAGTTTGAACAGTTGTCTGGATCCATTTTGTGGATGGTAAGAATTGAGGGC | SEQ ID NO: 13 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa, x=C3 propanediol spacer block, mA=2'-

O-Methyl Adenine RNA, mU=2'O-Methyl Uracil RNA, mC=2'-O-Methyl Cytosine RNA, mG=2'-O-Methyl Guanosine RNA, rG=Guanosine RNA, rA=Adenine RNA.

10 uL reaction volumes were used in these assays. To perform the reaction, 5 uL of 2×V2.2 Genie RN2 Master Mix (IDT, Coralville, Iowa) (1× final, containing dNTPS, H784Q mutant polymerase, stabilizers, and $MgCl_2$) was combined with 500 nM (5 pmol) of the forward primer, 250 nM (2.5 pmol) of the probe, as well as 500 nM (5 pmol) of the reverse primer were also added. Additionally, 7.5 mU (13.6 fmol; 1.36 nM) of P.a. RNase H2 (*Pyrococcus abyssi* RNase H2) and 1000 copies of either template amplicon (present as a double-stranded gBlock™ template; SEQ ID Nos. 12 or 13) were added to the reaction mix. The reaction was thermocycled on a CFX384™ Real-time system (Bio-Rad™, Hercules, Calif.). Cycling conditions were as follows: $95^{3:00}$–$(95^{0:10}$–$65^{0:45})$×55. Each reaction was performed in triplicate.

Cq and ΔCq Results of the experiment are shown in Table 8. This data shows that the mismatch discrimination of the assays system is approximately equivalent when the $5^{th}$ base is a mismatch nucleobase as compared to a matching base.

TABLE 8

Cq values from the experiment described in Example 5.

| Sequence Name | SEQ ID NO: | T-amplicon | A-amplicon | ΔCq | NTC |
|---|---|---|---|---|---|
| Non-discrim | 1 | 29.0 | 29.3 | | >55 |
| 4Dmx | 4 | 30.6 | 42.4 | 11.8 | >55 |
| 4t8m | 14 | 30.6 | 44.4 | 13.8 | >55 |
| 4t9m | 15 | 31.7 | 45.5 | 13.8 | >55 |
| 4t10m | 16 | 31.5 | 44.5 | 13.0 | >55 |
| 3tg8m | 17 | 31.2 | 45.5 | 14.4 | >55 |
| 3tg9m | 18 | 44.9 | 43.7 | 13.5 | >55 |
| 3tg10m | 19 | 31.4 | 43.3 | 12.5 | >55 |

Example 6

This example demonstrates the use of 2' OMethyl modified hairpin blocked-cleavable primers to detect different SNPs.

To demonstrate the utility of the new hairpin blocked-cleavable primers, rhPCR primers, and unblocked primers were designed against rs121434569, the T790M mutation in the human EGFR gene, and rs121434568, the L858R mutation in the human EGFR gene. The hairpin blocked-cleavable primers contain a loop of four thymidine residues. The hairpin blocked-cleavable primers also contain either eight 2'-O-Methyl complementary RNAs, nine 2'-O-Methyl complementary RNAs, or ten 2'O-Methyl complementary RNAs. These primers were tested in PCR and rhPCR with the H784Q mutant Taq polymerase.

TABLE 9

Sequences of primers used in a blocked hairpin rhPCR assay.

| Sequence Name | Sequence | SEQ ID NO: |
|---|---|---|
| rs121434569 Forward non-discriminatory primer | ACCGTGCAGCTCATCAT | SEQ ID NO: 20 |
| rs121434569 Reverse unblocked primer | ACCTAAAGCCACCTCCTTACT | SEQ ID NO: 21 |
| rs121434569 Forward 4dmx | ACCGTGCAGCTCATCATrGCAGC A-x | SEQ ID NO: 22 |
| rs121434569 Forward 3ta8m | ACCGTGCAGCTCATCATrGCAGC ATTTmGmCmUmGmCmAmUmG-x | SEQ ID NO: 23 |
| rs121434569 Forward 3ta9m | ACCGTGCAGCTCATCATrGCAGC ATTTmGmCmUmGmCmAmUmGm A-x | SEQ ID NO: 24 |
| rs121434569 Forward 3ta10m | ACCGTGCAGCTCATCATrGCAGC ATTTmGmCmUmGmCmAmUmGmAm U-x | SEQ ID NO: 25 |
| rs121434569 reverse rhPrimer | ACCTAAAGCCACCTCCTTACTrU TGCCA-x | SEQ ID NO: 26 |
| rs121434569 probe | FAM-CCTTCGGCT-ZEN-GCCTC CTGGACTAT-IBFQ | SEQ ID NO: 27 |
| rs121434569 T-Template | ACCGTGCAGCTCATCATGCAGCT CATGCCCTTCGGCTGCCTCCTGG ACTATGTCCGGGAACACAAAGAC AATATTGGCTCCCAGTACCTGCT CAACTGGT | SEQ ID NO: 28 |
| rs121434569 C-Template | ACCGTGCAGCTCATCACGCAGCT CATGCCCTTCGGCTGCCTCCTGG ACTATGTCCGGGAACACAAAGAC AATATTGGCTCCCAGTACCTGCT CAACTGGT | SEQ ID NO: 29 |
| rs121434568 Forward non-discriminatory primer | TCAAGATCACAGATTTTGGGC | SEQ ID NO: 30 |
| rs121434568 Reverse unblocked primer | AGTTGAGCAGGTACTGGGA | SEQ ID NO: 31 |
| rs121434568 Forward 4dmx | TCAAGATCACAGATTTTGGGCGr GGCCAT-x | SEQ ID NO: 32 |
| rs121434568 Forward 4t8m | TCAAGATCACAGATTTTGGGCGr GGCCATTTTmUmGmGmCmCmCmG mC-x | SEQ ID NO: 33 |
| rs121434568 Forward 4t9m | TCAAGATCACAGATTTTGGGCGr GGCCATTTTmUmGmGmCmCmCmG mCmC-x | SEQ ID NO: 34 |
| rs121434568 Forward 4t10m | TCAAGATCACAGATTTTGGGCGr GGCCATTTTmUmGmGmCmCmCmG mCmCmC-x | SEQ ID NO: 35 |
| rs121434568 Reverse rhPrimer | AGTTGAGCAGGTACTGGGArGCC AT-x | SEQ ID NO: 36 |
| rs121434568 probe | FAM-CTGGGTGCG-ZEN-GAAGA GAAAGAATACCA-IBFQ | SEQ ID NO: 37 |

TABLE 9-continued

Sequences of primers used in a
blocked hairpin rhPCR assay.

| Sequence Name | Sequence | SEQ ID NO: |
|---|---|---|
| rs121434568 T-Template | TCAAGATCACAGATTTTGGGCTG GCCAAACTGCTGGGTGCGGAAGA GAAAGAATACCATGCAGAAGGAG GCAAAGTAAGGAGGTGGCTTTAG GT | SEQ ID NO: 38 |
| rs121434568 G-Template | TCAAGATCACAGATTTTGGGCGG GCCAAACTGCTGGGTGCGGAAGA GAAAGAATACCATGCAGAAGGAG GCAAAGTAAGGAGGTGGCTTTAG GT | SEQ ID NO: 39 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa, x=C3 propanediol spacer block, mA=2'-O-Methyl Adenine RNA, mU=2'O-Methyl Uracil RNA, mC=2'-O-Methyl Cytosine RNA, mG=2'-O-Methyl Guanosine RNA, rG=Guanosine RNA, rA=Adenine RNA.

10 uL reaction volumes were used in these assays. To perform the reaction, 5 uL of 2×V2.2 Genie RN2 Master Mix (IDT, Coralville, Iowa) (1× final, containing dNTPS, H784Q mutant polymerase, stabilizers, and MgCl$_2$) was combined with 500 nM (5 pmol) of forward primer, 250 nM (2.5 pmol) of the probe, as well as 500 nM (5 pmol) of the reverse primer were also added. Additionally, 7.5 mU (13.6 fmol; 1.36 nM) of P.a. RNase H2 (*Pyrococcus abyssi* RNase H2) and 1000 copies of the appropriate template (present as a double-stranded gBlock™ template; SEQ ID Nos. 28, 29, 38, or 39) were added to the reaction mix. The reaction was thermocycled on a CFX384™ Real-time system (Bio-Rad™, Hercules, Calif.). Cycling conditions were as follows: $95^{3:00}-(95^{0:10}-65^{0:45})\times55$. Each reaction was performed in triplicate.

Cq and ΔCq Results of the experiment are shown in Table 10. The data show that the mismatch discrimination of hairpin blocked-cleavable primers can be used to detect different SNPs and that the mismatch discrimination is increased over both unblocked and 4dmx rhPCR primers.

Example 7

This example demonstrates that DNA hairpin blocked-cleavable primers are not prematurely cleaved by RNase H2 at reaction temperatures.

Figure 9:
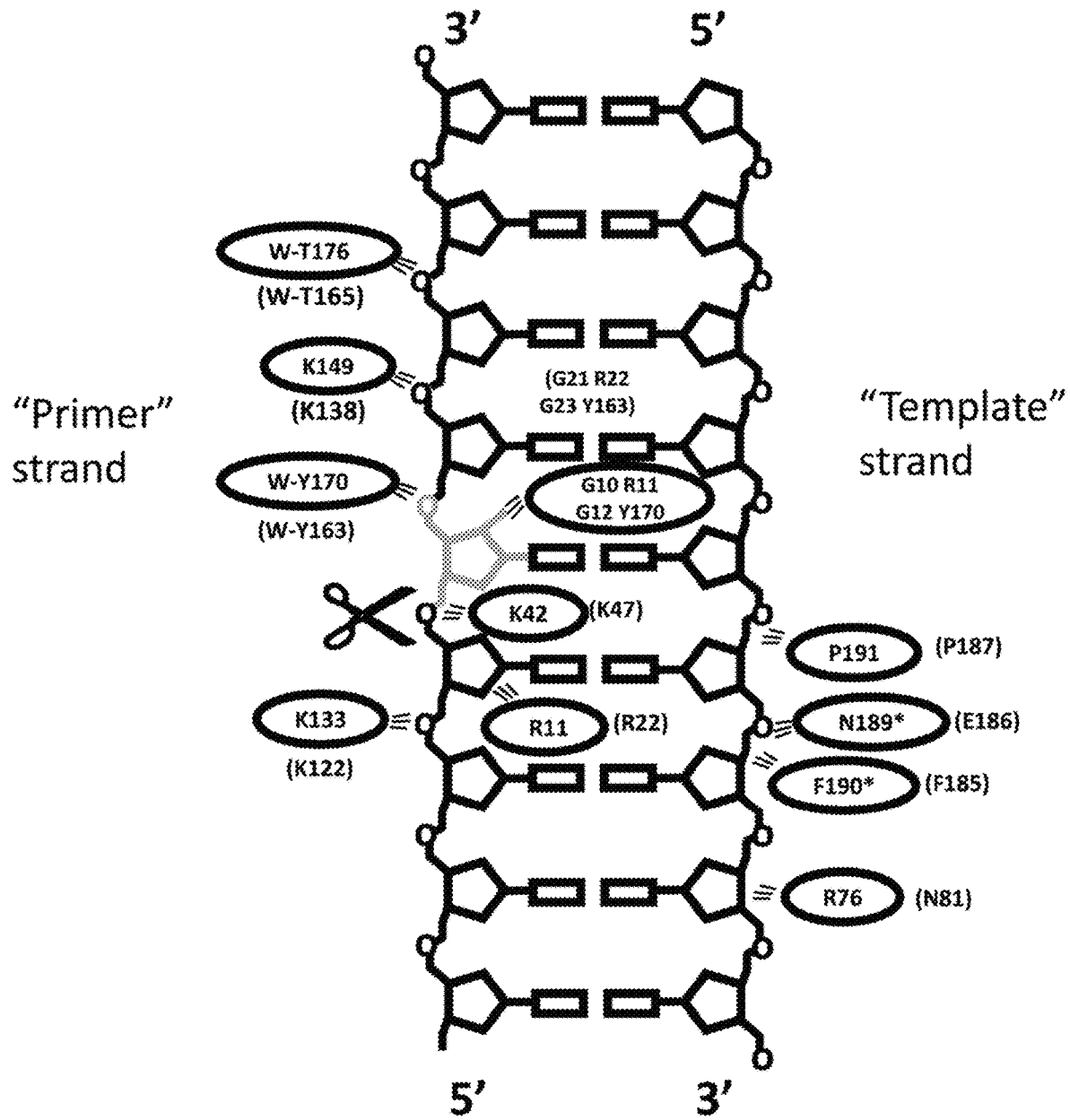
FIG. 9 is a diagram of the contact points of a P.a. RNase H2 enzyme in a drawing adapted from crystal structure data utilizing the Type II RNase H from *Thermotoga maritima* (Rychlik et al., 2010). Amino acid numbers for the *Pyrococcus abyssi* RNase H2 enzyme are shown in the bubbles, with the corresponding *Thermotoga maritima* amino acid numbers from the crystal structure shown either below or to the side in parentheses. The cleavable RNA residue in the template is shown in light grey. The cleavable phosphate linkage is indicated by the scissors. Contact points on the "template" strand are noticeably absent 5' of the nucleotide opposite the RNA residue.
Figure 10A:
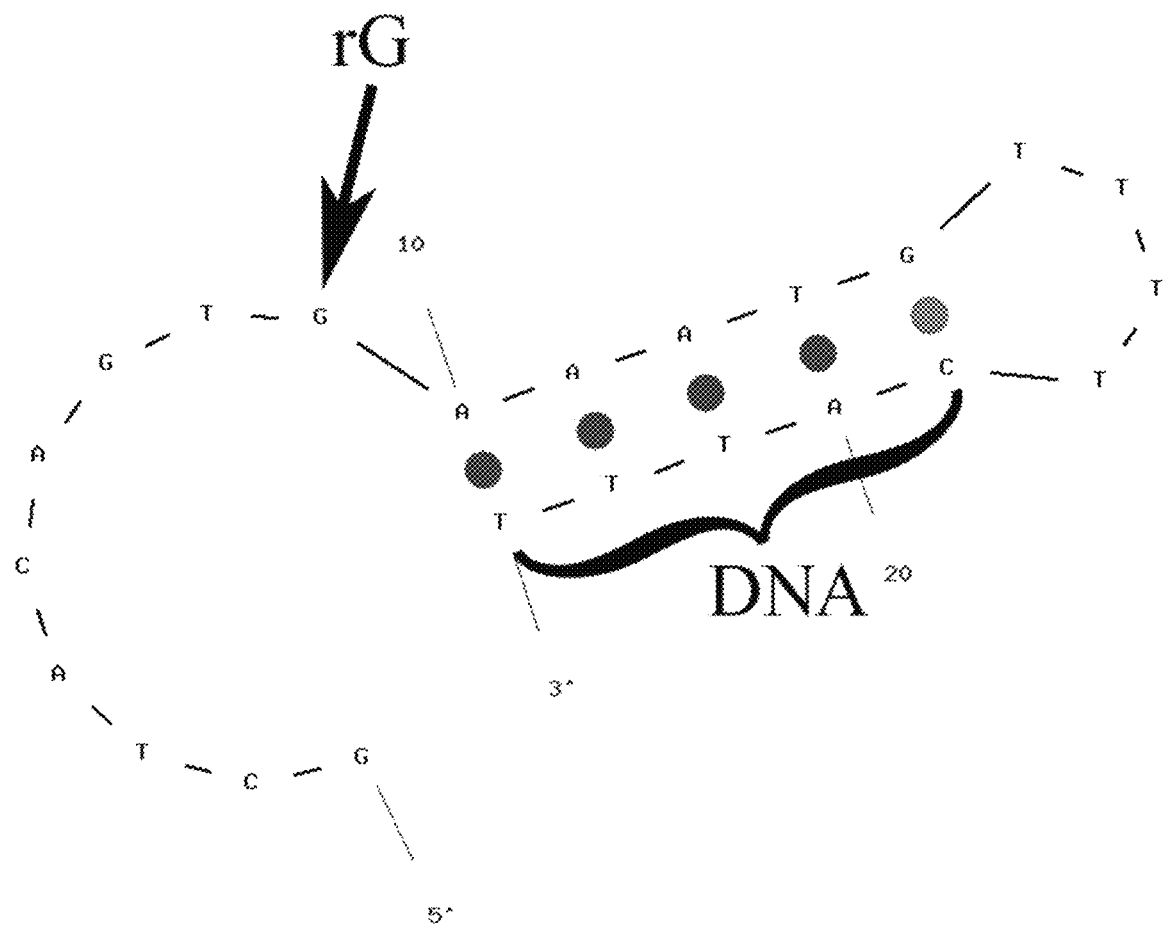
FIG. 10 (A-E) are representations of the hairpin region of hairpin blocked-cleavable primers designed to SNP rs113488022 where the stem region contains only a single ribonucleotide and an increasing number of DNA residues. The hairpin stem contains four thymidine residues and 5 (FIG. 10A), 6 (FIG. 10B), 7 (FIG. 10C), 8 (FIG. 10D), or 9 (FIG. 10E) DNA nucleotides to form the stem region. rG is the ribonucleotide base which is targeted by RNase H for cleavage when the rhPCR primer is bound to a complementary target. When the rhPCR primer is hybridized to the complementary target the RNase H will cleave 5' of the ribonucleotide base, activating the primer.
Figure 10B:
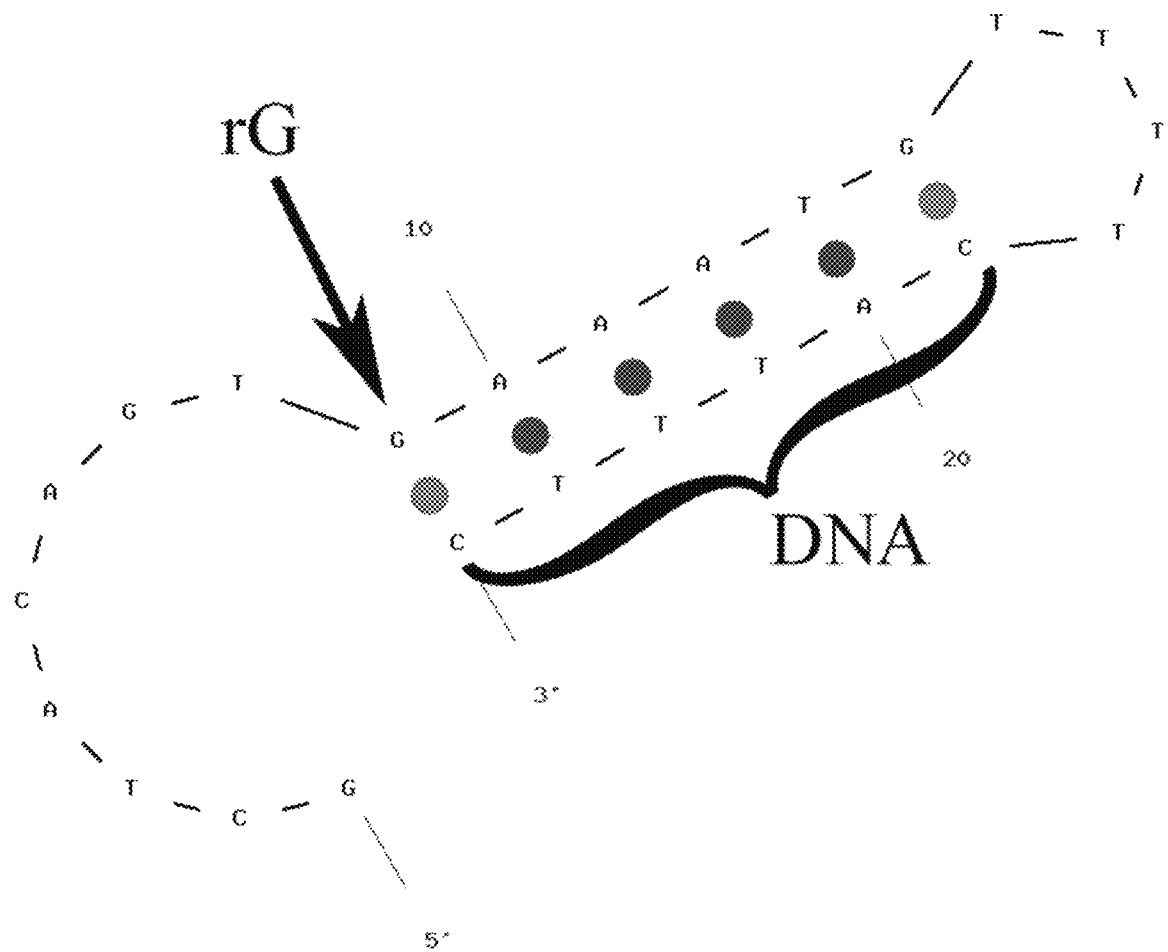
Figure 10C:
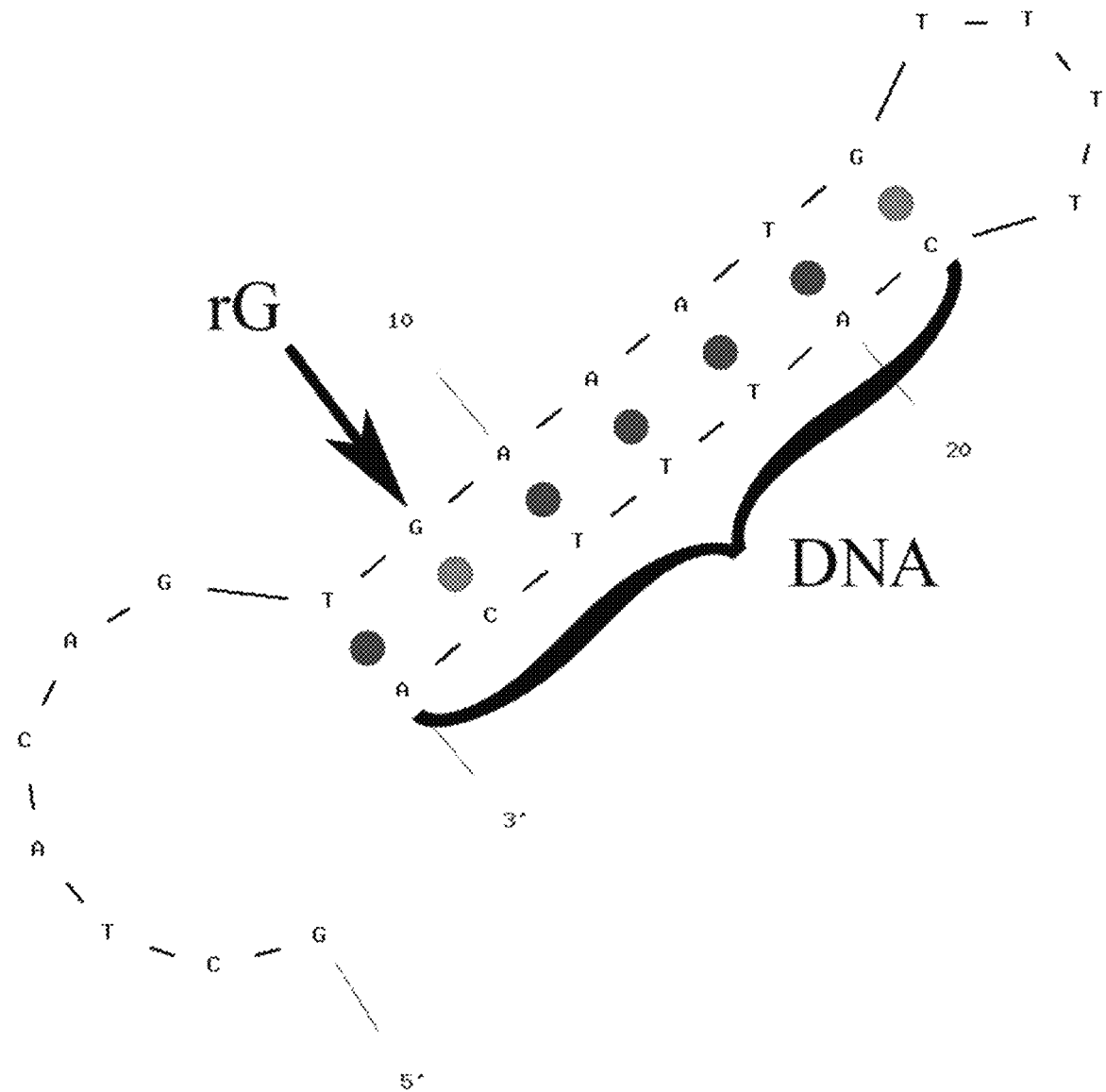
Figure 10D:
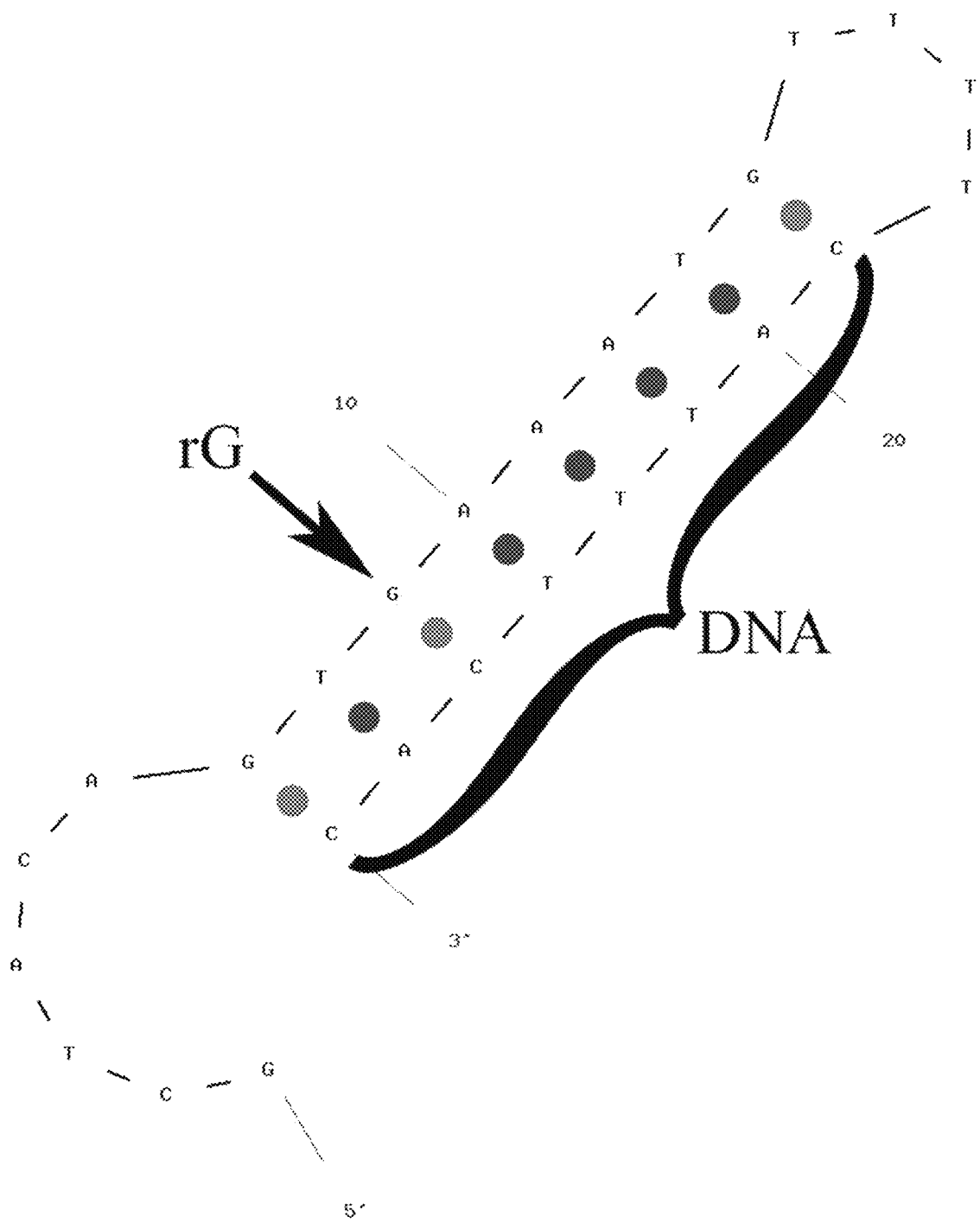
Figure 10E:
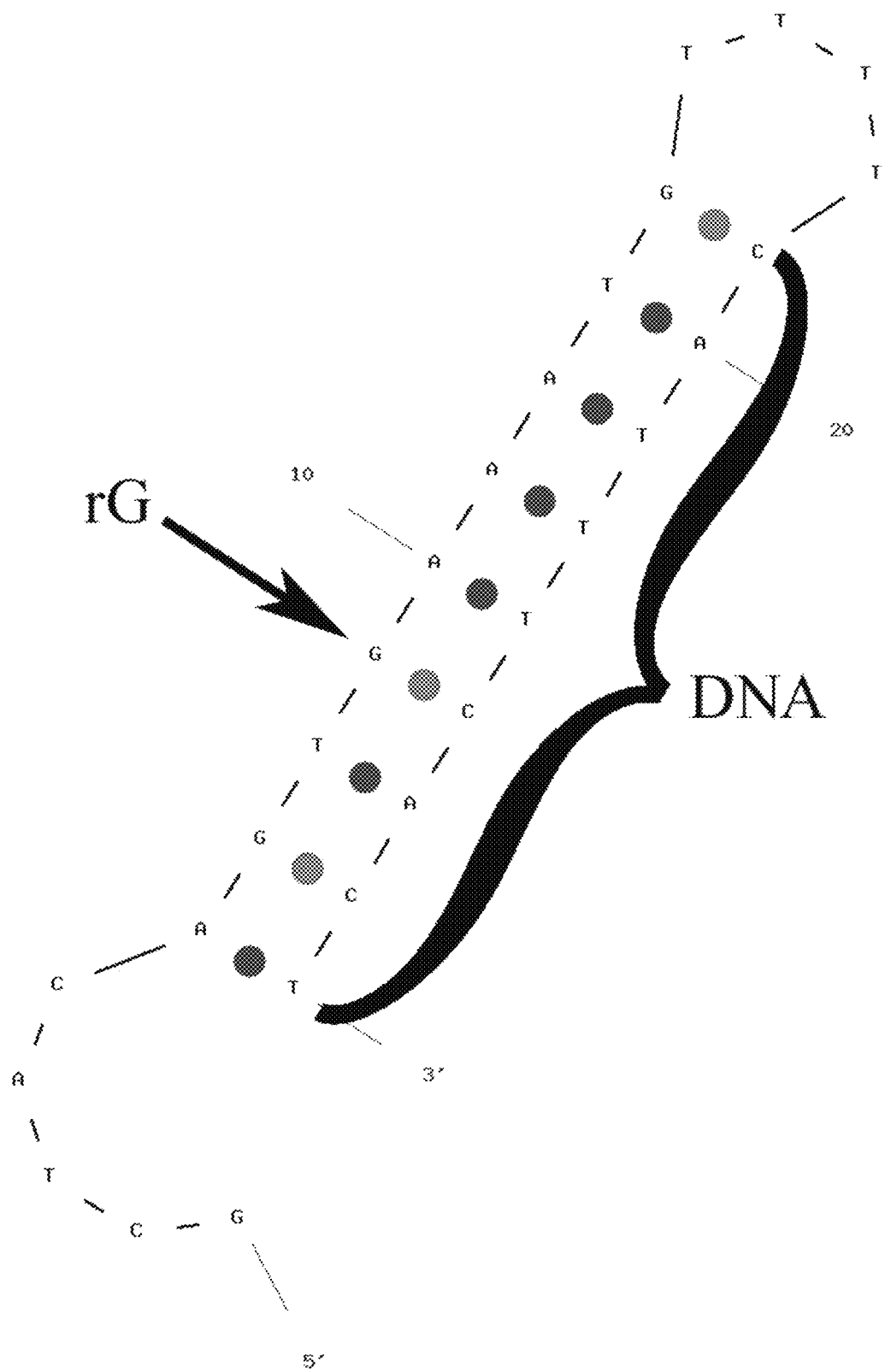

Thermostable prokaryotic RNase H2 enzymes have significant structural homology with one another. A co-crystal structure showing the sites of contact between the protein and the substrate was published in 2010 (Rychlik et al. 2010). From this paper, it is clear that RNase H2 enzymes make numerous contacts with the template on both strands, but there are no conserved protein-template contacts located on the template strand 5' of the residue immediately opposite the cleavable RNA residue (FIG. 9). Because of this, a blocked-cleavable hairpin rhPCR primer consisting of a single RNA with a DNA hairpin could be designed so as to not be cleaved in the solution before it bound to the target. This design has significant advantages in terms of the simplicity and price of synthesis versus 2'OMe hairpin designs. It was observed that there are conserved protein-template contact points located 3' of the residue opposite the cleavable RNA residue, so it was necessary to test to determine how far the double-stranded region of the hairpin could extend without allowing for cleavage and removal of the block by the RNase H2 enzyme before it bound to the template.

To demonstrate the number of double-stranded bases pairs required for cleavage of DNA hairpin blocked-cleavable primers, primers were designed to detect rs113488022, the V600E mutation in the human BRAF gene. The hairpin blocked-cleavable primers contain a loop of four thymidine residues, and increasing lengths of the double-stranded domain. The sequences of the primers are shown in Table 10, and their hairpin structures are shown in FIG. 10A-E.

TABLE 10

Sequences of the DNA hairpin blocked-
cleavable primers utilized in Example 7.

| Sequence Name | Sequence | SEQ ID NO: |
|---|---|---|
| rs113488022 Forward 4t5d | GCTGTGATTTTGGTCTAGCTACAG TrGAAATGTTTTCATTT-x | SEQ ID NO: 40 |

TABLE 10

Cq Values obtained from the experiment described in Example 6.

| SNP ID | Seq. name | SEQ ID NO: | G-amplicon | T-amplicon | ΔCq | NTC |
|---|---|---|---|---|---|---|
| rs121434568 | Non-discr | 30 | 28.9 | 28.8 | | >55 |
| | 4dmx | 32 | 29.2 | 41.8 | 12.6 | >55 |
| | 4t8m | 33 | 35.8 | 43.7 | 7.9 | >55 |
| | 4t9m | 34 | 42.9 | 51.3 | 8.4 | >55 |
| | 4t10m | 35 | 51.2 | >55 | >3.8 | >55 |

| SNP ID | Seq. name | SEQ ID NO: | T-template | C-template | ΔCq | NTC |
|---|---|---|---|---|---|---|
| rs121434569 | Non-discr | 20 | 30.1 | 29.7 | | >55 |
| | 4dmx | 22 | 31.1 | 45.6 | 14.5 | >55 |
| | 4t8m | 23 | 32.7 | 50.2 | 17.5 | >55 |
| | 4t9m | 24 | 33.1 | 46.8 | 13.6 | >55 |
| | 4t10m | 25 | 34.3 | 48.0 | 13.7 | >55 |

TABLE 10-continued

Sequences of the DNA hairpin blocked-
cleavable primers utilized in Example 7.

| Sequence Name | Sequence | SEQ ID NO: |
|---|---|---|
| rs113488022 Forward 4t6d | GCTGTGATTTTGGTCTAGCTACAG TrGAAATGTTTTCATTTC-x | SEQ ID NO: 41 |
| rs113488022 Forward 4t7d | GCTGTGATTTTGGTCTAGCTACAG TrGAAATGTTTTCATTTCA-x | SEQ ID NO: 42 |
| rs113488022 Forward 4t8d | GCTGTGATTTTGGTCTAGCTACAG TrGAAATGTTTTCATTTCAC-x | SEQ ID NO: 43 |
| rs113488022 Forward 4t9d | GCTGTGATTTTGGTCTAGCTACAG TrGAAATGTTTTCATTTCACT-x | SEQ ID NO: 44 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa, x=C3 propanediol spacer block, rG=Guanosine RNA.

Figure 11:
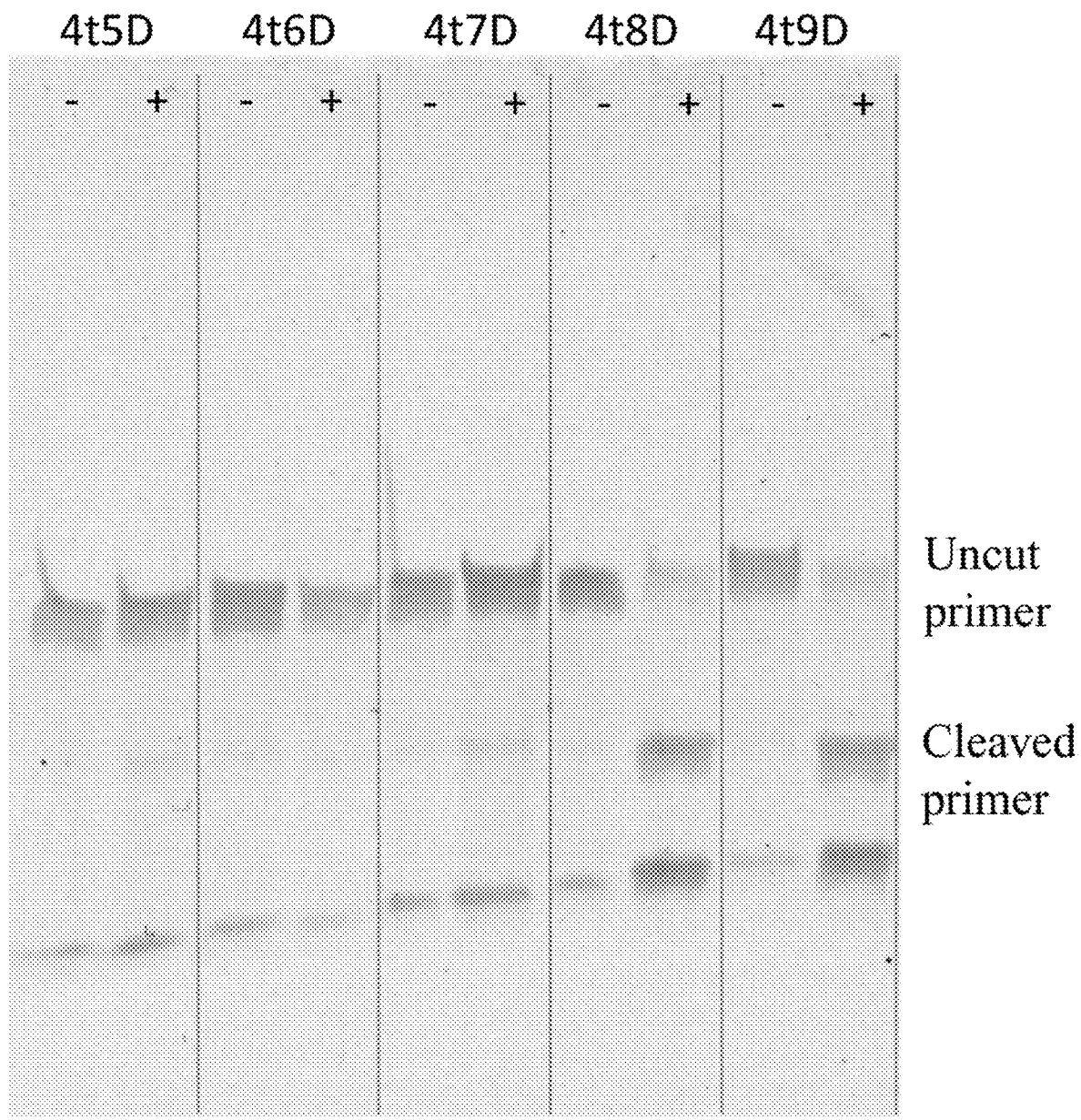
FIG. 11 is a gel image showing cleavage of blocked hairpin primers with 7.5 mU of P.a. RNase H2. Primers were held at 55° C. for 30 minutes and then run in a 15% denaturing acrylamide-urea gel for 2 hours at 16 W. Cleavage was observed to be restricted to the 8 and 9 nucleotide long hairpin primer designs.

50 pmol (2.5 uM) of each of these primers were incubated with 7.5 mU of P.a. RNase H2 at 55° C. for 30 minutes in 1×IDT Genie™ qPCR master mix (IDT, Coralville, Iowa) in a 20 uL reaction volume. The resulting products were run in a denaturing acrylamide gel (15% acrylamide (w/v)) containing 7 M urea for 2 hours at 16 W, and stained with GelRed Nucleic acid stain (Phenix Research, Asheville, N.C.). The results are shown in FIG. 11. Only the 8 and 9 base DNA hairpin primers cleaved under these conditions. This demonstrated that a double-stranded domain extending more than one base 3' of the nucleotide opposite of the RNA residue would result in premature cleavage of the primer. This result was consistent with the prediction from the crystal structure.

Example 8

This example demonstrates that DNA hairpin blocked-cleavable primers are not prematurely cleaved by RNase H2 at room temperature for extended periods.

It was shown in Example 7 that a 55° C. incubation for 30 minutes cleaved only when the hairpin length extended more than a single nucleotide past the site opposite the cleavable RNA, the possibility remained that shorter length DNA hairpins could also be cleaved at lower temperatures and greater time frames, albeit with lowered efficiency.

To determine whether extended incubation of the DNA-hairpin blocked-cleavable primers would allow for inappropriate cleavage events, 50 pmol of each primer was incubated

TABLE 11

Sequences of the DNA hairpin blocked-
cleavable primers utilized in Example 8.

| Sequence Name | Sequence | SEQ ID NO: |
|---|---|---|
| rs113488022 Forward 4t5d | GCTGTGATTTTGGTCTAGCTACAG TrGAAATGTTTTCATTT-x | SEQ ID NO: 40 |
| rs113488022 Forward 4t6d | GCTGTGATTTTGGTCTAGCTACAG TrGAAATGTTTTCATTTC-x | SEQ ID NO: 41 |

TABLE 11-continued

Sequences of the DNA hairpin blocked-
cleavable primers utilized in Example 8.

| Sequence Name | Sequence | SEQ ID NO: |
|---|---|---|
| rs113488022 Forward 4t7d | GCTGTGATTTTGGTCTAGCTACAG TrGAAATGTTTTCATTTCA-x | SEQ ID NO: 42 |
| rs113488022 Forward 4t8d | GCTGTGATTTTGGTCTAGCTACAG TrGAAATGTTTTCATTTCAC-x | SEQ ID NO: 43 |
| rs113488022 Forward 4t9d | GCTGTGATTTTGGTCTAGCTACAG TrGAAATGTTTTCATTTCACT-x | SEQ ID NO: 44 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa, x=C3 propanediol spacer block, rG=Guanosine RNA.

Figure 12:
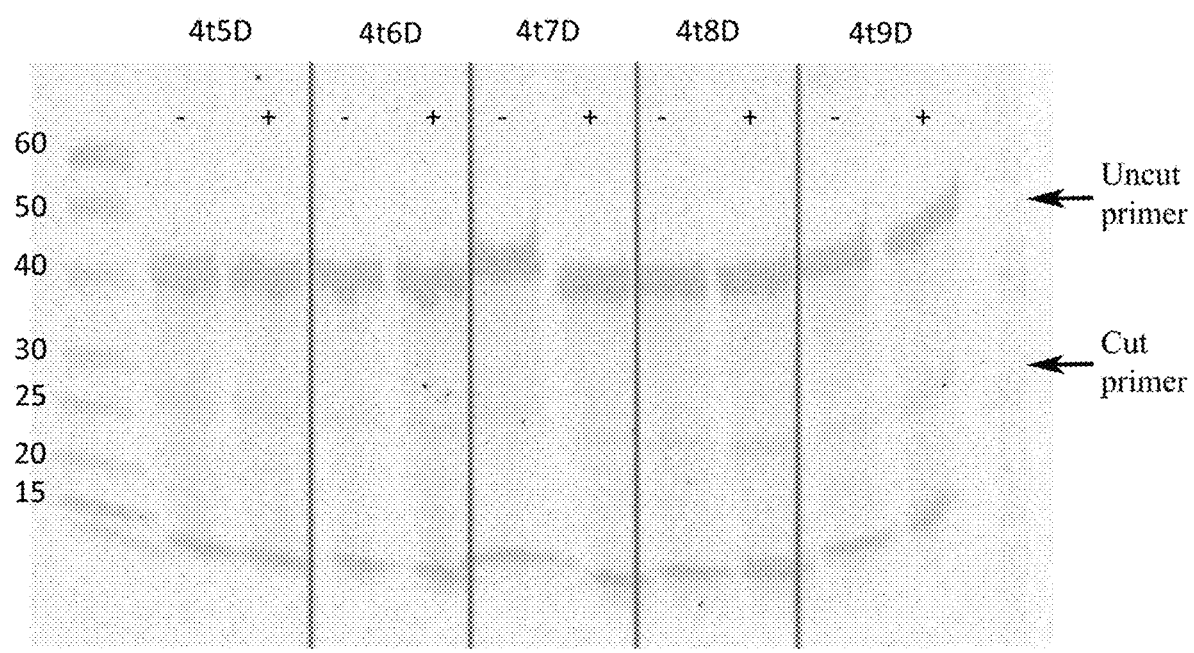
FIG. 12 is a gel image showing an overnight hold of DNA hairpin primers with 7.5 mU RNase H2. After incubation on a bench at room-temperature for 14 hours, no significant cleavage of the DNA hairpin primers is present.

50 pmol (2.5 uM) of each of these primers were incubated with 7.5 mU of P.a. RNase H2 at 25° C. (room temperature) for 16 hours in 1×IDT Genie™ qPCR master mix (IDT, Coralville, Iowa) in a 20 uL reaction volume. The resulting products were run in a denaturing acrylamide gel (15% acrylamide (w/v)) containing 7 M urea for 2 hours at 16 W, and stained with GelRed Nucleic acid stain (Phenix Research, Asheville, N.C.). The results are shown in FIG. 12. None of the DNA hairpin primers cleaved under these conditions. The difference between this result and the one obtained in Example 7 is likely due to the lower activity of the P.a. RNase H2 at room temperature. This results does allow for the conclusion that these primers can be utilized in standard rhPCR reactions, and will not be prematurely cleaved by the RNase H2 enzyme.

Example 9

This example demonstrates the use of DNA hairpin blocked-cleavable primers to detect a SNP.

To demonstrate the utility of DNA hairpin blocked-cleavable primers, the previously described primers designed for detect rs113488022, the V600E mutation in the human BRAF gene were utilized. The hairpin blocked-cleavable primers contain a loop of four thymidine residues. These primers were tested in rhPCR with the H784Q mutant Taq polymerase. The sequences for the primers and templates for these reactions are shown in Table 12.

TABLE 12

The sequences of the oligonucleotides
utilized in Example 9.

| Sequence Name | Sequence | SEQ ID NO: |
|---|---|---|
| Forward non-discriminatory primer | GCTGTGATTTTGGTCTAGCTACAG | SEQ ID NO: 1 |
| Reverse unblocked primer | GCCCTCAATTCTTACCATCCACAAA | SEQ ID NO: 2 |
| Probe | FAM-TCCCATCAG-ZEN-TTTGAACAGTTGTCTGGA-IBFQ | SEQ ID NO: 3 |

TABLE 12-continued

The sequences of the oligonucleotides utilized in Example 9.

| Sequence Name | Sequence | SEQ ID NO: |
|---|---|---|
| rs113488022 Forward 4dmx | GCTGTGATTTTGGTCTAGCTACA GTrGAAATG-x | SEQ ID NO: 4 |
| rs113488022 Forward 4t5d | GCTGTGATTTTGGTCTAGCTACA GTrGAAATGTTTTCATTT-x | SEQ ID NO: 40 |
| rs113488022 Forward 4t6d | GCTGTGATTTTGGTCTAGCTACA GTrGAAATGTTTTCATTTC-x | SEQ ID NO: 41 |
| rs113488022 Forward 4t7d | GCTGTGATTTTGGTCTAGCTACA GTrGAAATGTTTTCATTTCA-x | SEQ ID NO: 42 |
| rs113488022 Forward 4t8d | GCTGTGATTTTGGTCTAGCTACA GTrGAAATGTTTTCATTTCAC-x | SEQ ID NO: 43 |
| rs113488022 Forward 4t9d | GCTGTGATTTTGGTCTAGCTACA GTrGAAATGTTTTCATTTCACT-x | SEQ ID NO: 44 |
| Reverse rhPrimer | GCCCTCAATTCTTACCATCCACA AArATGGAA-x | SEQ ID NO: 11 |
| T-amplicon | GCGTGATTTTGGTCTAGCTACAG TGAAATCTCGATGGAGTGGGTCC CATCAGTTTGAACAGTTGTCTGG ATCCATTTTGTGGATGGTAAGAA TTGAGGGC | SEQ ID NO: 12 |
| A-amplicon | GCGTGATTTTGGTCTAGCTACAG AGAAATCTCGATGGAGTGGGTCC CATCAGTTTGAACAGTTGTCTGG ATCCATTTTGTGGATGGTAAGAA TTGAGGGC | SEQ ID NO: 13 |

Nucleic acid sequences are shown 5'-3'. Location of potential mismatch is underlined. ZEN=internal ZEN™ quencher (IDT, Coralville, Iowa). FAM=6-carboxyfluorescein, IBFQ=Iowa Black® FQ (fluorescence quencher, IDT, Coralville, Iowa), x=C3 propanediol spacer block, rG=Guanosine RNA, rA=Adenine RNA.

The reactions were performed with 7.5 mU (13.6 fmol; 1.36 nM) P.a. RNase H2 in a 10 uL volume of the 1×IDT Genie™ qPCR master mix (IDT, Coralville, Iowa) described above. Reactions were performed in triplicate and results averaged. 500 nM (5 pmol) of each primer and 250 nM (2.5 pmol) of the probe were utilized. 1000 copies of the match or mismatch template (SEQ ID Nos. 12 and 13) were included in each reaction (present as a double-stranded gBlock). Cycling conditions were: $95^{3:00}-(95^{0:15}-65^{0:45})\times 55$. The reaction was performed on a CFX384™ Real-time system (Bio-Rad, Hercules, Calif.). Results are shown in Table 13 below.

TABLE 13

Cq values for the reactions described in Example 9.

| Sequence Name | SEQ ID NO: | T-amplicon | A-amplicon | ΔCq | NTC |
|---|---|---|---|---|---|
| Non-discrim | 1 | 29.4 | 29.7 | | >55 |
| 4dmx | 4 | 31.1 | 43.1 | 11.9 | >55 |
| 4t5d | 40 | 31.6 | 49.8 | 18.2 | >55 |
| 4t6d | 41 | 31.8 | 45.3 | 13.4 | >55 |
| 4t7d | 42 | 32.4 | 44.6 | 12.2 | >55 |
| 4t8d | 43 | 31.4 | 40.0 | 8.7 | >55 |
| 4t9d | 44 | 31.2 | 40.8 | 9.6 | >55 |

This data demonstrates the functional utility of the DNA hairpins is equivalent to the non-hairpin primers in terms of their ability to detect a SNP. The difference in delta Cq values may be the result of random stochastic variation in the system.

Example 10

The following example demonstrates the effect of insertions of napthyl-azo compounds (ZEN) 5' and 3' of the base that is complementary to the RNA residue.

Figure 13A:
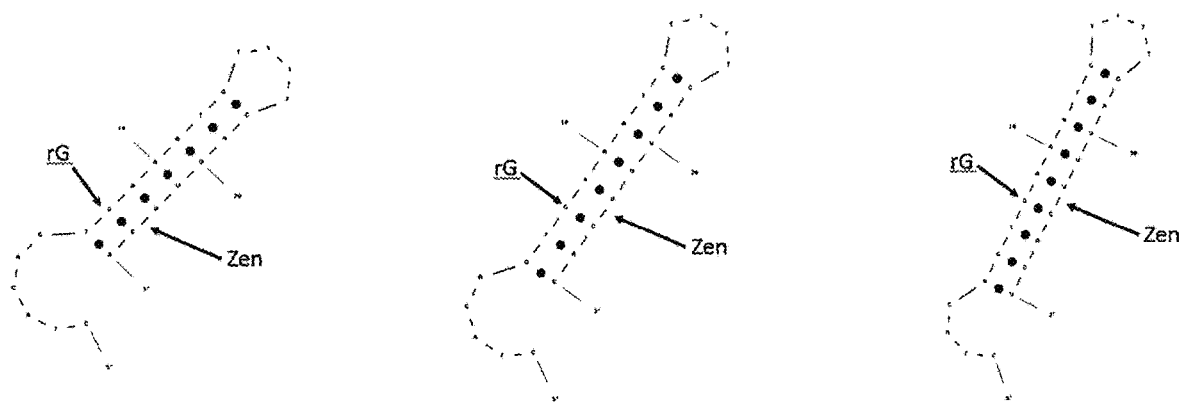
FIGS. 13A and 13B are illustrations of the placement of ZEN napthyl-azo compounds within hairpin primers.
Figure 13:
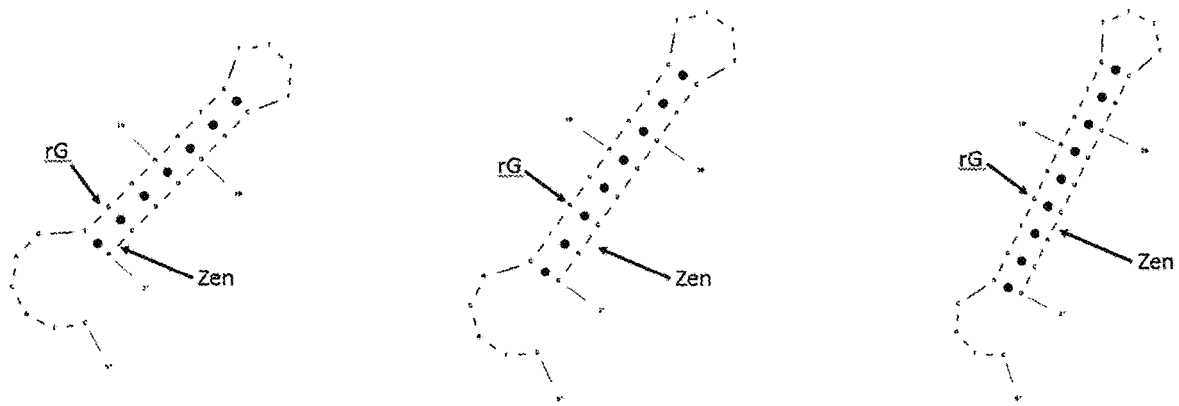

FIGS. 13A and 13B illustrates the hairpin primers tested in this example. The sequences are configured as SEQ ID Nos. 42-44 wherein napthyl-azo compounds are added 5' or 3' to the complementary base.

The reactions were performed with 1×Ver 2.2 Genie master mix (H784Q+7.5 mU Rnase H2) in a 10 uL volume (IDT, Coralville, Iowa). Reactions were performed in triplicate and results averaged. 500 nM (5 pmol) of each primer and 250 nM (2.5 pmol) of the probe were utilized. 1000 copies of the match or mismatch template (SEQ ID Nos. 12 and 13) were included in each reaction (present as a double-stranded gBlock). Cycling conditions were: $95^{3:00}-(95^{0:15}-65^{0:45})\times 65$. The reaction was performed on a CFX384™ Real-time system (Bio-Rad, Hercules, Calif.). Results are shown in Table 14 below.

TABLE 14

Cq values for the reactions described in Example 10

| | Match | Mismatch | ΔCq | NTC |
|---|---|---|---|---|
| Unblocked | 29.7 | 29.9 | | >65 |
| 4Dmx | 31.7 | 42.8 | 11.1 | >65 |
| 4t7d | 32.2 | 46.8 | 14.6 | >65 |
| 4t8d | 31.7 | 40.1 | 8.4 | >65 |
| 4t9d | 31.3 | 40.8 | 9.5 | >65 |
| 4t7d 3' Zen | 31.1 | 45.1 | 14.0 | >65 |
| 4t8d 3' Zen | 32.3 | 44.6 | 12.3 | >65 |
| 4t9d 3' Zen | 31.6 | 45.1 | 13.5 | >65 |
| 4t7d 5' Zen | 32.3 | 47.2 | 14.9 | >65 |
| 4t8d 5' Zen | 31.2 | 49.2 | 18.0 | >65 |
| 4t9d 5' Zen | 31.4 | 45.1 | 13.7 | >65 |

Figure 14:
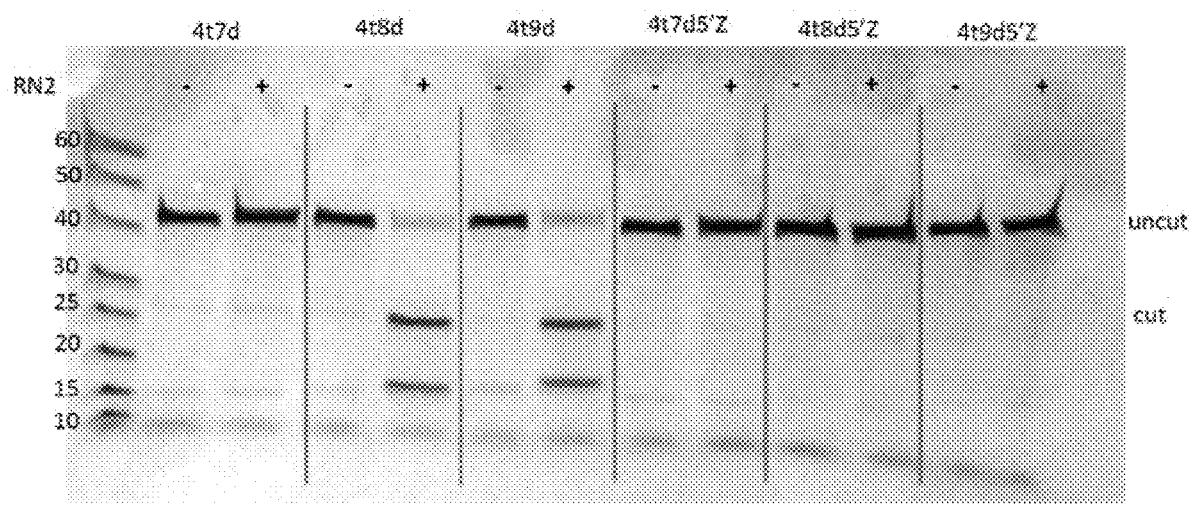
FIG. 14 is a gel illustrating that ZEN napthyl-azo compounds can protect a hairpin primer from unwanted RNase H cleavage.

Table 14 results demonstrate that the internally placed napthyl-azo modifications improve mismatch discrimination. As illustrated in the 15% acrylamide/8 M urea gel in FIG. 14 (stained with 0.2% methylene blue for 30 min., then destained with water for 2 hours), the napthyl-azo modifications protect the primer from RNase H2 while in hairpin configuration. There is little to no cleavage in the modification-containing primers. Therefore an added compound in the primer can disrupt the RNase H from binding and cleaving the primer while in a hairpin configuration, but it does not need to adversely affect the hairpin from forming or unfolding when required to function in the assay.

Example 11

The following example demonstrates the utility of adding a modification at the 3' blocking end of the hairpin primers in order to protect the primer from ssRNase degradation.

Figure 15A:
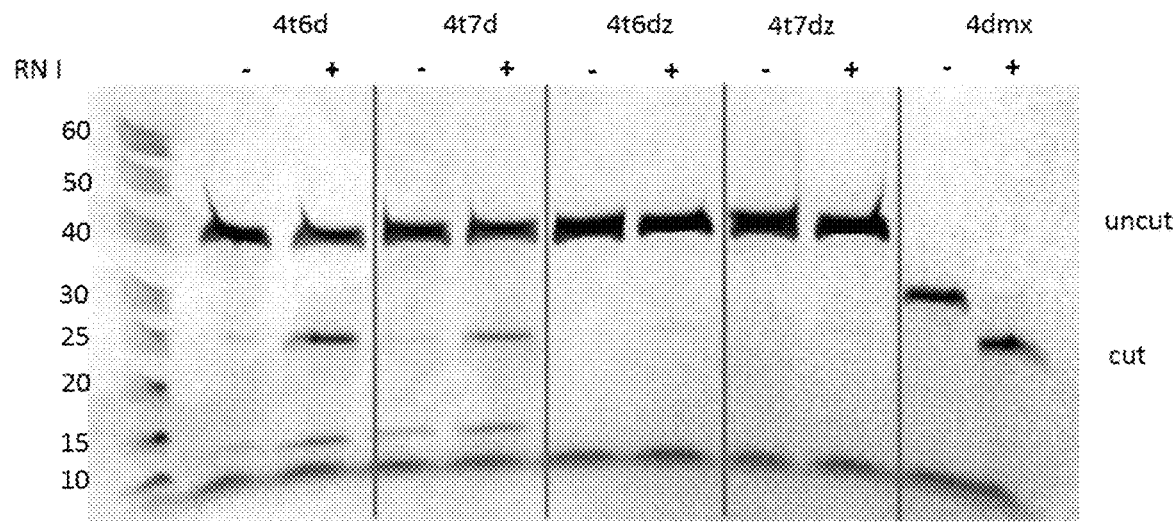
FIGS. 15A and 15B are gels illustrating the effectiveness of ZEN napthyl-azo compounds and biotin to prevent ssRNase degradation of the primers.
Figure 15B:
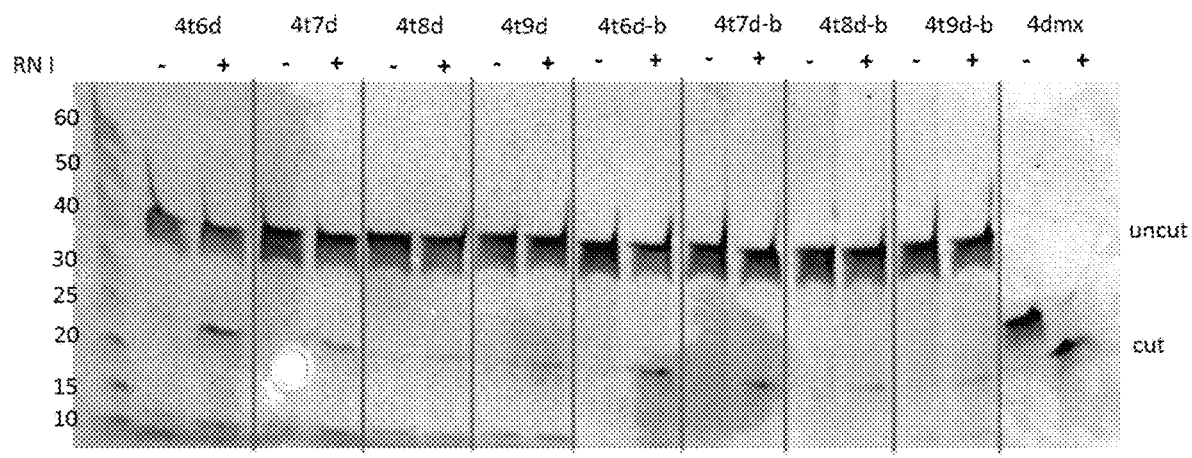

Oligonucleotides of the same sequences as SEQ ID No. 41 and 42 were synthesized except ZEN or biotin modifications were placed on the 3' end of the primer. After subjecting the oligonucleotides to RNase I in a similar fashion as in Example 4. FIGS. 15A and 15B show the resulting gels demonstrating the effectiveness of the addition of the modifications ZEN (15A) and biotin (15B) to the 3' end of the primers. The ZEN compounds at the 3' end nearly eliminate all RNase I degradation compared to the C3 blocking groups, and biotin was equivalent to C3 blocking groups. Therefore multiple modification groups could be used for reducing or eliminating degradation from ssRNases.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of amplifying a target DNA sequence, said method comprising the steps of:
   a) providing a reaction mixture comprising (i) an oligonucleotide hairpin primer having a cleavage domain hybridized to a stem domain and a blocking group at the 3' end of the hairpin primer wherein said blocking group prevents primer extension and/or inhibits the primer from serving as a template for DNA synthesis, (ii) a sample nucleic acid that may or may not have the target sequence, (iii) a cleaving enzyme and (iv) a polymerase;
   b) hybridizing the hairpin primer to the target DNA sequence to unfold the hairpin and form a double-stranded substrate with the target DNA sequence;
   c) cleaving the hybridized primer with said cleaving enzyme at a point within or adjacent to the cleavage domain to remove the stem and blocking group from the primer; and
   d) extending the primer with the polymerase.

2. The method of claim 1 wherein said cleaving enzyme is a sequence-specific double stranded endonuclease.

3. The method of claim 2 wherein said sequence-specific double stranded endonuclease is a restriction enzyme.

4. The method of claim 1 wherein said cleaving enzyme is an RNase H enzyme.

5. The method of claim 1 wherein said cleaving enzyme is an RNase H2 enzyme.

6. The method of claim 1 wherein the cleavage domain comprises 1-4 RNA bases.

7. The method of claim 1 wherein the cleavage domain comprises one RNA base.

8. The method of claim 1 wherein the cleavage domain comprises one or two 2'-fluoronucleosides.

9. The method of claim 1 wherein a discrimination domain is located 5' of the cleavage domain.

* * * * *

SEQUENCE LISTING

```
<160> NUMBER OF SEQ ID NOS: 32

<210> SEQ ID NO 1
<211> LENGTH: 24
<212> TYPE: DNA
<213> ORGANISM: Artificial Sequence
<220> FEATURE:
<223> OTHER INFORMATION: Synthesized oligonucleotide

<400> SEQUENCE: 1
gctgtgattt tggtctagct acag                                              24

<210> SEQ ID NO 2
<211> LENGTH: 25
<212> TYPE: DNA
<213> ORGANISM: Artificial Sequence
<220> FEATURE:
<223> OTHER INFORMATION: Synthesized oligonucleotide

<400> SEQUENCE: 2
gccctcaatt cttaccatcc acaaa                                             25

<210> SEQ ID NO 3
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_signal
<222> LOCATION: (1)..(1)
<223> OTHER INFORMATION: fluorescein
<220> FEATURE:
<221> NAME/KEY: misc_feature
<222> LOCATION: (9)..(9)
<223> OTHER INFORMATION: internal ZEN quencher
<220> FEATURE:
<221> NAME/KEY: misc_signal
<222> LOCATION: (27)..(27)
<223> OTHER INFORMATION: IBFQ quencher
```

```
<400> SEQUENCE: 3
tcccatcagt ttgaacagtt gtctgga                                    27

<210> SEQ ID NO 4
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (31)..(31)
<223> OTHER INFORMATION: C3 spacer

<400> SEQUENCE: 4
gctgtgattt tggtctagct acagtgaaat g                               31

<210> SEQ ID NO 5
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<220> FEATURE:
<221> NAME/KEY: misc_feature
<222> LOCATION: (35)..(38)
<223> OTHER INFORMATION: 2'-O-methyl
<220> FEATURE:
<221> NAME/KEY: misc_feature
<222> LOCATION: (38)..(38)
<223> OTHER INFORMATION: C3 spacer

<400> SEQUENCE: 5
gctgtgattt tggtctagct acagtgaaat ttttuuca                        38

<210> SEQ ID NO 6
<211> LENGTH: 39
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(39)
<223> OTHER INFORMATION: 2'-O-methyl
<220> FEATURE:
<221> NAME/KEY: misc_feature
<222> LOCATION: (39)..(39)
<223> OTHER INFORMATION: C3 Spacer

<400> SEQUENCE: 6
gctgtgattt tggtctagct acagtgaaat ttttuucac                       39

<210> SEQ ID NO 7
<211> LENGTH: 40
<212> TYPE: DNA
<213> ORGANISM: Artificial Sequence
<220> FEATURE:
<223> OTHER INFORMATION: Synthetic oligonucleotide
```

```
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(40)
<223> OTHER INFORMATION: 2'-O-methyl
<220> FEATURE:
<221> NAME/KEY: misc_feature
<222> LOCATION: (40)..(40)
<223> OTHER INFORMATION: C3 spacer

<400> SEQUENCE: 7
gctgtgattt tggtctagct acagtgaaat ttttuucacu                    40

<210> SEQ ID NO 8
<211> LENGTH: 36
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_RNA
<222> LOCATION: (33)..(36)
<223> OTHER INFORMATION: 2'-O-methyl
<220> FEATURE:
<221> NAME/KEY: misc_RNA
<222> LOCATION: (36)..(36)
<223> OTHER INFORMATION: C3 spacer

<400> SEQUENCE: 8
gctgtgattt tggtctagct acagtgaaat ttuuca                        36

<210> SEQ ID NO 9
<211> LENGTH: 37
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (33)..(37)
<223> OTHER INFORMATION: 2'-O-methyl
<220> FEATURE:
<221> NAME/KEY: misc_feature
<222> LOCATION: (37)..(37)
<223> OTHER INFORMATION: C3 spacer

<400> SEQUENCE: 9
gctgtgattt tggtctagct acagtgaaat ttuucac                       37

<210> SEQ ID NO 10
<211> LENGTH: 38
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (33)..(38)
```

```
<223> OTHER INFORMATION: 2'-O-methyl
<220> FEATURE:
<221> NAME/KEY: misc_feature
<222> LOCATION: (38)..(38)
<223> OTHER INFORMATION: C3 spacer

<400> SEQUENCE: 10 gctgtgatttt tggtctagct acagtgaaat ttuucacu                           38

<210> SEQ ID NO 11
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_RNA
<222> LOCATION: (31)..(31)
<223> OTHER INFORMATION: C3 spacer

<400> SEQUENCE: 11
gccctcaatt cttaccatcc acaaaatgga a                                   31

<210> SEQ ID NO 12
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 12
gcgtgatttt ggtctagcta cagtgaaatc tcgatggagt gggtcccatc agtttgaaca    60
gttgtctgga tccattttgt ggatggtaag aattgagggc                         100

<210> SEQ ID NO 13
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 13
gcgtgatttt ggtctagcta cagagaaatc tcgatggagt gggtcccatc agtttgaaca    60
gttgtctgga tccattttgt ggatggtaag aattgagggc                         100

<210> SEQ ID NO 14
<211> LENGTH: 31
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (31)..(31)
<223> OTHER INFORMATION: C3 spacer

<400> SEQUENCE: 14
gccctcaatt cttaccatcc acaaaatgga a                                   31
```

```
<210> SEQ ID NO 15
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 15
gcgtgatttt ggtctagcta cagtgaaatc tcgatggagt gggtcccatc agtttgaaca      60
gttgtctgga tccattttgt ggatggtaag aattgagggc                           100

<210> SEQ ID NO 16
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 16
gcgtgatttt ggtctagcta cagagaaatc tcgatggagt gggtcccatc agtttgaaca      60
gttgtctgga tccattttgt ggatggtaag aattgagggc                           100

<210> SEQ ID NO 17
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(42)
<223> OTHER INFORMATION: 2'-O-methyl
<220> FEATURE:
<221> NAME/KEY: misc_feature
<222> LOCATION: (42)..(42)
<223> OTHER INFORMATION: C3 spacer

<400> SEQUENCE: 17
gctgtgattt tggtctagct acagtgaaat ttttauuuca cu                        42

<210> SEQ ID NO 18
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(43)
<223> OTHER INFORMATION: 2'-O-methyl
<220> FEATURE:
<221> NAME/KEY: misc_feature
<222> LOCATION: (43)..(43)
<223> OTHER INFORMATION: C3 spacer

<400> SEQUENCE: 18
gctgtgattt tggtctagct acagtgaaat ttttauuuca cug                       43

<210> SEQ ID NO 19
<211> LENGTH: 44
<212> TYPE: DNA
```

```
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(44)
<223> OTHER INFORMATION: 2'-O-methyl
<220> FEATURE:
<221> NAME/KEY: misc_feature
<222> LOCATION: (44)..(44)
<223> OTHER INFORMATION: C3 spacer

<400> SEQUENCE: 19
gctgtgattt tggtctagct acagtgaaat ttttauuuca cugu            44

<210> SEQ ID NO 20
<211> LENGTH: 42
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(42)
<223> OTHER INFORMATION: 2'-O-methyl
<220> FEATURE:
<221> NAME/KEY: misc_feature
<222> LOCATION: (42)..(42)
<223> OTHER INFORMATION: C3 spacer

<400> SEQUENCE: 20
gctgtgattt tggtctagct acagtgaaat gtttauuuca cu              42

<210> SEQ ID NO 21
<211> LENGTH: 43
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
<220> FEATURE:
<221> NAME/KEY: misc_feature
<222> LOCATION: (35)..(43)
<223> OTHER INFORMATION: 2'-O-methyl
<220> FEATURE:
<221> NAME/KEY: misc_feature
<222> LOCATION: (43)..(43)
<223> OTHER INFORMATION: C3 spacer

<400> SEQUENCE: 21
gctgtgattt tggtctagct acagtgaaat gtttauuuca cug             43

<210> SEQ ID NO 22
<211> LENGTH: 44
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (26)..(26)
<223> OTHER INFORMATION: RNA base
```

```
<220> FEATURE:
<221> NAME/KEY: misc_feature
<222> LOCATION: (35)..(44)
<223> OTHER INFORMATION: 2'-O-methyl
<220> FEATURE:
<221> NAME/KEY: misc_feature
<222> LOCATION: (44)..(44)
<223> OTHER INFORMATION: C3 spacer

<400> SEQUENCE: 22
gctgtgattt tggtctagct acagtgaaat gtttauuuca cugu                44

<210> SEQ ID NO 23
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 23
accgtgcagc tcatcat                                              17

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
acctaaagcc acctccttac t                                         21

<210> SEQ ID NO 25
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (18)..(18)
<223> OTHER INFORMATION: RNA base
<220> FEATURE:
<221> NAME/KEY: misc_feature
<222> LOCATION: (23)..(23)
<223> OTHER INFORMATION: C3 spacer

<400> SEQUENCE: 25
accgtgcagc tcatcatgca gca                                       23

<210> SEQ ID NO 26
<211> LENGTH: 34
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (18)..(18)
<223> OTHER INFORMATION: RNA base
<220> FEATURE:
<221> NAME/KEY: misc_feature
<222> LOCATION: (27)..(34)
<223> OTHER INFORMATION: 2'-O-methyl
<220> FEATURE:
<221> NAME/KEY: misc_feature
<222> LOCATION: (34)..(34)
<223> OTHER INFORMATION: C3 spacer

<400> SEQUENCE: 26
```
accgtgcagc tcatcatgca gcatttgctg caug                                    34

<210> SEQ ID NO 27
<211> LENGTH: 35
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (18)..(18)
<223> OTHER INFORMATION: RNA base
<220> FEATURE:
<221> NAME/KEY: misc_feature
<222> LOCATION: (27)..(35)
<223> OTHER INFORMATION: 2'-O-methyl
<220> FEATURE:
<221> NAME/KEY: misc_feature
<222> LOCATION: (35)..(35)
<223> OTHER INFORMATION: C3 spacer

<400> SEQUENCE: 27
accgtgcagc tcatcatgca gcatttgctg cauga                                   35

<210> SEQ ID NO 28
<211> LENGTH: 36
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (18)..(18)
<223> OTHER INFORMATION: RNA base
<220> FEATURE:
<221> NAME/KEY: misc_feature
<222> LOCATION: (25)..(36)
<223> OTHER INFORMATION: 2'-O-methyl
<220> FEATURE:
<221> NAME/KEY: misc_feature
<222> LOCATION: (36)..(36)
<223> OTHER INFORMATION: C3 spacer

<400> SEQUENCE: 28
accgtgcagc tcatcatgca gcatttgctg caugau                                  36

<210> SEQ ID NO 29
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_RNA
<222> LOCATION: (22)..(22)
<223> OTHER INFORMATION: RNA base
<220> FEATURE:
<221> NAME/KEY: misc_feature
<222> LOCATION: (27)..(27)
<223> OTHER INFORMATION: C3 spacer

<400> SEQUENCE: 29
acctaaagcc acctccttac tutgcca                                            27

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_signal

```
<222> LOCATION: (1)..(1)
<223> OTHER INFORMATION: fluorescein
<220> FEATURE:
<221> NAME/KEY: misc_feature
<222> LOCATION: (9)..(9)
<223> OTHER INFORMATION: ZEN quencher
<220> FEATURE:
<221> NAME/KEY: misc_signal
<222> LOCATION: (23)..(23)
<223> OTHER INFORMATION: IBFQ quencher

<400> SEQUENCE: 30
ccttcggctg cctcctggac tat                                           23

<210> SEQ ID NO 31
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 31
accgtgcagc tcatcatgca gctcatgccc ttcggctgcc tcctggacta tgtccgggaa    60
cacaaagaca atattggctc ccagtacctg ctcaactggt                         100

<210> SEQ ID NO 32
<211> LENGTH: 100
<212> TYPE: DNA
<213> ORGANISM: Artificial Sequence
<220> FEATURE:
<223> OTHER INFORMATION: Synthetic oligonucleotide

<400> SEQUENCE: 32
accgtgcagc tcatcacgca gctcatgccc ttcggctgcc tcctggacta tgtccgggaa    60
cacaaagaca atattggctc ccagtacctg ctcaactggt                         100
```